United States Patent [19]

Harnden et al.

[11] Patent Number: 4,965,270

[45] Date of Patent: Oct. 23, 1990

[54] PURINE DERIVATIVES

[75] Inventors: Michael R. Harnden; Paul G. Wyatt; Stuart Bailey, all of Epsom, England

[73] Assignee: Beecham Group p.l.c., Brentford, England

[21] Appl. No.: 433,011

[22] Filed: Nov. 7, 1989

Related U.S. Application Data

[63] Continuation of Ser. No. 199,382, May 27, 1988, abandoned, which is a continuation-in-part of Ser. No. 944,373, Dec. 11, 1986, abandoned.

[51] Int. Cl.$^5$ .................. C07D 473/18; A61K 31/52
[52] U.S. Cl. .................................. 514/262; 544/276; 544/277; 514/261
[58] Field of Search ............... 544/276, 277; 514/262, 514/261

[56] References Cited

U.S. PATENT DOCUMENTS

| | | | |
|---|---|---|---|
| 4,609,662 | 9/1986 | Krenitsky | 544/276 |
| 4,621,140 | 11/1986 | Verbeyden | 544/277 |
| 4,755,516 | 7/1988 | Tolman et al. | 544/276 |

FOREIGN PATENT DOCUMENTS

| | | |
|---|---|---|
| 0158847 | 10/1985 | European Pat. Off. . |
| 0186640 | 7/1987 | European Pat. Off. . |
| 0242482 | 10/1987 | European Pat. Off. . |

OTHER PUBLICATIONS

Watson, J. Org. Chem. vol. 39, pp. 2911-2116 (1974).

Primary Examiner—Nicholas S. Rizzo
Attorney, Agent, or Firm—Hopgood, Calimafde, Kalil, Blaustein & Judlowe

[57] ABSTRACT

Compounds of formula (I), and pharmaceutically acceptable salts thereof:

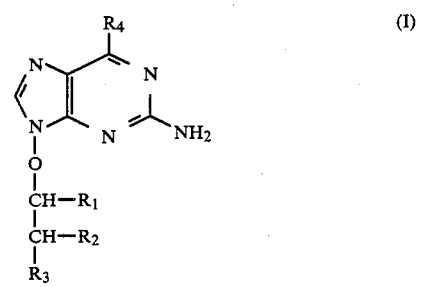

wherein
$R_1$ is hydrogen or $CH_2OH$;
$R_2$ is hydrogen or, when $R_1$ is hydrogen, hydroxy or $CH_2OH$;
$R_3$ is $CH_2OH$ or, when $R_1$ and $R_2$ are both hydrogen, $CH(OH)CH_2OH$;
$R_4$ is hydrogen, hydroxy, amino or $OR_5$ wherein
$R_5$ is $C_{1-6}$ alkyl, phenyl or phenyl $C_{1-2}$ alkyl either of which phenyl moieties may be substituted by one or two halo, $C_{1-4}$ alkyl or $C_{1-4}$ alkoxy groups;
and in which any OH groups in $R_1$, $R_2$ and $R_3$ may be in the form of O-acyl, phosphate, cyclic acetal or cyclic carbonate derivatives thereof; having antiviral activity.

13 Claims, No Drawings

PURINE DERIVATIVES

This application is a continuation of U.S. Ser. No. 199,382, filed May 27, 1988 now abandoned, which is a continuation-in-part of Ser. No. 944,373, filed Dec. 11, 1986 (abandoned).

The present invention relates to compounds having antiviral activity, to processes for their preparation and to their use as pharmaceuticals.

9-[(2-hydroxyethoxy)methyl]guanine (Acyclovir), 9-(1,3-dihydroxy-2-propoxymethyl)-guanine (DHPG) and 9-(4-hydroxy-3-hydroxymethylbut-1-yl)guanine, (disclosed in EP-A-No. 141927), are all guanine derivatives having antiviral activity.

A novel, structurally distinct class of compounds has now been discovered, these compounds also having antiviral activity.

Accordingly, the present invention provides a compound of formula (I), or a pharmaceutically acceptable salt thereof:

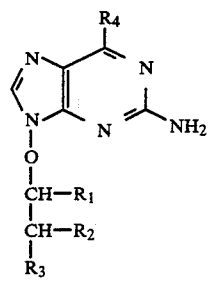

wherein
$R_1$ is hydrogen or $CH_2OH$;
$R_2$ is hydrogen or, when $R_1$ is hydrogen, hydroxy or $CH_2OH$;
$R_3$ is $CH_2OH$ or, when $R_1$ and $R_2$ are both hydrogen, $CH(OH)CH_2OH$;
$R_4$ is hydrogen, hydroxy, amino or $OR_5$
wherein
$R_5$ is $C_{1-6}$ alkyl, phenyl or phenyl $C_{1-2}$ alkyl either of which phenyl moieties may be substituted by one or two halo, $C_{1-4}$ alkyl or $C_{1-4}$ alkoxy groups;
and in which any OH groups in $R_1$, $R_2$ and $R_3$ may be in the form of O-acyl, phosphate, cyclic acetal or cyclic carbonate derivatives thereof.

There are groups of compounds within formula (I) as follows:
(a) $R_1$ and $R_2$ are both hydrogen and $R_3$ is $CH_2OH$, and derivatives thereof as defined;
(b) $R_1$ is hydrogen and $R_2$ and $R_3$ are both $CH_2OH$, and derivatives thereof as defined;
(c) $R_1$ is hydrogen, $R_2$ is hydroxy and $R_3$ is $CH_2OH$, and derivatives thereof as defined;
(d) $R_1$ is $CH_2OH$, $R_2$ is hydrogen and $R_3$ is $CH_2OH$, and derivatives thereof as defined.
(e) $R_1$ and $R_2$ are both hydrogen and $R_3$ is $CH(OH)CH_2OH$, and derivatives thereof as defined.

Examples of $R_5$ include methyl, ethyl, n- and iso-propyl, phenyl and benzyl optionally substituted by one or two of methyl, ethyl, n- and iso-propyl, methoxy, ethoxy, n- and iso- propoxy, fluoro, chloro or bromo.

O-Acyl derivatives are normally those wherein one or two OH groups in $R_1$, $R_2$ and/or $R_3$ form carboxylic ester groups; such as $C_{1-7}$ alkanoyl and benzoyl optionally substituted by one or two $C_{1-4}$ alkyl, $C_{1-4}$ alkoxy, halogen or $CF_3$ groups. Preferably, carboxylic ester groups are $C_{1-7}$ alkanoyl groups, such as acetyl, propionyl, butyryl, heptanoyl and hexanoyl, most preferably acetyl or propionyl.

Examples of phosphate esters of the compounds of formula (I) include those where one of the acyclic —OH groups is replaced by $(HO)_2$—$PO_2$— groups or salts thereof, or where two —OH groups on carbon atoms are replaced by a bridging —O—$P(OH)O_2$— group.

When $R_1$, $R_2$ and $R_3$ together contain two OH groups, cyclic acetal groups, such as —O—$C(C_{1-3}$alkyl$)_2$—O— or cyclic carbonate, such as —O—CO—O— may be formed.

It is believed that the groups of compounds within formula (I) which are preferred are those indicated hereinbefore as (a) and (b); and that $R_4$ is preferably hydroxy or hydrogen.

Examples of pharmaceutically acceptable salts of the compound of formula (I) are acid addition salts formed with a pharmaceutically acceptable acid such as hydrochloric acid, orthophosphoric acid and sulphuric acid. Pharmaceutically acceptable salts also include those formed with organic bases, preferably with amines, such as ethanolamines or diamines; and alkali metals, such as sodium and potassium.

When the compound of formula (I) contains a phosphate group suitable salts include metal salts, such as alkali metal salts, for example sodium or potassium, alkaline earth metal salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)-amine or tris-(2-hydroxyethyl)-amine.

It will be appreciated that some of the compounds of formula (I) have at least one asymmetric centre, and therefore are capable of existing in more than one stereoisomeric form. The invention extends to each of these forms individually and to mixtures thereof, including racemates. The isomers may be separated conventionally by chromatographic methods or using a resolving agent. Alternatively, the individual isomers may be prepared by asymmetric synthesis using chiral intermediates.

It will be further appreciated that, when $R_4$ is hydroxy in formula (I), the compound exists in the preferred tautomeric form of formula (IA):

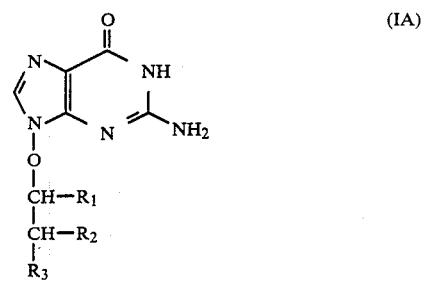

The compounds of formula (I), including their alkali metal salts, may form solvates such as hydrates and these are included wherever a compound of formula (I) or a salt thereof is herein referred to.

It will also be appreciated that compounds of formula (I) wherein $R_4$ is other than hydroxy are pro-drugs for the compounds of formula (I) wherein $R_4$ is hydroxy.

The invention also provides a process for the preparation of a compound of formula (I), or a pharmaceutically acceptable salt thereof, which process comprises cyclising a compound of formula (II):

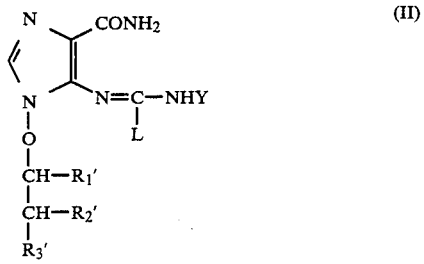

wherein L is a sulphur leaving group or $NH_2$, Y is a protecting group and $R_1'$, $R_2'$ and $R_3'$ are $R_1$, $R_2$ and $R_3$ respectively or $R_1$, $R_2$ and/or $R_3$ wherein OH groups are protected; and thereafter, when $R_4$ in the desired compound of formula (I) is other than hydroxy, converting an $R_4$ hydroxy group to chloro, followed by either (i) reduction to $R_4$ is hydrogen, (ii) replacement of chloro by $NH_2$ to give $R_4$ is amino; or (iii) reaction with $OR_5^-$ ion to give $R_4$ is $OR_5$; and deprotecting Y and converting $R_1'$ to $R_1$, $R_2'$ to $R_2$ and $R_3'$ to $R_3$ when desired or necessary, and optionally forming a pharmaceutically acceptable salt, O-acyl, phosphate, cyclic acetal or cyclic carbonate derivative thereof.

The cyclisation when L is a sulphur leaving group may take place in the presence of ammonia in an inert solvent, such as dimethylformamide; or, more preferably in basic conditions such as in 7M sodium hydroxide and dimethylsulphoxide; at elevated temperatures 80°–150° C., preferably 100°–1200° C.

Suitable values for L then include alkylthio groups, such as methylthio, ethylthio, n- and iso-propylthio. Preferably L is methylthio.

When L is $NH_2$, the reaction preferably takes place in more weakly basic conditions, such as in 1M sodium hydroxide, at elevated temperatures 80°–150° C., preferably 100°–120° C.

Suitable values for Y include hydrolysable NH protecting groups, such as benzoyl optionally substituted as hereinbefore described for $R_5$ when phenyl. Y is preferably benzoyl.

Conversion of an $R_4$ hydroxy group to chloro may be achieved by chlorination using a reagent such as phosphorus oxychloride, preferably in the presence of tetraethylammonium chloride and dimethylaniline (as acid acceptor) in $CH_3CN$ at reflux temperatures, according to the method described by M. J. Robins and B. Uzanski, *Can. J. Chem.* 59, 2601(1981).

Reduction of a resulting chloro compound may preferably be achieved using catalytic methods, such as palladium on charcoal in an inert solvent, such as methanol or ethanol at reflux temperatures. The hydrogen source may be cyclohexene or ammonium formate. The procedure is analogous to that described in Example 1 of EP-A-No. 182024 or to that described by T. A. Krenitsky et.al. *Proc.Natl.Acad Sci. U.S.A.* 81, 3209 (1984).

Conversion to $R_4$ is amino may be achieved conventionally by treatment with ammonia in methanol in an autoclave at 100° C. for a period of about 7 hours, or alternatively, with sodium azide in dimethylformamide to form an azido intermediate (wherein $R_4$ is $N_3$), followed by reduction of this intermediate with ammonium formate/palladium on charcoal, in methanol.

Reaction with $OR_5^-$ with the resulting chloro compound may be achieved using, preferably, $NaOR_5$ in a suitable solvent, such as methanol or ethanol when $R_5$ is methyl or ethyl respectively, at 0°–150° C., preferably around 50° C. The procedure is analogous to that described in Example 15 of EP-A-No. 141927.

Deprotection of Y may take place by conventional basic hydrolysis, such as aqueous sodium hydroxide at 100° C.

$R_1'$, $R_2'$ and/or $R_3'$ when protected OH groups, the protecting group(s) are often hydrogenolysable such as a benzyl group optionally substituted as defined above for $R_5$ when phenyl, also including nitro as an optional substituent.

Removal of benzyl protecting groups may be achieved conventionally, by catalytic hydrogenation using palladium on charcoal as catalyst (when $R_4$ is other than hydrogen).

Other suitable protecting groups include substituted benzyl groups such as p-methoxybenzyl, removable by treatment with DDQ, described in Example 8 hereinafter.

Another suitable protecting groups is the t-Butyl dimethylsilyl group removable by 80% acetic acid at elevated temperatures, around 90° C., or treatment with tetrabutyl ammonium fluoride in a solvent such as tetrahydrofuran, at ambient temperature.

Another suitable protecting group is wherein two OH groups or carbon atoms α- or β- to one another are reacted with 2,2-dimethoxypropane, forming a 1,3-dioxolan or 1,3-dioxan ring respectively. This group may be removed by acidic hydrolysis.

Alternative values for $R_2'$ and $R_3'$, when protected OH groups, include that wherein two OH groups on adjacent carbon atoms are replaced by a bond; for example, when $R_1$ is hydrogen, $R_2$ is hydroxy and $R_3$ is $CH_2OH$; $R_3'CHR_2'CHR_1'O-$ is $CH_2=CH-CH_2-O-$. The diol formation ('deprotection') may be achieved conventionally, for example, using osmium tetroxide, preferably catalytically in the presence of N-methylmorpholine N-oxide.

Pharmaceutically acceptable salts, O-acyl derivatives and phosphate derivatives may be prepared conventionally, for example as described in EP-A-No. 141927 and EP-A-No. 182024.

Acyl derivatives of compounds of formula (I) may be prepared by acylating an optionally protected compound of formula (I) in accordance with conventional acylating processes known in the art, and where necessary, deprotecting the resulting product.

The acylation reaction may be carried out by using an acylating agent containing a suitable carboxylic acid acyl group.

Examples of acylating agents suitable for the above process are carboxylic acids, acid halides, such as chlorides or acid anhydrides, preferably anhydrides or acids.

When the acylating agent is a carboxylic acid, a condensation promoting agent such as dicyclohexylcarbodiimide should be included, but this is not necessary when the acylating agent is an acid anhydride.

The acylation reaction may produce a single acyl derivative of a compound of formula (I), or a mixture of derivatives, depending on a number of factors, such as the relative amounts and chemical natures of reactants, the physical conditions of the reaction, and the solvent system. Any mixture produced in this way may be separated into its pure components using standard chromatographic techniques.

The above described acylation process of the invention can yield mono- or di-acylated derivatives of compounds of formula (I) containing two OH groups, according to the form of protection/deprotection utilised. The following are examples of products obtained by different methods:

(a) Acylated derivatives of the OH groups in $R_1/R_2/R_3$ when both acyl groups are the same, may be obtained by direct acylation of compounds of formula (I).

(b) Mono-acylated derivatives of one OH group when $R_1$, $R_2$ and $R_3$ together contain two OH groups may be obtained by acylation of protected intermediates of compounds of formula (I) in which the other —OH group in $R_1/R_3/R_3$ is preferably protected by, for example, a monomethoxytrityl or trityl group, and subsequent deprotection by acid treatment. Diacylated derivatives wherein the acyl groups are different may then be prepared as in (a).

Acyl derivatives of the compounds of formula (I) can be converted to a compound of formula (I) by conventional deacylation or partial deacylation processes. For example, reaction with methanolic ammonia can be used to effect complete deacylation to yield a compound of formula (I) the to both OH groups are deacylated. Reaction with a mild base such as potassium carbonate can result in partial deacylation of a di-acylated derivative to produce a compound of formula (I) wherein one acyl group and one OH group are present.

Phosphate derivatives are formed by reaction with a phosphorylating agent such as phosphorus oxychloride in pyridine. The $NH_2$ and any OH groups in $R_1$, $R_2$ and/or $R_3$ are protected as desired or necessary, preferably using a trityl or methoxytrityl protecting group, removable by acid hydrolysis, using acetic acid.

When more than one OH group in $R_1$, $R_2$ and $R_3$ is phosphorylated, a cyclic phosphate derivative is produced with phosphorus oxychloride, when the OH groups are $\alpha$ or $\beta$ to one another.

Another suitable phosphorylating agent is cyanoethyl phosphoric acid, in which case the product is normally treated with aqueous ammonia, which yields the ammonium salt of the phosphate ester as the final product.

A monophosphate may be converted to a cyclic phosphate using a dehydrating agent, such as dicyclohexylcarbodiimide.

Cyclic acetal derivatives of the compounds of formula (I) may be prepared from the compound of formula (I) wherein two OH groups in the side chain are present, preferably $\beta$- to one another, using an acyclic acetal, such as $R_{10}O-C(C_{1-3}alkyl)_2-OR_{10}$ wherein $R_{10}$ is $C_{1-4}$ alkyl, such as methyl or ethyl. The reaction is preferably carried out in an inert solvent such as tetrahydrofuran or dimethylformamide in the presence of an acid such as p-toluenesulphonic acid.

Cyclic carbonate derivatives of the compounds of formula (I) may be prepared from the compound of formula (I), wherein the $-NH_2$ group is preferably protected; with phosgene or 1,1-carbonyldimidazole, and thereafter deprotecting where necessary. Suitable protecting groups include trityl and monomethoxytrityl. The reaction is preferably carried out in dry pyridine at 0°–50° C., preferably at ambient temperature.

It will be appreciated that conversions of $R_4$, deprotections and derivative formations may take place in any desired or necessary order.

Compounds of the formula (II) may be prepared according to the following reaction scheme:

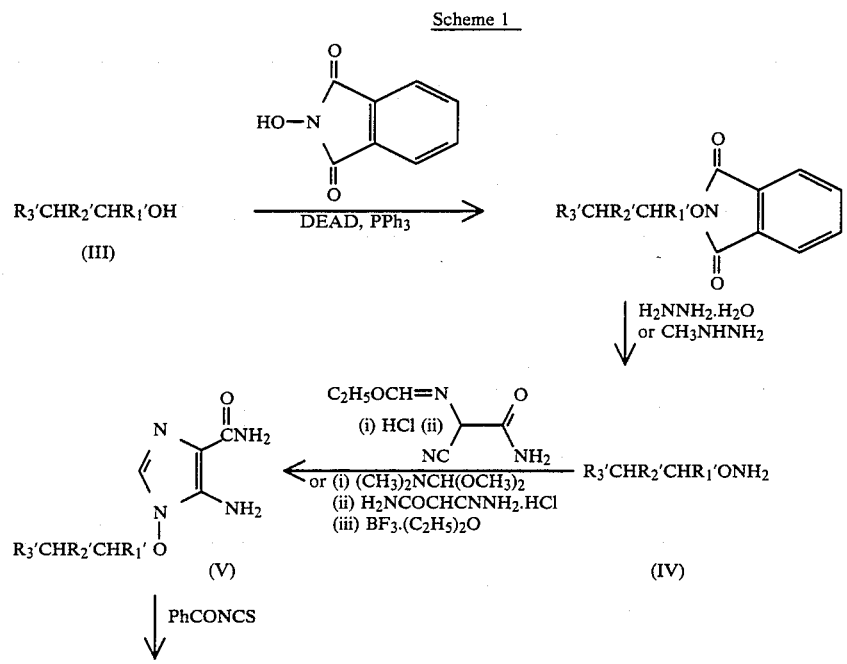

Scheme 1

-continued
Scheme 1

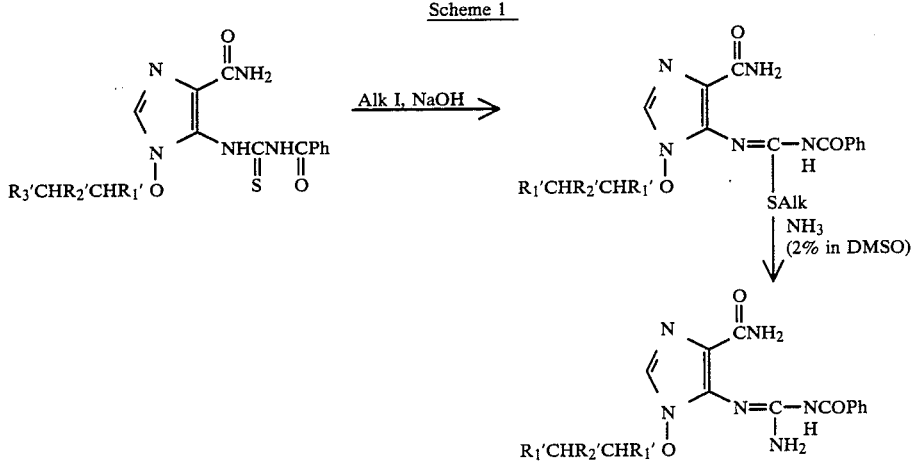

Alk is an alkyl group, such as methyl.

These methods are described in detail in Descriptions 1 and 6 hereinafter.

Compounds of the formula (III) are known or prepared by methods analogous to those used for the preparation of structurally similar known compounds.

Intermediates of the formulae (II) and (V) are novel and form an aspect of the invention.

Intermediates of the formula (IV), other than those wherein two OH groups on adjacent carbon atoms are replaced by a bond, are believed to be novel and also form an aspect of the invention.

The invention provides a further (preferred) process for the preparation of a compound of formula (I), or a pharmaceutically acceptable salt thereof, which process comprises converting the chloro group in a compound of formula (VI):

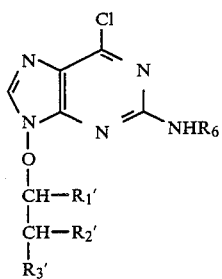

(VI)

wherein $R_6$ is hydrogen or an N-protecting group, such as $C_{1-7}$ alkanoyl, and $R_1'$, $R_2'$ and $R_3'$ are as hereinbefore defined, by either (i) hydrolysis to give $R_4$ as hydroxy, (ii) reduction to give a compound of formula (I) wherein $R_4$ is hydrogen, (iii) replacement of chloro by $NH_2$ to give $R_4$ is amino; or (iv) reaction with $OR_5^-$ to give a compound of formula (I) wherein $R_4$ is $OR_5$, and thereafter converting $R_1'$ to $R_1$, $R_2'$ to $R_2$ and/or $R_3'$ to $R_3$ when necessary, and/or optionally forming a pharmaceutically acceptable salt or derivative thereof as defined.

The hydrolysis (i) may be carried out using aqueous mineral acid, such as hydrochloric acid, or more preferably using an organic acid, such as formic acid at elevated temperature, suitably 70°–150° C., preferably 100° C.

Reactions (ii), (iii) and (iv) above may be carried out as hereinbefore described for (i), (ii) and (iii) respectively under the process utilising a compound of formula (II).

Suitable values for protected OH groups in $R_1'$, $R_2'$ and $R_3'$ and methods for deprotection of groups in $R_1'$, $R_2'$ and $R_3'$ and methods for deprotection and formation of salts and derivatives are also described under the process utilising a compound of formula (II).

Compounds of the formula (VI) may be prepared by chlorination of the corresponding compound of formula (I) wherein $R_4$ is hydroxy, or, more preferably, from the compound of formula (VII):

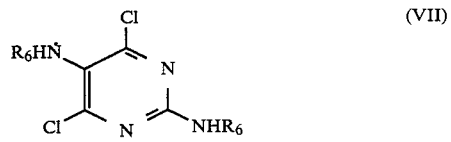

(VII)

wherein $R_6$ is formyl; by reaction with the compound of formula (IV) as hereinbefore defined, followed by cyclisation of the resulting compound of formula (VIII):

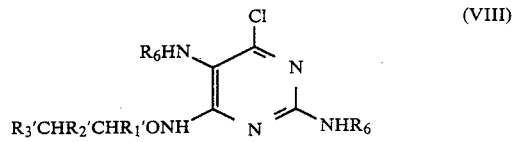

(VIII)

wherein $R_6$ is formyl; either with a suitable cyclisation condensing agent such as diethoxymethylacetate or triethylorthoformate, or by fusion. Suitable conditions for these reactions include those described hereinafter in Descriptions 2 to 5.

The compound of formula (VII) wherein $R_6$ is formyl may be prepared by reaction of the corresponding compound of formula (VII) wherein $R_6$ is hydrogen with formic acid and acetic anhydride.

The compound of formula (VII) wherein $R_6$ is hydrogen, 2,5-diamino-4,6-dichloropyrimidine is a known compound as described in C. Temple, Jr, B. H. Smith and J. A. Montgomery, J. Org. Chem., 40 (21), 3141, 1975.

Compounds of the formula (VI) and (VIII) are novel and form an aspect of the invention.

The present invention provides a process for the preparation of a compound of formula (I) wherein $R_4$ is hydrogen, or a pharmaceutically acceptable salt thereof, which process comprises the ring closure of a compound of formula (IX):

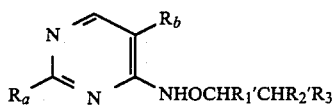  (IX)

wherein $R_a$ is amino or a group or atom convertible thereto; $R_b$ is amino or an amino derivative and $R_1'$, $R_2'$ and $R_3'$ are $R_1$, $R_2$ and $R_3$ respectively or $R_1$, $R_2$, and/or $R_3$ wherein OH group(s) is/are protected; and thereafter converting $R_a$ when other than amino, to amino; $R_1'$ to $R_1$, $R_2'$ to $R_2$ and/or $R_3'$ to $R_3$ when necessary and-/or optionally forming a pharmaceutically acceptable salt or derivative thereof as defined.

The ring closure may take place using a suitable cyclisation condensing agent such as diethoxymethylacetate or triethylorthoformate or by fusion. These methods are generally described in 'Comprehensive Organic Chemistry' p499–504, 1979, Vol 4. D. H. R. Barton and W. D. Ollis eds.).

Suitable values for $R_a$ include chloro, amino and formylamino. $R_a$ when chloro may be converted to amino by conventional methods, such as those described above for conversion of $R_4$ is chloro to $R_4$ is amino, or by reaction with hydrazine followed by reduction, or using $(CH_3)_3SiNH_2$ in toluene. $R_a$ is formylamino may be converted to amino by conventional methods, such as that using aqueous hydrazine in ethanol at reflux temperatures.

Preferably $R_b$ is formylamino; although it may also be amino or ortho ester amino, such as —NH—CH—$(OC_2H_5)_2$.

Suitable values for protected OH groups in $R_1'$, $R_2'$ and $R_3'$ and methods for deprotection of protected OH groups in $R_1'$, $R_2'$ and $R_3'$ and methods for deprotection and formation of salts and derivatives are as described above.

Compounds of the formula (IX) may be prepared by reaction of a compound of formula (X):

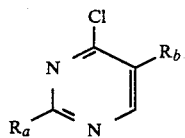  (X)

with a compound of formula (IV) as hereinbefore defined.

This reaction is carried out in accordance with the procedures described in Description 18 hereinafter, in an inert solvent, such as 2-methoxyethyl ether at elevated temperatures, around 100° C., in the presence of an acid acceptor, such as diisopropylethylamine.

Intermediates of formula (X) are known or prepared by analogous methods. For example, the compound of formula (X) wherein $R_a$ is chloro and $R_b$ is amino may be prepared as follows:

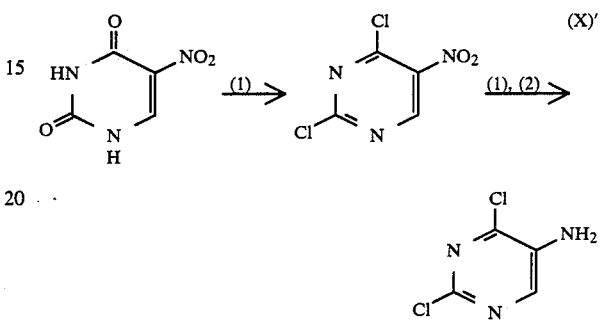  (X)'

(1) Whittaker. J. Chem. Soc (1951). 1565.
(2)(a) Inove Chem. Pharm. Bull (Japan) 6, 343, (1958).
(b) Inove Chem. Pharm. Bull (Japan) 6, 349, (1958).

The compound of formula (X) wherein $R_a$ is amino and $R_b$ is amino may be prepared as follows:

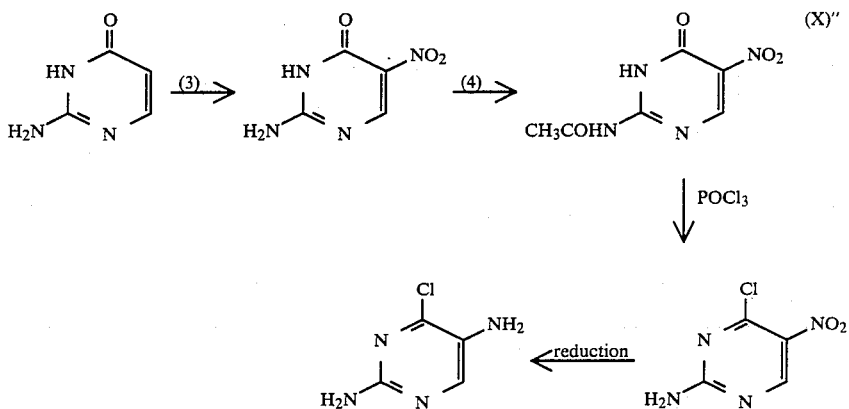  (X)"

(3) Johns Am. Chem. J. 34, 554, (1905).
(4) Tong, Lee and Goodman, J.A.C.S. 86, 5664, (1964).

Intermediates of the formula (IX) are novel and form an aspect of the invention.

It will be appreciated that the invention provides a process for the preparation of a compound of formula (I) which process comprises the deprotection of a compound of formula (I) wherein any OH groups in $R_1$, $R_2$ and/or $R_3$ are in protected form.

Preferred methods for deprotection, as hereinbefore described are hydrogenation of benzyl protecting groups (when $R_4$ is other than hydrogen), DDQ removal of p-methoxybenzyl protecting groups, removal of the t-Butyldimethylsilyl group and (where appropriate) oxidation of a compound wherein OH groups on adjacent carbon atoms are replaced by a bond.

The compounds of the invention are useful in the treatment of infections caused by viruses, especially herpes viruses such as herpes simplex type 1, herpes simplex type 2; varicella zoster viruses; and also lentiviruses such as visna virus.

Compounds of the invention may be formulated for use in a pharmaceutical composition. Accordingly, in a further aspect of the invention, there is provided a pharmaceutical composition which comprises a compound of formula (I) or pharmaceutically acceptable salt thereof together with a pharmaceutically acceptable carrier or excipient.

A composition which may be administered by the oral route to humans may be compounded in the form of a syrup, tablet or capsule. When the composition is in the form of a tablet, any pharmaceutical carrier suitable for formulating such solid compositions may be used, for example magnesium stearate, starch, lactose, glucose, rice, flour and chalk. The composition may also be in the form of an ingestible capsule, for example of gelatin, to contain the compound, or in the form of a syrup, a solution or a suspension. Suitable liquid pharmaceutical carriers include ethyl alcohol, glycerine, saline and water to which flavouring or colouring agents may be added to form syrups. The compounds may also be presented with a sterile liquid carrier for injection.

The composition may also be formulated for topical application to the skin or eyes.

For topical application to the skin, the composition may be in the form of a cream, lotion or ointment. These formulations may be conventional formulations well known in the art, for example, as described in standard books of pharmaceutics and cosmetics, such as Harry's Cosmeticology published by Leonard Hill Books and the British Pharmacopaeia.

The composition for application to the eyes may be a conventional eye-drop composition well known in the art, or an ointment composition.

Preferably, the composition of this invention is in unit dosage form or in some other form that may be administered in a single dose. A suitable dosage unit might contain from 50 mg to 1 g of active ingredient, for example 100 to 500 mg.

Such doses may be administered 1 to 4 times a day or more usually 2 or 3 times a day. The effective dose of compound will in general be in the range of from 1.0 to 20 mg/kg of body weight per day or more usually 2.0 to 10 mg/kg per day.

No toxicological effects are indicated at the above described dosage levels.

The invention also provides a method of treating viral infections in a human or non-human animal, which comprises administering to the animal an effective, non-toxic amount of a compound of formula (I) or a pharmaceutically acceptable salt thereof.

The invention also provides a compound of formula (I) or a pharmaceutically acceptable salt thereof for use as an active therapeutic substance, in particular for the treatment of viral infections.

The compounds of the invention also exhibit a synergistic antiviral effect in conjunction with interferons; and combination products comprising these two components for sequential or concomitant administration, by the same or different routes, are therefore within the ambit of the present invention.

The following examples illustrate the invention; the following descriptions illustrate the preparation of intermediates. The intermediates of Descriptions 10(f), 11 and 12 are also examples of active compounds of the invention.

Description 1 (Intermediates for Example 1, Method A)

(a) N-(3-Benzyloxyprop-1-oxy)phthalimide

Diethyl azodicarboxylate (15.6 ml 99.4 mmol) added to a solution of 3-benzyloxy-1-propanol (15 g, 90.4 mmol), N-hydroxyphthalimide (14.7 g, 90.1 mmol) and triphenylphosphine (23.7 g, 90.4 mmol) in tetrahydrofuran (450 ml). After 16 hours at 20° C. the solvent was removed under reduced pressure and the residue chromatographed on silica gel (eluted with hexane:acetone, 3:1) to yield the title compound as a yellow oil (27.8 g, 99%).

$^1$H NMR: $\delta_H$ (CDCl$_3$) 2.05 (2H, quintet, J=6 Hz, CH$_2$CH$_2$CH$_2$), 3.70 (2H, t, J=6 Hz, CH$_2$OCH$_2$Ph), 4.35 (2H, t, J=6 Hz, CH$_2$ON), 4.50 (2H, s, CH$_2$Ph), 7.35 (5H, s, CH$_2$Ph), 7.85 (4H, s, phthalimide protons).

(b) 3-Benzyloxyprop-1-oxyamine hydrochloride

A solution of N-(3-benzyloxyprop-1-oxy)phthalimide (27 g, 86.8 mmol) and hydrazine hydrate (4.2 ml, 86.8 mmol) in ethanol (200 ml) was heated at reflux temperature for 1 hour, cooled and then added to 3% sodium carbonate solution (500 ml). The aqueous solution was extracted with ether, the combined ether extracts were dried (magnesium sulphate), and evaporated to a syrup. Ethereal hydrogen chloride was added and the white solid obtained was separated by filtration, washed with ether and dried, yielding the title compound (15.2 g, 81%).

$^1$H NMR: $\delta_H$ [(CD$_3$)$_2$SO] 1.80 (2H, quintet, J=6 Hz, CH$_2$CH$_2$CH$_2$), 3.50 (2H, t, J=6 Hz, CH$_2$OCH$_2$Ph), 4.10 (2H, t, J=6 Hz, CH$_2$ON), 4.40 (2H, s, CH$_2$Ph), 7.30 (5H, s, Ar), 11.20 (3H, br.s, NH$_3$+).

(c) 5-Amino-1-(3-benzyloxyprop-1-oxy)-4-carboxamidoimidazole

A mixture of 3-benzyloxyprop-1-oxyamine hydrochloride (11.1 g, 51.0 mmol), ethyl N-(carbamoylcyano)methylformimidate (8.8 g, 70.3 mmol), ether (300 ml) and methanol (200 ml) was stirred at 20° C. for 24 hours. The ether was removed under reduced pressure and the methanolic solution boiled under reflux for 16 hours. The residue obtained on removal of the methanol was chromatographed on silica gel (eluted with chloroform then chloroform-ethanol, 19:1). Recrystallisation from acetone-petroleum ether (b.p. 60°–80° C.) gave the title compound (2.2 g, 15%), m.p. 139°–141° C.

UV: $\lambda_{max}$ (EtOH) 264 ($\epsilon$13,400)nm. IR: $\nu_{max}$ 3380, 3330, 3270, 3210, 3100, 1670, 1635, 1555, 1495, 1465, 1420 cm$^{-1}$. $^1$H NMR: $\delta_H$ [(CD$_3$)$_2$SO] 1.98 (2H, quintet, J=6.3, 6.6 Hz, CH$_2$CH$_2$CH$_2$), 3.59 (2H, t, J=6.3 Hz CH$_2$OCH$_2$Ph), 4.22 (2H, t, J=6.6 Hz, CH$_2$ON), 4.49 (2H, S, CH$_2$Ph), 5.81 (2H, br.s, CNH$_2$), 6.71 (2H, br.s, CONH$_2$), 7.34 (6H, m, Ph, H-2). Found: C, 58.02; H, 6.31; N, 19.33%; m/e, 290.1378. C$_{14}$H$_{18}$N$_4$O$_3$ requires: C, 57.91; H, 6.26; N, 19.30%; m/e, 290.1379.

(d) 5-(N'-Benzoylthiocarbamoyl)amino-1-(3-benzyloxyprop-1-oxy)imidazole-4-carboxamide Benzoylisothiocyanate (1.0 ml, 7.6 mmol) in acetone (100 ml) was added to a solution of 5-amino-1-(3-benzyloxyprop-1-oxy)imidazole-4-carboxamide (2.0 g, 6.9 mmol) in hot acetone (200 ml). The solution was boiled under reflux for 6 hours, cooled, evaporated under reduced pressure, and the residue chromatographed on silica gel (eluted with chloroform and then chloroform-ethanol, 30:1), yielding the title compound (3.0 g, 96%), IR: $\nu_{max}$ (KBr) 3470, 3300, 3130, 1670, 1610, 1535, 1495 cm$^{-1}$. $^1$H NMR: $\delta_H$ [(CD$_3$)$_2$SO] 1.93 (2H, quintet, J=6.3 Hz, CH$_2$CH$_2$CH$_2$), 3.54 (2H, t, J=6.3 Hz, CH$_2$OCH$_2$Ph), 4.39 (4H, m, CH$_2$ON, CH$_2$Ph), 7.12

(1H, CONH), 7.25 (6H, m, PhCH₂, CONH), 7.54 (2H, t, 2 protons of PhCO), 7.68 (1H, t, 1 proton of PhCO), 8.10 (3H, m, H-2, 2 protons of PhCO), 11.95 (2H, br.s, 2 × NH).

(e) 5-(N'-Benzoyl-S-methylthiocarbamoyl)amino-1-(3-benzyloxyprop-1-oxy)imidazole-4-carboxamide A mixture of 5-(N'-benzoylthiocarbamoyl)amino-1-(3-benzyloxyprop-1-oxy)imidazole-4-carboxamide (2.9 g, 6.4 mmol), 0.1N sodium hydroxide solution (100 ml) and methyl iodide (0.64 ml; 10.3 mmol) was stirred at 20° C. for 16 hours and then the solution adjusted to pH 5 with glacial acetic acid. After several extractions with chloroform, the combined extracts were dried (magnesium sulphate) and evaporated to a syrup. Column chromatography on silica gel (eluted with chloroform-ethanol, 30:1) afforded the title compound (2.7 g, 88.7%).

IR: $\nu_{max}$ (KBr) 3460, 3300, 3200, 3160, 1675, 1650, 1635, 1595, 1540, 1520, 1490, 1415 cm$^{-1}$. $^1$H NMR: $\delta_H$ [(CD₃)₂SO] 2.10 (2H, quintet, J=6.3 Hz, CH₂CH₂CH₂), 2.50 (3H, s, SCH₃), 3.70 (2H, t, J=6.3 Hz, CH₂OCH₂Ph), 4.40 (2H, t, J=6.3 Hz, CH₂ON), 4.55 (2H, s, CH₂Ph), 7.50 (11H, CH₂Ph, 3 protons of COPh, H-2, CONH₂), 8.00 (2H, m, 2 protons of COPh), 11.75 (1H, br.s, HN—C=N).

(f) 9-(3-Benzyloxyprop-1-oxy)guanine 5-(N,-Benzoyl-S-methylthiocarbamoyl)amino-1-(3-benzyloxyprop-1-oxy)imidazole-4-carboxamide (0.76 g, 1.63 mmol) was treated with 2% ammonia in dimethylformamide (35 ml) at 120° C. in a steel bomb for 6 hours. The solvent was removed under reduced pressure to yield a syrup, which was then dissolved in sodium hydroxide and heated at 100° C. for 3 hours. The cooled reaction mixture was acidified to pH 5 with concentrated hydrochloric acid. The precipitate obtained was collected, washed with several portions of ether and recrystallised from aqueous methanol, affording 9-(3-benzyloxyprop-1-oxy)guanine as white crystals (120 mg, 25%).

IR: $\nu_{max}$ (KBr) 3340, 3180, 2680, 1695, 1640, 1595, 1475 cm$^{-1}$. $^1$H NMR: $\delta_H$ [(CD₃)₂SO] 1.93 (2H, quintet, J=6.3, 6.6 Hz, CH₂CH₂CH₂), 3.58 (2H, t, J=6.3 Hz, CH₂OCH₂Ph), 4.33 (2H, t, J=6.6 Hz, CH₂ON), 4.48 (2H, s, CH₂Ph), 6.61 (2H, br.s, NH₂), 7.33 (5H, m, Ar), 7.91 (1H, s, H-8), 10.67 (1H, ar s, H-1). Found: C, 57.08; H, 5.41; N, 22.25%. C₁₅H₁₇N₅O₃ requires C, 57.12; H, 5.44; N, 22.21%.

Description 2 (Intermediates for Example 1, Method B and Examples 2 to 4)

(a) 4,6-Dichloro-2,5-diformamidopyrimidine

Acetic anhydride (40 ml) was added dropwise over 10 minutes to a mixture of 2,5-diamino-4,6-dichloropyrimidine (8.0 g, 44.7 mmol) and formic acid (100 ml) at 0° C. The mixture was stirred at 20° C. for 4 hours, evaporated to dryness and co-evaporated with toluene. Solidification from acetone-hexane afforded the title compound (6.1 g, 60%). IR: $\nu_{max}$ (KBr) 3230, 1715, 1680, 1575, 1550, 1485, 1415 cm$^{-1}$. Found m/e 233.9695; C₆H₄N₄O₂Cl₂ requires 233.9709.

(b) 6-(3-Benzyloxyprop-1-oxyamino)-4-chloro-2,5-diformamidopyrimidine

A mixture of 4,6-dichloro-2,5-diformamidopyrimidine (5.4 g, 23.0 mmol), 3-benzyloxyprop-1-oxyamine (4.14, 23.0 mmol), triethylamine (10 ml) and dioxan (50 ml) was stirred at reflux temperature for 3 hours, cooled, filtered and evaporated to dryness. Column chromatography on silica gel (eluted with chloroform-ethanol, 25:1) gave the title compound (4.38 g, 50%).

IR: $\nu_{max}$ (KBr) 3248, 1692, 1589, 1570, 1473, 1420 cm$^{-1}$. $^1$H NMR: $\delta_H$ [(CD₃)₂SO] 1.88 (2H, quintet, J=6.3 Hz, CH₂CH₂CH₂) 3.57 (2H, t, J=6.3 Hz, CH₂OCH₂Ph), 3.95 (2H, t, 6.3 Hz, CH₂ONH), 4.47 (2H, s, CH₂Ph), 7.32 (5H, m, Ph), 8.14 (1H, s, CHONH), 9.26 (1H, s, CHONH), 9.42 (1H, br.s, D₂O exchangeable, NHOCH₂), 10.83 (2H, br.s, 2×NHCHO).

(c) 9(3-Benzyloxyprop-1-oxy)-6-chloro-2-formamidopurine 6-(3-Benzyloxyprop-1-oxyamino)-4-chloro-2,5-diformamido pyrimidine (4.3 g, 11.3 mmol) in diethoxymethyl acetate (40 ml) was heated at 120° C. for 2.5 hours. The mixture was then cooled and evaporated to a syrup. The residue was dissolved in methanol (40 ml) and concentrated aqueous ammonia (5 ml). The solution was then stirred for 30 minutes at 20° C., evaporated under reduced pressure and the residue co-evaporated with methanol. Column chromatography on silica gel (eluted with chloroform-methanol, 50:1) gave the title compound (3.93 g, 95%) IR: $\nu_{max}$ 3120, 3080, 1700, 1615, 1580, 1500, 1435 cm$^{-1}$. $^1$H NMR: $\delta_H$ (CDC₃) 2.15 (2H, quintet, J=6 Hz, CH₂CH₂CH₂), 3.75 (2H, t, J=6 Hz, CH₂OCH₂Ph), 4.55 (4H, m, CH₂ON, CH₂Ph), 7.40 (5H, m, Ph), 8.10 (1H, s, H-8), 8.40 (1H, d, J=10 Hz, D₂O exchangeable, NHCHO), 9.60 (1H, d, J=10 Hz, NHCHO).

(d) 2-Amino-9-(3-benzyloxyprop-1-oxy)-6-ethoxypurine

A solution of 9-(3-benzyloxyprop-1-oxy)-6-chloro-2-formamidopurine (500 mg, 1.38 mmol) in 0.4M sodium ethoxide in ethanol (10 ml) was heated at 80° C. for 2.5 hours. The mixture was then cooled and evaporated under reduced pressure. The residue was dissolved in water (20 ml) and the solution was brought to pH 7 with dilute hydrochloric acid. The aqueous solution was extracted with chloroform (2×20 ml) and the combined extracts were washed with water (10 ml), dried (magnesium sulphate) and evaporated under reduced pressure. Column chromatography on silica gel (eluted with chloroform-ethanol, 50:1) yielded the title compound (390 mg, 8%). IR: $\nu_{max}$ (KBr) 3353, 3217, 1652, 1611, 1579, 1506, 1461, 1445, 1407 cm$^{-1}$. $^1$H NMR: $\delta_H$ [(CD₃)₂SO] 1.35 (3H, t, J=7.2 Hz, CH₃CH₂O), 1.95 (2H, quintet, J=6.3, 6.6 Hz, CH₂CH₂CH₂), 3.60 (2H, t, 6.3 Hz), 4.37 (2H, t, J=6.6 Hz, CH₂ON), 4.42 (2H, quartet, J=7.2 Hz, CH₃CH₂O), 4.48 (2H, s, CH₂Ph), 6.55 (2H, br.s, D₂O exchangeable, NH₂), 7.33 (5H, m, Ph), 8.07 (1H, s, H-8).

Description 3 (Intermediates for Example 5)

(a) 6-(3-Benzyloxy-2-benzyloxymethylprop-1-oxyamino)-4-chloro-2.5-diformamidopyrimidine A mixture of 4,6-dichloro-2,5-diformamidopyrimidine (from Description 1a) (3.3 g, 14.0 mmol), 3-benzyloxy-2-benzyloxymethylprop-1-oxyamine (4.2 g, 14.0 mmol), triethylamine (5.8 ml, 41.6 mmol) and dioxan (100 ml) was stirred at 100° C. for 2.5 hours. The cooled reaction mixture was filtered and the precipitate collected and washed with dioxan (2×25 ml). The filtrate and washings were combined and evaporated to a syrup. Column chromatography on silica gel (eluted with chloroform-ethanol, 50:1) afforded the title compound (4.9 g, 70%). IR: $\nu_{max}$ (KBr) 3240, 2910, 2860, 1690, 1585, 1565, 1475, 1420 cm$^{-1}$. $^1$H NMR: $\delta_H$ [(CD₃)₂SO] 2.29 (1H, quintet, J=6.0, 5.6 Hz, CH), 3.56 (4H, d, J=5.6 Hz, 2×CH₂OCH₂Ph), 3.94 (2H, d, J=6.0 Hz, CH₂ON) 4.46 (4H, s, 2×CH₂Ph), 7.30 (10H, m, 2×Ph), 9.28 (1H, br.s, NCHO), 9.42 (1H, br.s, NCHO), 10.86 (2H, br.s, D₂O exchangeable, 2×NHCHO).

(b) 9-(3-Benzyloxy-2-benzyloxymethylprop-1-oxy)-6-chloro-2-formamidopurine 6-(3-Benzyloxy-2-benzyloxymethylprop-1-oxyamino)-4-chloro-2,5-diformamidopyrimidine (4.8 g, 9.6 mmol) and diethoxymethyl acetate (50 ml) was stirred at 120° C. for 1.5 hours, cooled and evaporated under reduced pressure. The residue in methanol (80 ml) and concentrated ammonia solution (2 ml) was stirred at 20° C. for 30 minutes, the solvent removed under reduced pressure and the residue co-evaporated with methanol. Column chromatography on silica gel (eluted with chloroform and then chloroform-ethanol, 50:1) afforded the title compound (4.11 g, 89%). IR: $\nu_{max}$ (KBr) 3110, 2900, 2860, 1700, 1610, 1575, 1500, 1440 cm$^{-1}$. $^1$H NMR: δH [(CD₃)₂SO] 2.40 (1H, quintet, J=6.1, 6.7 Hz, CH), 3.64 (4H, J=6.7 Hz, 2×CH₂OCH₂Ph), 4.50 (6H, m, CH₂ON, 2×CH₂Ph), 7.30 (10H, m, 2×CH₂Ph), 9.36 (1H, s, OCHNH), 11.31 (1H, s, NHCHO). Found: C, 59.44; H, 5.09; N, 13.62%. C₂₄H₂₄N₅O₄Cl.0.5EtOH requires: C, 59.45; H, 5.40; N, 13.87%.

Description 4 (Intermediates for Examples 6, 7 and 26)

(a) 4-Allyloxyamino-6-chloro-2,5-diformamidopyrimidine

A mixture of 4,6-dichloro-2,5-diformamidopyrimidine (3.75 g, 16 mmol), O-allylhydroxylamine hydrochloride (1.8 g, 16.4 mmol) and triethylamine (9.1 ml, 66 mmol) in dioxan (80 ml) was stirred at 100° C. for 6 hours. The cooled reaction mixture was filtered and evaporated to dryness under reduced pressure. The residue was on silica gel (eluted with chloroform chromatographed methanol, 10:1) and the product recrystallised from chloroform-methanol affording the title compound (2.1 g, 48%), m.p. 170°-181° C. IR: $\nu_{max}$ (KBr) 3240, 1705, 1650, 1590, 1570, 1495, 1465, 1420 cm$^{-1}$. $^1$H NMR: δH [(CD₃)₂SO] 4.37 (2H, d, J=6 Hz, CH₂ON), 5.28 (2H, m, CH=CH₂), 6.00 (1H, m, CH=CH₂), 8.17 (1H, s, CHO), 9.30 (1H, s, CHO), 9.45 (1H, br.s, NH), 10.87 (2H, br.s, 2×NH). Found: C, 39.64; H, 3.49; N, 25.34%, M+ 271.0469. C₉H₁₀ClN₅O₃ requires C, 39.79; H, 3.71; N, 25.78%, M+ 271.0469.

(b) 9-Allyloxy-2-amino-6-chloropurine

A solution of 4-allyloxyamino-6-chloro-2.5-diformamido pyrimidine (1.23 g, 4.53 mmol) in diethoxymethyl acetate (20 ml) was stirred at 120° C. for 4 hours. The reaction was cooled and evaporated to dryness under reduced pressure. The residue was dissolved in methanol (5 ml) containing 0.88 ammonia (10 ml) and stirred at 25° C. for 16 hours. The solvents were evaporated under reduced pressure and the residue chromatographed on silica gel (eluted with ethyl acetate hexane 1:1) yielding the title compound (520 mg, 51%), m.p. 137°-9° C. UV: λ$_{max}$ (MeOH) 224 (ε 25,700). 247 (ε 5,300), 309 (ε 7.400) nm. IR: $\nu_{max}$ (KBr) 3480, 3400. 3310, 3200, 1635, 1615, 1560, 1510, 1465 cm$^{-1}$. $^1$H NMR δH [(CD₃)₂SO] 4.84 (2H, d, J=6 Hz, CH₂ON), 5.35 (2H, m, CH₂=CH), 6.13 (1H, m, CH=CH₂), 7.10 (2H, br.s, NH₂), 8.35 (1H, s, H-8). Found: C, 42.45; H, 3.63; N, 30.39%; M+ 225.0406. C₈H₈Cl N₅O requires C, 42.58; H, 3.57; N, 31.04%; M+ 225.0414.

(c) 2-Amino-6-chloro-9-(2,3-dihydroxyprop-1-oxy) purine

A solution of 9-allyloxy-2-amino-6-chloropurine (374 mg, 1.66 mmol) and osmium tetroxide (catalytic) in acetone (10 ml) and water (10 ml) was treated with 4-methylmorpholine N-oxide (290 mg, 2.49 mmol) and stirred under nitrogen at 25° C. for 16 hours. The reaction was evaporated to dryness under reduced pressure and the residue chromatographed on silica gel (eluted with acetone) affording the title compound (325 mg, 76%), m.p. 173°-5° C. UV: λ$_{max}$ (MeOH) 224 (ε 26,400), 310 (ε 7,600) nm. IR: $\nu_{max}$ (KBr) 3500, 3410, 3330, 3200, 3100, 1645, 1630, 1615, 1560, 1520, 1470 cm$^{-1}$. $^1$H NMR: δH [(CD₃)₂SO] 3.42 (2H, m, CH₂OH), 3.78 (1H, m, CHOH), 4.20 (1H, dd, J=10.7, 7.3 Hz, CH₂ON), 4.41 (1H, dd, J=10.7, 3.2 Hz, CH₂ON), 4.74 (1H, t, J=5.7 Hz, OH), 5.14 (1H, d, J=5.2 Hz), 7.13 (2H, br.s, NH₂), 8.36 (1H, s, H-8). Found: C, 36.41; H. 3.91, N, 25.91%, M+ 259.0462. C₈H₁₀ClN₅O₃.0.3H₂O requires C, 36.18; H, 4.04; N, 26.35%, M+ 259.0469.

Description 5 (Intermediates for Examples 8 and 9)

(a) 1,4-Bis(4-methoxybenzyloxy)but-2-ene

To a solution of 2-buten-1,4-diol (4.9 g, 60 mmol) in dry dimethylformamide (120 ml) was added sodium hydride (60% dispersion in oil; 5.28 g, 132 mmol) and the mixture was stirred at room temperature for 100 minutes. To this solution was added 4-methoxybenzyl chloride (17.9 ml, 132 mmol) in dimethylformamide (30 ml) dropwise over 45 minutes and the mixture was stirred for a further 40 minutes. The mixture was partitioned between ether (150 ml) and water (150 ml). The organic layer was further washed with water (150 ml), dried (magnesium sulphate) and the solvent was removed. The residue was purified by column chromatography on silica gel eluting with hexane-acetone (4:1, 3:1) to afford 1,4-bis(4-methoxybenzyloxy)but-2-ene as a clear colourless liquid (13.7 g, 70%). IR: $\nu_{max}$ (film) 2840, 1615, 1515 and 1250 cm$^{-1}$. $^1$H NMR: δH (CDCl₃) 3.80 (6H, s, 2×CH₃), 4.02 (4H, d, J=4.5 Hz, 2×CHCH₂), 4.43 (4H, s, 2×ArCH₂), 5.79 (2H, t, J=4.5 Hz, 2×CH), 6.88 (4H, d, J=9 Hz, ArH) and 7.27 (4H, d, J=9 Hz, ArH).

(b) 1,4-Bis(4-methoxybenzyloxy)butan-2-ol

To a solution of mercury (II) trifluoroacetate (17.1 g, 40 ml) in aqueous tetrahydrofuran (1:1, 80 ml) was added a solution of 1,4-bis(4-methoxybenzyloxy)but-2-ene (12.8 g, 39 mmol) in tetrahydrofuran (10 ml) over 5 minutes. The resulting 2-phase mixture was stirred vigorously at room temperature for 15 minutes. To the mixture was added aqueous sodium hydroxide (40 ml, 3M) followed by sodium borohydride (0.5M solution in 3M sodium hydroxide; 40 ml) with water-bath cooling. The solution was saturated with sodium chloride and allowed to stand. The organic layer was collected, dried (magnesium sulphate) and filtered through celite. The solvent was removed to afford 1,4-bis(4-methoxybenzyloxy)butan-2-ol (12.27 g, 91%), IR: $\nu_{max}$ (KBr) 3440, 2940, 2860, 1610, 1510 and 1250 cm$^{-1}$; $^1$H NMR: δH (CDCl₃) 1.76 (2H, q, J=6.0 Hz, 3-H), 2.90 (1H, br, D₂O exchangeable, OH), 3.41 (2H, AB of ABX $J_{AX}$=6.9 Hz, $J_{BX}$=4.2 Hz and $J_{AB}$=9.5 Hz, 1-H), 3.62 (2H, m, 4-H), 3.80 (6H, s, 2×CH₃), 4.00 (1H, m, 2-H), 4.43 (2H, s, ArCH₂), 4.48 (2H, s, ArCH₂), 6.86 (4H, m, ArH) and 7.24 (4H, m, ArH).

(c) N-[1,4-Bis(4-methoxybenzyloxy)but-2-oxy]phthalimide

To a solution of 1,4-bis(4-methoxybenzyloxybutan-2-ol (12.12 g, 35 mmol), triphenylphosphine (14.7 g, 56 mmol) and N-hydroxyphthalimide (9.14 g, 56 mmol) in dry tetrahydrofuran (140 ml) Was added diethyl azodicarboxylate (8.82 ml, 56 mmol). The solution became hot and took on a dark red colour. After stirring for 22 hours, N-hydroxyphthalimide (1.63 g, 10 mmol), triphenylphosphine, (2.62 g, 10 mmol) and diethyl azodicarboxylate (1.57, 10 mmol) were added. After a further 2 hours the solvent was removed. The residue was purified by column chromatography on silica gel eluting with hexane-ethyl acetate (2:1, 7:5) to afford N-[1,4-bis (4-methoxybenzyloxy)but-2-oxy]phthalimide as a clear colourless oil (10.9 g, 63%). UV: $\lambda_{max}$ (EtOH) 222 ($\epsilon$ 45,700) and 274 ($\epsilon$ 3,590)nm. IR: $\upsilon_{max}$ (film) 2940, 2860, 1735, 1615, 1520 and 1250 cm$^{-1}$. $^1$H NMR: $\delta$H (CDCl$_3$) 2.04 (2H, m, 3-H), 3.7–3.8. (10H, m, 2×CH$_3$, 1-H and 4-H), 4.25–4.55 (4H, m, 2×ArCH$_2$), 4.60 (1H, m, 2-H), 6.7–7.3 (8H, m, 2×CH$_3$OC$_6$H$_4$CH$_2$) and 7.73 (4H, m, phthalyl-H).

(d) 1,4-Bis(4-methoxybenzyloxy)but-2-oxyamine

To a solution of N-[1,4-bis(4-methoxybenzyloxy)but-2-oxy]phthalimide (10.3 g, 21 mmol) in dichloromethane (80 ml) was added methylhydrazine (1.49 ml, 28 mmol) and the solution was stirred at room temperature. After 20 minutes, further methylhydrazine (0.22 ml) was added. After a further 20 minutes the solution was filtered and the filtrate was extracted with aqueous sodium carbonate (3%). The organic layer was dried (magnesium sulphate) and the solvent removed. The residue was purified by column chromatography on silica gel eluting with hexane-ethyl acetate (1:1) to afford 1,4-bis(4-methoxybenzyloxy)but-2-oxyamine as a clear colourless oil (5.16 g, 68%). IR: $\upsilon_{max}$ (film) 2860, 1615, 1515 and 1250 cm$^{-1}$; $^1$H NMR: $\delta$H (CDCl$_3$) 1.80 (2H, m, 3-H), 3.54 (4H, m, 1-H and 4-H), 3.80 (6H, s, 2×CH$_3$), 3.86 (1H, m, 2-H), 4.42 (2H, s, ArCH$_2$), 4.48 (2H, s, ArCH$_2$), 5.37 (2H, s, D$_2$O exchangeable, NH$_2$), 6.87 (4H, m, Ar-H) and 7.25 (4H, m, Ar-H).

(e) 6-1,4-Bis(4-methoxybenzyloxy)but-2-oxyamino]-4-chloro-2,5-diformamidopyrimidine A solution of 4,6-dichloro-2,5-diformamidopyrimidine (3.27 g, 13.9 mmol), 1,4-bis(4-methoxybenzyloxy)-but-2-oxyamine (5.06 g, 14 mmol) and triethylamine (5.88 ml, 42 mmol) in dioxan (100 ml) was heated at 100° C. for 90 minutes. The solution was allowed to cool, filtered and the solvent removed. The residue was purified by column chromatography on silica gel eluting with chloroform-methanol (30:1) to afford 6-[1,4-bis (4-methoxybenzyloxy)but-2-oxyamino]-4-chloro-2,5-diformamidopyrimidine as a pale yellow foam. $^1$H NMR: $\delta$H (CDCl$_3$) 1.88 (2H, m, 3-H), 3.54 (4H, m, 1'-H and 4'-H), 3.73 (3H, s, CH$_3$), 3.74 (3H, s, CH$_3$), 4.07 (1H, m, 2'-H), 4.37 (4H, m, 2×ArCH$_2$), 6.88 (4H, m, ArH), 7.21 (4H, m, ArH), 9.17, 9.27, 9.30, 9.43 (total 2H, 4×s, D$_2$O exchange leaves s at 9.27, 2×HCO), 10.67 (1H, br.s, D$_2$O exchangeable, NH) and 10.85 (1H, br.s, D$_2$O exchangeable, NH).

(f) 9-[1,4-Bis(4-methoxybenzyloxy)but-2-oxy]-6-chloro-2-formamidopurine and 2-Amino-9-[1,4-Bis(4-methoxybenzyloxy)but-2-oxy]-6-chloropurine A solution of 6-[1,4-bis(4-methoxybenzyloxy)but-2-oxyamino)-2,5-diformamido-4-chloropyrimidine (4.71 g, 8.4 mmol) in diethoxymethyl acetate (45 ml) was heated at 120° C. for 1 hour. The solution was allowed to cool and the solvent was removed. The residue was taken up in methanol (60 ml) and concentrated aqueous ammonia (20 ml) and the solution was stirred at 50° C. for 1 hour and left at room temperature for 4 hours. The solvent was removed and the residue was purified by column chromatography on silica gel eluting with chloroform. Fractions 8–12 yielded 9-[1,4-bis(4-methoxybenzyloxy)but-2-oxy]-6-chloro-2-formamidopurine as a clear glass (0.66 g, 14.5%). $^1$H NMR: $\delta$H [(CD$_3$)$_2$SO] 2.00 (2H, m, 3'-H), 3.57–3.70 (4H, m, 1'-H and 4'-H), 3.73 (6H, s, 2×CH$_3$), 4.31 (2H, AB, J=11.4 Hz, ArCH$_2$), 4.39 (2H, s, ArCH$_2$), 4.71 (1H, m, 2'-H), 6.85 (4H, m, ArH), 7.06 (2H, d, J=8.8 Hz, ArH), 7.21 (2H, d, J=8.8 Hz, ArH), 8.61 (1H, s, 8-H), 9.33 (1H, s, HCO) and 11.27 (1H, s, D$_2$O exchangeable, 2-NH). Fractions 13–15 yielded a mixture of 2-formamido and 2-aminopurines (0.61 g, 14%). Fractions 16 and 17 yielded 2-amino-9-[1,4-bis(4-methoxybenzyloxy)but-2-oxy]-6-chloropurine as a clear glass. $^1$H NMR: $\delta$H [(CD$_3$)$_2$SO] 1.96 (2H, m, 3'-H), 3.46–3.65 (4H, m, 1'-H and 4'-H), 3.73 (6H, s, 2×CH$_3$), 4.33 (2H, AB, J=11.3 Hz, ArCH$_2$), 4.36 (2H, s, ArCH$_2$), 4.62 (1H, m, 2'-H), 6.86 (4H, m, ArH), 7.03 (2H, s, D$_2$O exchangeable, 2-NH$_2$), 7.11 (2H, d, J=8.5 Hz, ArH), 7.19 (2H, d, J=8.5 Hz, ArH) and 8.21 (1H, s, 8-H).

Description 6 (Intermediates for Example 1, Method A, alternative method to Description 1)

(a) N'-3-Benzyloxyprop-1-oxy-N,N-dimethylmethanimidamide

A solution of 3-benzyloxyprop-1-oxyamine (1.83 g, 10 mmol) in N,N-dimethylformamide dimethyl acetal (15 ml) was stirred at room temperature for 30 mins. The solvent was removed under reduced pressure and the residue dissolved in dichloromethane (30 ml) and washed with water (2×30 ml). The organic phase was dried (MgSO$_4$) and the solvent removed to give N-3-benzyloxyprop-1-oxy-N,N-dimethylmethanimidamide (2.1 g, 93%); IR: $\upsilon_{max}$ (film) 3090, 3060, 3030, 2930, 2860, 1630, 1495, 1480, 1450, 1440, 1410, 1390, 1380, 1365, 1320, 1250, 1205, 1105, 1075, 1065, 1030, 990, 950, 930, 910, 845, 740, 700 cm$^{-1}$; $^1$H NMR: $\delta$H (CDCl$_3$) 1.95 (2H, m, CH$_2$), 2.76 (6H, s, 2×CH$_3$), 3.57 (2H, t, J=6.5 Hz, CH$_2$), 3.95 (2H, t, J=6.5 Hz, CH$_2$), 4.51 (2H, s, CH$_2$), 7.3 (5H, m, C$_6$H$_5$), 7.61 (1H, s, CH); m/z 236 (M$^+$, 5%), 163 (5), 145 (25), 130 (20), 107 (35), 101 (5), 92 (10), 91 (100), 89 (15), 72 (15), 71 (50), 69 (15), 65 (15), 57 (15); M$^+$ observed 236.1527; C$_{13}$H$_{20}$ N$_2$O$_2$ requires M$^+$ 236.1524.

(b) 2-[N-(3-benzyloxyprop-1-oxy)iminomethyl]amino-2-cyanoacetamide

A solution of 2-amino-2-cyanoacetamide hydrochloride (5.38 g, 40 mmol) and N-3-benzyloxyprop-1-oxy-N,N-dimethylmethanimidamide (8.7 g, 39 mmol) in methanol (35 ml) was stirred at room temperature for 22 hours. The solvent was removed under reduced pressure and the residue treated with ethyl acetate (200 ml) and brine (1 ml). The ethyl acetate solution was decanted, the oily residue was washed with ethyl acetate (50 ml) and the combined organic phases were dried (MgSO$_4$). The solvent was removed under vacuum and the residual oil washed with hexane (3×50 ml), the hexane layer decanted and the residue dissolved in warm chloroform (40 ml) and treated with hexane (150 ml). The mixture was refrigerated at −18° C. for 1 hour, the organic phase decanted and the residual oil dried under reduced pressure to give 2-[N-(3-benzyloxyprop-1-oxy)iminomethyl]amino-2-cyanoacetamide (8 g, 70%); IR: $\upsilon_{max}$ (film) 3340, 3190, 3090, 3060, 3030, 2930, 2870, 2800, 1700, 1660, 1600, 1495, 1455, 1380, 1370, 1215, 1100, 1075, 1030, 980, 910, 860, 750, 700 cm$^{-1}$; $^1$H NMR: $\delta$H [(CD$_3$)$_2$SO] 1.86 (2H, m, CH$_2$), 3.53 (2H, m, CH$_2$), 3.84 (0.28H, t, J=6.5 Hz, CH$_2$), 3.94 (1.72H, t, J=6.5 Hz, CH$_2$), 4.46 (2H, s, CH$_2$), 5.06 (0.14H, d, J=8 Hz, CH), 5.23 (0.86H, d, J=8 Hz, CH), 6.76 (1H, d, J=10.5 Hz, CH), 6.95 (1H, dd, J=10.5 and 8 Hz, D$_2$O exchangeable NH), 7.2–7.4 (5H, m, C$_6$H$_5$), 7.95 (2H, br.s., D$_2$O exchangeable NH$_2$); m/z 290 (M+, 10%), 215 (3), 199 (5), 198 (10), 182 (5), 169 (5), 163 (10), 125 (10), 123 (10), 107 (35), 106 (10), 105 (10), 92 (15), 91 (100), 79 (10), 71 (10), 65 (10), 44 (15). Found: C, 54.06; H, 5.97; N, 17.64% M+ 290.1369. C$_{14}$H$_{17}$N$_4$O$_3$.1.15H$_2$O requires: C, 54.23; H, 6.27; N, 18.07%. M+ 290.1376.

(c) 5-Amino-1-(3-benzyloxyprop-1-oxy)-4-carboxamidoimidazole

To a solution of 2-[N-(3-benzyloxyprop-1-oxy)iminomethylamino-2-cyanoacetamide (2 g, 6.9 mmol) in dry dimethoxyethane (150 ml) under an atmosphere of dry nitrogen was added boron trifluoride etherate (0.85 ml, 6.9 mmol). The solution was heated at 60° C. for 1 hour, cooled to room temperature and the solvent removed under vacuum. The residue was partitioned between chloroform (100 ml) and sodium bicarbonate solution (100 ml). The aqueous phase was extracted with chloroform (30 ml), the combined organic phases dried (MgSO$_4$) and the solvent removed. The residue was chromatographed on silica, eluting with chloroform-methanol 20:1 to give 5-amino-1-(3-benzyloxyprop-1-oxy)-4-carboxamidoimidazole (1.25 g, 63%).

Description 7 Chiral Intermediates for Examples 14 and 15

(a) (S)-2-Methoxymethoxybutanedioic acid, bis dimethoxymethyl ester)

To a solution of (S)-2-hydroxybutanedioic acid (10 g, 75 mmol) in dry N,N-dimethylformamide (100 ml) was added diisopropylethylamine (29 ml, 165 mmol). The mixture was cooled to 0° C. and treated dropwise with a solution of chloromethyl methyl ether (13 ml, 165 mmol) in dry N,N-dimethylformamide. After stirring at room temperature for 18 hours, the solvent was removed and the residue treated with ethyl acetate (100 ml). The mixture was filtered and the precipitate washed with ethyl acetate (2×50 ml). The combined organic solutions were washed with brine (2×50 ml) and dried (MgSO$_4$). The solvent was removed under reduced pressure and the residual oil dissolved in dry dimethoxyethane (50 ml) and diisopropylethylamine (19.5 ml, 112 mmol) and treated dropwise with a solution of chloromethyl methyl ether (8.8 ml, 112 mmol) in dimethoxyethane (10 ml). The solution was heated at 80° C. for 2 hours, the solvent removed under reduced pressure and the residue dissolved in ethyl acetate (100 ml) and filtered. The filtrate was washed with brine (3×30 ml), dried (MgSO$_4$) and the solvent removed to leave a liquid which was distilled to give (S)-2-methoxymethoxybutanedioic acid, bismethoxymetyl ester (15 g, 75%), b.p. 116°-122° C. $[\alpha]_D^{25}$ −42.7° (c 1.3 in ethanol); IR: $\nu_{max}$ (film) 3000, 2880, 2900, 2830, 1745, 1470, 1450, 1440, 1410, 1370, 1275, 1210, 1150, 1115, 1095, 1030, 930 cm$^{-1}$; $^1$H NMR: δH (CDCl$_3$) 2.88 (2H, d, J=6.5 Hz, CH$_2$), 3.40 (1H, s, OCH$_3$), 3.48 (3H, s, OCH$_3$), 4.56 (1H, t, J=6.5 Hz, CH), 4.75 (2H, s, CH$_2$), 5.27 (2H, s, CH$_2$), 5.33 (2H, s, CH$_2$). Found: C, 45.23; H, 6.92%. C$_{10}$H$_{18}$O$_8$ requires C, 45.11; H, 6.82%.

(R)-2-Methoxymethoxybutanedioic acid, bismethoxymethyl ester

The (R)-isomer was prepared in an identical fashion from (R)-2-hydroxybutanedioic acid, and was obtained in 82% yield after chromatography on silica, eluting with ethyl acetate-hexane 1:2; $[\beta]_D^{25}$ +47.6° (c 1.1 in ethanol).

(S)-1,4-Dibenzyloxy-2-(methoxymethoxy)butane

A solution of (S)-2-methoxymethoxybutanedioic acid, bis methoxymethyl ester (10 g, 37.5 mmol) in dry tetrahydrofuran (10 ml) under dry nitrogen was treated with borane dimethylsulphide (8.3 ml, 83 mmol). The solution was heated between 60° C. and 80° C. over a period of 5.5 hours and then cooled in ice and treated dropwise with methanol (50 ml). After effervescence had ceased the solution was stirred at room temperature for 18 hours and the solvent removed under vacuum. The residue was evaporated to dryness with methanol (2×50 ml) and the residue chromatographed on silica, eluting with chloroform-methanol 5:1 to give (S)-1,4-dihydroxy-2-(methoxymethoxy)butane (3.9 g, 69%); IR: $\nu_{max}$ (film) 3400, 2940, 2890, 2820, 1470, 1440, 1410, 1380, 1300, 1210, 1150, 1100, 1030, 920 cm$^{-1}$; $^1$H NMR: δH (CDCl$_3$) 1.78 (2H, m, CH$_2$), 2.96 (2H, s, D$_2$O exchangeable OH's), 3.44 (3H, s, OCH$_3$), 3.5-3.85 (5H, m, CH plus 2×CH$_2$'s), 4.72 (1H, d, J=7 Hz, CH of CH$_2$), 4.77 (1H, d, J=7 Hz, CH of CH$_2$).

A 60% suspension of sodium hydride in oil (1.34 g, 33 mmol) was washed with hexane (2×20 ml) under an atmosphere of dry nitrogen. After decanting the hexane the solid was suspended in dry N,N-dimethylformamide (20 ml) and treated with a solution of (S)-1,4-dihydroxy-2-(methoxymethoxy)butane (2 g, 13 mmol) in N,N-dimethylformamide (5 ml). After stirring at room temperature for 6 hours the mixture was treated with a solution of benzyl bromide (3.9 ml, 33 mmol) in N,N-dimethylformamide (5 ml) and the mixture was stirred at room temperature overnight. The solvent was removed under reduced pressure and the residue partitioned between ethyl acetate (100 ml) and water (50 ml). The organic phase was washed with water (2×50 ml), dried with MgSO$_4$ and the solvent removed to give an oil which was chromatographed on silica eluting with ethyl acetate-hexane 1:2 to give (S)-1,4-dibenzyloxy-2-(methoxymethoxy)butane (3.6 g, 82%), $[\alpha]_D^{25}$ −16.0° (c 1.6 in ethanol); IR: $\nu_{max}$ (film) 3080, 3060, 3030, 2920, 2890, 2860, 1495, 1450, 1360, 1210, 1155, 1100, 1040, 920, 740, 700 cm$^{-1}$; $^1$H NMR: δH (CDCl$_3$) 1.90 (2H, m, CH$_2$), 3.35 (3H, s, OCH$_3$), 3.60 (4H, m, 2×CH$_2$), 3.90 (1H, m, CH), 4.50 (4H, m, 2×CH$_2$), 4.68 (1H, d, J=7 Hz, CH of CH$_2$), 4.74 (1H, d, J=7 Hz, CH of CH$_2$), 7.30 (10H, m, 2×C$_6$H$_5$); m/z (NH$_3$CI), MH+151, MNH$_4$+168.

(R)-1,4-Dibenzyloxy-2-(methoxymethoxy)butane

The (R)-isomer was prepared in an identical fashion from (R)-2-(methoxymethoxy)butanedioic acid, bis dimethoxymethyl ester and had $[\alpha]_D^{25}$ +16.8° (c 1.1 in ethanol).

(c) (S)-1,4-Dibenzyloxy-2-hydroxybutane

To a solution of (S)-1,4-dibenzyloxy-2-(methoxymethoxy)butane (2 g, 6 mmol) in methanol (14 ml) was added a 2% solution of methanolic hydrogen chloride (6 ml, 2.5 mmol). The solution was stirred at room temperature for 7 hours, the solvent removed and the residue chromatographed on silica eluting with ethyl acetate hexane 1:1 to give (S)-1,4-dibenzyloxy-2-hydroxybutane (1.46 g, 84%), $[\alpha]_D^{25}$ −7.3° (c 1.1 in ethanol); IR: $\nu_{max}$ (film) 3450, 3080, 3060, 3015, 2920, 2860, 2800, 1950, 1870, 1810, 1605, 1585, 1495, 1450, 1365, 1310, 1260, 1205, 1100, 1030, 1000, 950, 915, 820, 805, 760, 700, 610 cm$^{-1}$; $^1$H NMR: δH (CDCl$_3$) 1.79 (2H, d, t J=6 Hz and 6 Hz, CH$_2$), 2.86 (1H, d, J=3 Hz, D$_2$O exchangeable, OH), 3.45 (2H, m, CH$_2$), 3.65 (2H, m, CH$_2$), 4.05 (1H, m, CH), 4.51 (2H, s, CH$_2$), 4.55 (2H, s, CH$_2$), 7.3 (10H, m, 2×C$_6$H$_5$). Found: C, 75.64; H, 7.87%. C$_{18}$H$_{22}$O$_3$ requires: C, 75.50; H, 7.74%.

(R)-1,4-dibenzyloxy-2-hydroxybutane

The (R)-isomer was prepared in an identical fashion from (R)-1,4-dibenzyloxy-2-(methoxymethoxy)-butane and had $[\alpha]_D^{25} +7.7°$ (c 0.5 in ethanol).

Description 8 (Intermediates for Example 14)

(a) (R)-N-(1,4-Dibenzyloxybut-2-oxy)phthalimide

To a solution of (S)-1,4-dibenzyloxy-2-hydroxybutane (5 g, 17.5 mmol) in dry tetrahydrofuran (100 ml) was added triphenylphosphine (5.1 g, 19.2 mmol) and N-hydroxyphthalimide (3.1 g, 19.2 mmol). The solution was treated dropwise with diethyl azadicarboxylate (3 ml, 19.2 mmol). A red colouration appeared, gradually fading and the solution became warm. The solution was stirred at room temperature for 48 hours and the solvent removed under vacuum. The residue was dissolved in ethylacetatehexane 1:1 (100 ml) and refrigerated. A white solid crystallised out and was filtered off. The solution was evaporated to dryness and the residue chromatographed on silica, eluting with ethylacetate-hexane 1:2 to give (R)-N-(1,4-dibenzyloxybut-2-oxy)phthalimide (4.6 g, 61%), $[\alpha]_D^{25} +16.4°$ (c 1.3 in ethanol); IR: $\nu_{max}$ (film) 3090, 3060, 3030, 2930, 2860, 1810, 1790, 1730, 1610, 1495, 1465, 1450, 1370, 1240, 1190, 1120, 1100, 1080, 1030, 1015, 980, 880, 785, 740, 700 cm$^{-1}$; $^1$H NMR: $\delta$H (CDCl$_3$) 2.1 (2H, m, CH$_2$), 3.75 (4 H, m, 2×CH$_2$), 4.5 (5H, m, 2×CH$_2$ plus CH), 7.1–7.9 (14 H, m, 2×C$_6$H$_5$ plus C$_6$H$_4$); m/z (FAB) MH$^+$ 432.

(b) (R)-1,4-Dibenzyloxybut-2-oxyamine

A solution of (R)-N-(1,4-dibenzyloxybut-2-oxy)phthalimide (0.6 g, 1.3 mmol) in dichloromethane (5 ml) was treated with methylhydrazine (86 μl, 1.6 mmol). A deep red colouration developed, disappearing gradually as a white solid precipitated out of solution. After stirring at room temperature for 30 minutes additional methylhydrazine (8 μl, 0.15 mmol) was added. The mixture was stirred at room temperature for an additional 30 minutes, filtered and the filtrate washed with 3% sodium carbonate solution (5 ml). The organic phase was dried (MgSO$_4$), the solvent removed under reduced pressure and the residue chromatographed on silica eluting with ethyl acetate-hexane to give (R)-1,4-dibenzyloxybut-2-oxyamine (0.32 g, 77%), $[\alpha]_D^{25} +10.1°$ (c 0.14 in ethanol); IR: $\nu_{max}$ (film) 3310, 3250, 3090, 3060, 3030, 2920, 2860, 1585, 1495, 1450, 1365, 1310, 1200, 1100, 1030, 950, 915, 740, 700 cm$^{-1}$; $^1$H NMR: $\delta$H (CDCl$_3$) 1.85 (2H, m, CH$_2$), 3.55 (4H, m, 2×CH$_2$), 3.90 (1H, m, CH), 4.49 (2H, s, CH$_2$), 4.45 (2H, s, CH$_2$), 5.36 (2H, s, D$_2$O exchangeable NH$_2$) 7.35 (10H, m, 2×C$_6$H$_5$); m/z 302 (MH+), 301 (M+, 3%), 181 (5), 163 (10), 106 (15), 105 (5), 92 (15), 91 (100), 71 (15), 65 (10). M+ observed 301.1670; C$_{18}$H$_{23}$NO$_3$ requires M+ 301.1678.

(c) (R)-N'-1,4-Dibenzyloxybut-2-oxy-N,N-dimethylmethanimidamide

A solution of (R)-1,4-dibenzyloxybut-2-oxyamine (1.6 g. 5.3 mmol) in N,N-dimethylformamide dimethyl acetal (10 ml) was stirred at room temperature for 30 minutes. The solvent was removed and the residue dissolved in dichloromethane (50 ml) and washed with brine (2×20 ml). The organic phase was dried (MgSO$_4$), the solvent removed under reduced pressure and the residue chromatographed on silica, eluting with ethyl acetatehexane 1:2 to give, as an oil, (R)-N'-1,4-dibenzyloxybut-2-oxy-N,N-dimethylmethanimidamide (1.51 g, 77%), IR: $\nu_{max}$ (film) 3090, 3060, 3030, 3000, 2920, 2900, 2860, 1630, 1495, 1480, 1455, 1410, 1390, 1365, 1320, 1250, 1205, 1105, 1030, 990, 945, 925, 910, 740, 700 cm$^{-1}$; $^1$H NMR: $\delta$H (CDCl$_3$) 1.97 (2H, m, CH$_2$), 2.73 (6H, s, 2× CH$_3$), 3.60 (4H, m, 2×CH$_2$), 4.13 (1H, m, CH), 4.53 (4H, m, 2×CH$_2$), 7.3 (10H, m, 2×C$_6$H$_5$), 7.62 (1H, s, CH); m/z 356 (M+ <1%), 265, (5), 129 (5), 107 (30), 92 (15), 91 (100), 88 (15), 71 (20), 65 (15), 57 (5), 44 (20). Found: C, 71.81; H, 8.03; N, 7.95%; M+ 356.2107. C$_{21}$H$_{28}$N$_2$O$_3$ requires: C, 71.71; H, 7.66; N, 7.60%; M+ 356.2100.

(d) (R)-2-[N-(1,4-Dibenzyloxybut-2-oxy)iminomethyl]-amino-2-cyanoacetamide

A solution of 2-amino-2-cyanoacetamide hydrochloride (0.19 g, 1.4 mmol) and (R)-N'-(1,4-dibenzyloxybut-2-oxy)-N,N-dimethylmethanimidamide (0.5 g, 1.4 mmol) in methanol (1.5 ml) was stirred at room temperature for 20 hours. The solvent was removed under reduced pressure and the residue treated with ethyl acetate (20 ml) and brine (0.05 ml). The organic solution was decanted and dried (MgSO$_4$). The solvent was removed under reduced pressure and the residual oil extracted with hexane (3×10 ml). The hexane was decanted and the residual oil was dissolved in warm chloroform (3 ml) and treated with hexane (20 ml). After refrigeration (−18° C.) for 1 hour, the organic solution was decanted and the insoluble oil dried under vacuum to give (R)-2-[N-(1,4-dibenzyloxy-but-2-oxy)iminomethyl]amino-2-cyanoacetamide (0.37 g, 74%); IR: $\nu_{max}$ (film) 3340, 3190, 3090, 3060, 3030, 2950, 2920, 2860, 2800, 1700, 1660, 1600, 1495, 1455, 1375, 1310, 1240, 1215, 1145, 1125, 1025, 985, 945, 905, 740, 700 cm$^{-1}$; $^1$H NMR: $\delta$H [(CD$_3$)$_2$SO] 1.87 (2H, m, CH$_2$), 3.54 (4H, m, 2×CH$_2$), 4.05 (0.12H, m, CH), 4.13 (0.88H, m, CH), 4.45 (4H, m, 2×CH$_2$), 5.07 (0.13H, d, J=8 Hz, CH), 5.26 (0.87H, d, J=8 Hz, CH), 6.80 (1H, d, J=10.5 Hz, CH), 6.92 (1H, dd, J=10.5 and 8 Hz, NH), 7.2–7.8 (12H, m, 2×C$_6$H$_5$ plus D$_2$O exchangeable NH$_2$); m/z (NH$_3$Cl) M+ 411. Found: C, 61.83; H, 6.50; N, 13.32%. C$_{22}$H$_{26}$N$_4$O$_4$. H$_2$O requires: C, 61.67; H, 6.59; N, 13.08%.

(e) (R)-5-Amino-4-carboxamido-1-(1,4-dibenzyloxybut-2-oxy)-imidazole

To a solution of 2-[N-(1,4-dibenzyloxybut-2-oxy)iminomethyl]amino-2-cyanoacetamide (0.32 g, 0.8 mmol) in dry dimethoxyethane (25 ml) under an atmosphere of dry nitrogen was added boron trifluoride etherate (0.1 ml, 0.8 mmol). The solution was heated at 60° C. for 1 hour, cooled to room temperature and the solvent removed under vacuum. The residue was partitioned between chloroform (50 ml) and saturated sodium bicarbonate (50 ml). The aqueous phase was extracted with chloroform and the combined organic phases were washed with brine (30 ml) and dried (MgSO$_4$). The solvent was removed to leave an oil which was chromatographed on silica, eluting with chloroform-methanol 40:1 to give, as a gum, (R)-5-amino-4-carboxamido-1-(1,4-dibenzyloxybut-2-oxy)imidazole (0.19 g, 60%); IR: $\nu_{max}$ (film) 3450, 3320, 3180, 3100, 3070, 3030, 2930, 2870, 2880, 1650, 1635, 1570, 1500, 1465, 1455, 1420, 1370, 1315, 1255, 1210, 1175, 1100, 1030, 1010, 750, 700 cm$^{-1}$; $^1$H NMR: $\delta$H [(CD$_3$)$_2$SO] 2.04 (2H, m, CH$_2$), 3.63 (4H, m, 2×CH$_2$), 4.45 (5H, m, 2×CH$_2$ plus CH), 5.67 (2H, s, D$_2$O exchangeable NH$_2$), 6.75 (2H, br., D$_2$O exchangeable NH$_2$), 7.3 (11H, m, 2×C$_6$H$_5$ plus CH); m/z 410 (M+, 2%), 163 (5), 142 (10), 125 (5), 107 (10), 92 (10), 91 (100), 71 (10), 65 (10), 44 (5). Found: C, 64.70; H, 6.49; N, 13.15%; M+ 410.1962. C$_{22}$H$_{26}$N$_4$O$_4$ requires: C, 64.38; H, 6.39; N, 13.65%; M+ 410.1954.

(f) (R)-S-(N'-Benzoylthiocarbamoyl)amino-4-carboxamido-1-(1,4-dibenzyloxybut-2-oxy)imidazole To a solution of (R)-5-amino-4-carboxamido-1-(1,4-dibenzyloxybut-2-oxy)imidazole (0.8 g, 2 mmol) in dry acetone (60 ml) was added benzoylisothiocyanate (0.32 ml, 2.4 mmol). The solution was refluxed for 6 hours, cooled to room temperature and the solvent removed under reduced pressure. The residue was dissolved in chloroform (60 ml) and washed with water (30 ml) and the organic phase dried (MgSO$_4$). The solvent was removed under reduced pressure and the residue chromatographed on silica, eluting with chloroform-methanol 30:1 to give (R)-5-(N'-benzoylthiocarbamoyl)amino-4-carboxamido-1-(1,4-dibenzyloxybut-2-oxy)imidazole (1.04 g, 93%) as a glass; IR: $\upsilon_{max}$ (KBr) 3450, 3200, 3060, 3015, 2920, 2860, 1670, 1610, 1580, 1510, 1490, 1450, 1415, 1360, 1330, 1310, 1260, 1180, 1060, 1100, 1075, 1030, 1000, 740, 715, 700 cm$^{-1}$; $^1$H NMR: δH (CDCl$_3$) 1.95 (2H, m, CH$_2$), 3.60 (4H, m, 2×CH$_2$), 4.33 (2H, s, CH$_2$) 4.48 (2H, s, CH$_2$), 4.60 (1H, m, CH), 7.1–8.1 (18H, m, 3×C$_6$H$_5$, CH plus D$_2$O exchangeable NH$_2$), 12.00 (2H, s, D$_2$O exchangeable NH$_2$).

(g) (R)-5-(N'-Benzoyl-S-methylthiocarbamoyl)amino-4-carboxamido-1-(1,4-dibenzyloxybut-2-oxy)imidazole A solution of (R)-5-(N'-benzoylthiocarbamoyl)amino-4-carboxamido-1-(1,4-dibenzyloxybut-2-oxy)imidazole (0.4 g, 0.7 mmol) in 0.2N sodium hydroxide solution (10 ml) was cooled to 0° C. and treated with methyl iodide (0.22 ml, 3.5 mmol). The mixture was stirred at 0° C. for 1 hour and at room temperature for 2 hours, then neutralised by addition of acetic acid. The product was extracted into chloroform (50 ml), the organic phase dried (MgSO$_4$) and evaporated to dryness. The residue was chromatographed on silica, eluting with chloroformmethanol 30:1 to give as a glass, (R)-5-(N'-benzoyl-S-methylthiocarbamoyl)amino-4-carboxamido-1-(1,4-dibenzyloxybut-2-oxy)imidazole (0.3 g, 73%); IR: $\upsilon_{max}$ (film) 3466, 3330, 3164, 3118, 3088, 3063, 3030, 3006, 2928, 2863, 1674, 1610, 1581, 1540, 1496, 1479, 1454, 1411, 1350, 1321, 1308, 1296, 1270, 1206, 1179, 1148, 1097, 1061, 1028, 1010, 1001, 886, 875, 860, 788, 741, 722, 699 cm$^{-1}$; $^1$H NMR: δH [(CD$_3$)$_2$SO] 2.00 (2H, m, CH$_2$), 2.40 (3H, s, CH$_3$), 3.5–3.7 (4H, m, 2×CH$_2$ plus CH), 4.45 (4H, m, 2×CH$_2$), 4.62 (1H, m, CH), 7.2–7.8 (18H, m, 3×C$_6$H$_5$ CH plus D$_2$O exchangeable NH$_2$), 11.76 (1H, s, D$_2$O exchangeable NH).

(h) (R)-9-(1,4-Dibenzyloxybut-2-oxy)guanine

A mixture of (R)-5-(N'-benzoyl-S-methylthiocarbamoyl)amino-4-carboxamido-1-(1,4-dibenzyloxybut-2-oxy)imidazole (160 mg, 0.1 mmol) and 7M sodium hydroxide solution (9 ml) was heated to 100° C. and treated with dimethylsulphoxide (3 ml). The mixture was heated at 100° C. for 45 minutes, cooled and neutralised with 5M hydrochloric acid. The product was extracted into chloroform (50 ml) and the aqueous phase washed with chloroform (2×30 ml). The organic phase was dried (MgSO$_4$), the solvent removed under reduced pressure and the residue treated with water (100 ml) and extracted with chloroform (2×30 ml). The organic phase was dried (MgSO$_4$), the solvent removed and the residue chromatographed on silica, eluting chloroform-methanol 20:1 to give (R)-9-(1,4-dibenzyloxybut-2-oxy)guanine (50 mg, 42%) recrystallised from methanol, m.p. 214°–215° C. (dec); IR: $\upsilon_{max}$(KBr), 3450, 3320, 3160, 3030, 2920, 2360, 2740, 1695, 1650, 1630, 1600, 1585, 1540, 1500, 1475, 1465, 1390, 1365, 1330, 1250, 1205. 1160, 1100, 1070, 1030, 1010, 910, 870, 820, 780, 740, 700, 625 cm$^{-1}$; $^1$H NMR: δH [(CD$_3$)$_2$SO] 2.0 (2H, m, CH$_2$), 3.5–3.75 (4H, m, 2×CH$_2$), 4.4–4.65 (5H, m, 2×CH$_2$ plus CH), 6.50 (2H, s, D$_2$O exchangeable NH$_2$), 7.30 (10H, m, 2×C$_6$H$_5$), 7.77 (1H, s, CH), 10.65 (1H, s, D$_2$O exchangeable NH); m/z 435 (M$^+$<1%), 167 (10), 151 (10), 107 (30), 105 (10), 92 (15), 91 (100), 99 (10), 77 (10), 71 (10), 65 (15), 43 (10). Found: C, 63.12; H, 5.80; N, 15.71%. C$_{23}$H$_{25}$N$_5$O$_4$ requires C, 63.44; H, 5.79; N, 16.08%.

Description 9 (Intermediates for Example 15)

(a) (S)-N-(1,4-Dibenzyloxybut-2-oxy)phthalimide

To a solution of (R)-1,4-dibenzyloxy-2-hydroxybutane (8 g, 28 mmol) in dry tetrahydrofuran (150 ml) was added triphenylphosphine (11 g, 42 mmol) and N-hydroxyphthalimide (6.8 g, 42 mmol). The solution was treated dropwise with diethyl azodicarboxylate (6.6 ml, 42 mmol). A dark red colouration appeared, gradually fading and the solution became warm. The solution was stirred at room temperature for 16 hours, then treated with additional triphenyl phosphine (2.25 g, 8.5 mmol) N-hydroxyphthalimide (1.35 g, 8.5 mmol) and diethyl azodicarboxylate (1.35 ml, 8.5 mmol). After stirring for an additional 24 hours at room temperature, the solvent was removed under reduced pressure and the residue dissolved in ethyl acetate-hexane 1:1 (100 ml) and refrigerated. A white solid crystallised out and was filtered off. The solution was evaporated to dryness and the residue dissolved in ethyl acetate-hexane 1:1 (50 ml) and refrigerated. After filtration, the filtrate was evaporated to dryness and the residue chromatographed on silica, eluting with ethyl acetate-hexane 1:2 to give (S)-N-(1,4-dibenzyloxybut-2-oxy)phthalimide (11 g, (91%), $[\alpha]^{25}$ −17.4° (c 0.8 in ethanol); IR: $\upsilon_{max}$ D(film) 3087, 3065, 3031, 2930, 2863, 2804, 1809 1790, 1734, 1608, 1496, 1468, 1454, 1411, 1373, 1239, 1189, 1120, 1102, 1083, 1028, 1016, 981, 878, 786, 739, 699 cm$^{-1}$; $^1$H NMR: δH (CDCl$_3$) 2.05 (2H, m, CH$_2$), 3.75 (4H, m, 2×CH$_2$), 4.4–4.7 (5H, m, 2×CH$_2$ plus CH), 7.1–7.9 (14H, m, 2×C$_6$H$_5$ plus C$_6$H$_4$), m/z (FAB) MH$^+$432.

(b) (S)-1,4-Dibenzyloxybut-2-oxyamine

A solution of (S)-N-(1,4-dibenzyloxybut-2-oxy)phthalimide (5 g, 11.6 mmol) in dichloromethane (50 ml) was treated with methylhydrazine (0.8 ml, 15 mmol). A deep red colouration developed, disappearing gradually as a white solid precipitated out of solution. After stirring at room temperature for 1 hour, the solid was filtered off and the filtrate was washed with a 3% sodium carbonate solution. After drying (MgSO$_4$) the solution was evaporated to dryness and the residual oil was chromatographed on silica eluting with ethyl acetate-hexane 5:1 to give (S)-1,4-dibenzyloxybut-2-oxyamine (2.66 g, 76%), $[\alpha]_D^{25}$ −3.2° (c 0.3 in ethanol); IR: $\upsilon_{max}$ (film) 3315, 3248, 3087, 3062, 3030, 2922, 2861, 1588, 1496, 1454, 1365, 1205, 1101, 1028, 738, 698 cm$^{-1}$; $^1$H NMR: δH (CDCl$_3$) 1.85 (2H, m, CH$_2$), 3.55 (4H, m, 2×CH$_2$), 3.90 (1H, m, CH), 4.49 (2H, s, CH$_2$), 4.55 (2H, s, CH$_2$), 5.36 (2H, s, D$_2$O exchangeable NH$_2$), 7.30 (10H, m, 2×C$_6$H$_5$); m/z 302 (MH$^+$), 301 (M$^+$, 3%), 181 (5), 163 (10), 106 (15), 105 (5), 92 (15), 91 (100), 71 (15), 65 (10). Found: C, 71.40; H, 7.66, N, 4.61%, M$^+$ 301.1670. C$_{18}$H$_{23}$NO$_3$ requires: C, 71.73; H, 7.69, N, 4.65% M$^+$ 301.1678.

(c) (S)-4-Chloro-6-(1,4-dibenzyloxybut-2-oxyamino)-2,5-diformamidopyrimidine

A solution of (S)-N-1,4-dibenzyloxybut-2-oxyamine (2.17 g, 7.2 mmol), 4,6-dichloro-2,5-diformamidopyrimidine (1,7 g, 7.2 mmol) and triethylamine (3 ml, 2.4 mmol) in dioxan (50 ml) was heated at 100° C. for 1.5 hours. The mixture was cooled to room temperature, filtered and the solvent removed under reduced pressure. The residue was chromatographed on silica eluting with chloroform-methanol 30:1 to give as an oil, (S)-4-chloro-6-(1,4-dibenzyloxybut-2-oxyamino)-2,5-diformamidopyrimidine (2.59 g, 71%); IR: $\upsilon_{max}$ (film) 3241, 3062, 3031, 2924, 2863, 1695, 1635, 1587, 1567, 1496, 1477, 1454, 1417, 1388, 1365, 1248, 1207, 1094, 1028, 905, 803, 775, 739, 698 cm$^{-1}$; $^1$H NMR: δH [(CD$_3$)$_2$SO] 1.94 (2H, m, CH$_2$), 3.60 (4H, m, 2×CH$_2$), 4.13 (1H, m, CH), 4.47 (2H, m, 2×CH$_2$), 7.28 (10H, m, 2×C$_6$H$_5$), 7.85 and 8.14 (1H, m, CH), 9.16–9.41 (2H, m, CH plus D$_2$O exchange NH). Found: C, 57.67; H, 5.34; N, 13.40%. C$_{24}$H$_{26}$ClN$_5$O$_5$ requires C, 57.77; H, 5.05; N, 14.04%.

(d) (S)-6-Chloro-9-(1,4-dibenzyloxybut-2-oxy)-2-formamidopurine

A solution of (S)-4-chloro-6-(1,4-dibenzyloxybut-2-oxyalkamino)-2,5-diformanidopyrimidine (0.7 g, 1,4 mmol) in diethoxymethyl acetate (15 ml) was heated at 100° C. for 1.5 hours. The solvent was removed under reduced pressure and the residue dissolved in methanol (20 ml) and treated with 0.88 ammonia solution (0.5 ml). After stirring at room temperature for 30 minutes, the solvent was removed and the residue co-evaporated with methanol (3×20 ml). The residue was chromatographed on silica eluting with chloroform-methanol 60:1 to give, as an oil, (S)-6-chloro-9-(1,4-dibenzyloxybut-2-oxy)-2-formamidopurine (0.57 g, 84%); IR: $\upsilon_{max}$ (film) 3226, 3168, 3120, 3089, 3063, 3030, 3007, 2920, 2864, 1704, 1612, 1576, 1504, 1476, 1454, 1439, 1388, 1326, 1208, 1138, 1099, 1028, 1018, 995, 922, 862, 784, 739, 699, 655, 621, 608 cm$^{-1}$; $^1$H NMR: δH [(CD$_3$)$_2$SO] 2.04 (2H, m, CH$_2$), 3.55–3.8 (4H, m, 2×CH$_2$), 4.30–4.55 (4H, m, 2×CH$_2$), 4.76 (1H, m, CH), 7.05–7.4 (10H, m, 2×C$_6$H$_5$), 8.64 (1H, s, CH), 9.33 (1H, br.s, CH), 11.27 (1H, s, D$_2$O exchangeable NH).

Description 10 (Intermediates for Examples 16–19)

(a) 2-Hydroxymethyl-1,2-propanediol

2N Borane: dimethylsulphide complex in tetrahydrofuran (170.5 ml) was added to triethylmethanetricarboxylate (24.9 g 0.107 mol) under nitrogen. The reaction was heated under reflux and dimethylsulphide removed. After 8 hours the reaction was cooled, methanol (100 ml) added and the solution stirred for 15 hours. The solvent was removed under reduced pressure and the residue co-evaporated with methanol (3×50 ml). Column chromatography on silica gel (eluted with chloroform:methanol (3.1)) gave 2-hydroxymethyl-1,3-propanediol (9.43 g; 83%), m.p. 65°–68° C. IR:$\upsilon_{max}$ (KBr) 3267, 2944, 2801, 1489, 1479, 1113, 1058, 1006 cm$^{-1}$. $^1$H NMR: δ$_H$[(CD$_3$)$_2$SO] 1.60 (1H, septet, J=6 Hz,CH), 3.40(6H, t, J=6 Hz, 3×CH$_2$), 4.25 (3H, t, J=6 Hz, D$_2$O exchangeable, 3×OH). Found: C, 45.29; H, 9.77%. C$_4$H$_{10}$O$_3$ requires: C, 45.26; H, 9.52%.

(b) 2,2-Dimethyl-5-hydroxymethyl-1,3-dioxan

A mixture of 2-Hydroxymethyl-1,3-propanediol (9.0 g, 61.6 mmol), 2,2-dimethoxypropane (11.7 ml, 95.2 mmol) 4-toluenesulphonic acid monohydrate (0.49 g, 2.58 mmol) and tetrahydrofuran (450 ml) was stirred at 20° C. for 1 hour. Triethylamine (5 ml) was then added and the solvent removed under reduced pressure. Chromatography on silica gel (eluted with chloroform ethanol, 10.1) afforded the title compound (9.62 g, 78%) as a colourless oil. 1R: $\upsilon_{max}$ (film) 3431, 2993, 2943, 2874, 1482, 1456, 1373 cm$^{-1}$. $^1$H NMR: δ$_H$[(CD$_3$)$_2$SO] 1.30(6H, s, 2×CH$_3$), 1.69(1H,m,CH), 3.38(2H,dd, J=5.2, 6.6 Hz, CH$_2$OH), 3.61(2H,dd, J=11.8, 7.1 Hz, 2×H(ax)), 3.82 (2H, dd, J=11.8, 4.4 Hz, 2×H(eq)), 4.53(1H, t, J=5.2 Hz, D$_2$O exchangable, OH). Found: C, 56.73; H, 9.80%. C$_7$H$_{14}$O$_3$.0.01H$_2$O requires: C, 56.80; H, 9.69%.

(c) N-(2,2-Dimethyl-1,3-dioxan-5-ylmethoxy) phthalimide.

A mixture of 2.2-Dimethyl-5-hydroxymethyl-1,3-dioxan (9.60 g, 65.8 mmol), triphenylphosphine (20.74 g, 79.2 mmol), N-hydroxyphthalimide (12.90 g, 79.2 mmol), diethyl azodicarboxylate (12.45 ml, 79.2 mmol) and tetrahydrofuran (300 ml) was stirred at 20° C. for 16 hours. The solvent was then removed under reduced pressure, the residue triturated with ether, filtered and the filtrate evaporated. The process was repeated and then the residue was chromatographed on silica (eluted with hexane: acetone, 3:1; then hexane: acetone 5:2), affording the title compound (16.39 g, 86%). 1R: $\upsilon_{max}$ (KBr) 3500, 2988, 2880, 1791, 1726, 1702, 1466, cm$^{-1}$. $^1$H NMR: δ$_H$[(CD$_3$)$_2$SO] 1.32(3H,s,CH$_3$), 1.35(3H, s,CH$_3$, 2.04(1H,m,CH), 3.77(2H,dd, J=11.9, 6.0 Hz, 2× H(ax)), 4.00 (2H,dd, J=11.9, 4.1 Hz, 2×H(eq)) 4.22(2H,d, J=7.0 Hz, CH$_2$ON), 7.86(H,s, aromatic). Found: C, 61.77; H, 5.79; N, 4.88%. C$_{15}$H$_{17}$NO$_5$ requires: C, 61.84; H, 5.89; N, 4.81%.

(d) (2,2-Dimethyl-1,3-dioxan-5-ylmethoxy)amine.

Methylhydrazine (0.55 ml, 10.3 mmol) was added to a stirred solution of N-(2,2-dimethyl-1,3-dioxan-5-ylmethyloxy)phthalimide (2 g, 6.87 mmol) in dichloromethane (15 ml) at 0° C. The solution was then allowed to warm to 20° C. and stirred for 1 hour. The suspension was filtered, the filtrate evaporated to dryness and the residue triturated with ether (20 ml). The suspension was filtered and the residue obtained on evaporation of the filtrate was chromatographed on silica (eluted with chloroform-ethanol, 100:1), yielding the title compound (0.87 g, 79%). 1R: $\upsilon_{max}$ (film) 3320, 3000, 2950, 2875, 1600, 1480, 1435 cm$^{-1}$. $^1$H NMR: δ$_H$[(CD$_3$)$_2$SO] 1.29(3H,s,CH$_3$), 1.30(3H,s,CH$_3$), 1.95(1H,m,CH), 3.51 (2H,d, J=6.9 Hz, CH$_2$ON), 3.58(2H,dd, J=11.8, 6.9 Hz, 2×H(ax)), 3.84(2H,dd, J=11.8, 4.4 Hz, 2×H(eq)), 5.97(2H, br.s, D$_2$O exchangeable, NH$_2$).

(e) 4-Chloro-2,5-diformamido-6-(2,2-dimethyl-1,3-dioxan-5-ylmethoxyamino)pyrimidine.

A mixture of 4,6-dichloro-2,5-diformamidopyrimidine (3.25 g, 13.8 mmol), 2,2-dimethyl-1,3-dioxan-5-ylmethoxyamine (2.26 g, 14.0 mmol), trithylamine (5 ml) and dioxan (50 ml) was heated at reflux temperature for 2 hours. The suspension was cooled, filtered and the filtrate evaporated under reduced pressure. The residue was chromatographed on silica gel (eluted with chloroform-ethanol, 50:1 then 30:1), yielding the title compound (2.10 g, 42%). 1R: $\upsilon_{max}$ (KBr) 3240, 1690, 1585, 1570, 1480, 1420 cm$^{-1}$. $^1$H NMR: δ$_H$[(CD$_3$)$_2$SO] 1.30(3H,s,CH$_3$), 1.34(3H,s,CH$_3$), 1.99(1H,m,CH), 3.70(2H,m, 2×H(ax)), 3.93(4H,m,CH$_2$ON, 2×H (eq)), 8.15, 8.31(1H, 2×s, NHCHO), 9.17, 9.42(1H, 2×br.s, D$_2$O exchangeable, NHCHO), 9.26(1H, br.s, NHCHO), 10.83(2H, br.s, D$_2$O exchangeable, NHCHO, NHO). Found: C, 42.93; H, 5.09; N, 19.75%. C$_{13}$H$_{18}$ClN$_5$O$_5$ requires: C, 43.39; H, 5.05; N, 19.47%.

(f) 6-Chloro-9-(2,2-dimethyl-1,3-dioxan-5-ylmethoxy)-2-formamidopurine.

4-Chloro-2,5-diformamido-6-(2,2-dioxan-5-ylmethoxyamino)pyrimidine (1.9 g, 5.28 mmol) in diethoxymethylacetate (25 ml) was heated at 120° C. for 2 hours. The mixture was then cooled and evaporated to a syrup. The residue was dissolved in methanol (70 ml) and concentrated aqueous ammonia (2.5 ml). The solution was then stirred at 20° C. for 1 hour, evaporated under reduced pressure and the residue co-evaporated with methanol. Column chromatography on silica gel (eluted with chloroform-methanol, 50:1) gave the title compound (1.47 g, 81%). IR: $\nu_{max}$ (KBr) 3419, 1720, 1616, 1579, 1513, 1507, 1439 cm$^{-1}$. $^1$H NMR: $\delta_H$[(CD$_3$)$_2$SO] 1.32(3H,s,CH$_3$), 1.37(3H,s,CH$_3$), 2.04(1H,m,CH), 3.80(2H,dd, J=11.8, 5.5 Hz, 2×H(ax)), 4.03(2H,dd, J=12.1, 3.9 Hz, 2×H(eq)), 4.51(2H,d, J=7.3 Hz,CH$_2$ON), 8.84(1H,s,H-8),9.38(1H,s,CHO), 11.31(1H, br.s, D$_2$O exchangeable, NH$_2$). M+ observed 341.0891. C$_{13}$H$_{16}$ClN$_5$O$_4$ requires: 341.0891.

(g) 2-Amino-9-(2,2-dimethyl-1,3-dioxan-5-ylmethoxy) purine.

A mixture of 4-Chloro-9-(2,2-dimethyl-1,3-dioxan-5-ylmethoxy)-2-formamidopurine (1.47 g, 4.30 mmol), 10% palladium on charcoal (75 mg), ammonium formate (3.0 g, 47.6 mmol) and methanol (50 ml) was stirred at reflux temperature for 4 hours. Additional ammonium formate (0.75 g) was added after 1.5, 2 and 3 hours. After cooling the mixture was evaporated to dryness and the residue partitioned between ethyl acetate (50 ml) and water (50 ml). The phases were separated and the 4 aqueous layer extracted with ethyl acetate (25 ml). The combined ethyl acetate extracts were washed with water (25 ml) dried (magnesium sulphate) and evaporated under reduced pressure. The residue was dissolved in methanol (25 ml) and hydrazine hydrate (2 ml). The solution was heated at reflux temperature for 45 minutes, cooled and evaporated under reduced pressure. Column chromatography on silica gel (eluted with chloroform-methanol, 15:1) gave the title compound. (530 mg, 43%). IR: $\nu_{max}$ (KBr) 3327, 3193, 1655, 1622, 1580, 1515, 1434 cm$^{-1}$. $^1$H NMR: $\delta_H$[(CD$_3$)$_2$SO] 1.33(3H,s,CH$_3$), 1.35(3H,s,CH$_3$), 2.02(1H,m,CH), 3.79(2H,dd, J=12.1, 5.8 Hz, 2×H(ax)), 4.05(2H,dd, J=12.1, 4.1 Hz, 2×H(eq)), 4.39(2H,d, J=7.1 Hz, CH$_2$ON), 6.70(2H,br,s,NH$_2$), 8.34(1H,s,H-8),8.59 (1H,s,H-6). Found: C, 51.33; H, 6.20; N, 25.18%; M+ 279.1339. C$_{12}$H$_{17}$N$_5$O$_3$ requires: C, 51.59; H, 6.15; N, 25.08%; M+ 279.1331.

Description 11 (Intermediate for Example 20)

2-Amino-9-(2,2-dimethyl-1,3-dioxan-5-ylmethoxy)-6-methoxypurine.

6-Chloro-9-(2,2-dimethyl-1,3-dioxan-5-ylmethoxy)-2-formamidopurine (0.5 g, 1.46 mmol) in 1.2M sodium methoxide in methanol (3.38 ml) and methanol (5 ml) was heated at reflux temperature for 1.5 hours and then cooled. Acetic acid (0.16 ml) was added and the solution evaporated to dryness. The residue was suspended in water and extracted with ethyl acetate (2×50 ml). The combined ethyl acetate extracts were washed with water, dried (magnesium sulphate) and evaporated under reduced pressure. Chromatography on silica gel (eluted with chloroform-ethanol, 100:1) gave the title compound (310 mg, 69%). IR: $\nu_{max}$ (KBr) 3397, 3208, 1640, 1616, 1581, 1480, 1390 cm$^{-1}$. $^1$H NMR: $\delta_H$[(CD$_3$)$_2$SO] 1.32(3H,s,CH$_3$), 1.35(3H,s,CH$_3$), 2.00(1H,m,CH), 3.77(2H,dd, J=11.8, 6.1 Hz, 2×H(ax), 3.9 (3H,s,OCH$_3$), 3.99(2H,dd,J=11.8, 4.1 Hz, 2×H(eq)), 4.36(2H,d, J=6.8 Hz, CH$_2$ON), 6.60(2H,br.s, D$_2$O exchangeable, NH$_2$), 8.14(1H,s,H-8). Found: C, 49.30; H, 6.12; N, 22.03%; M+ 309.1455. C$_{13}$H$_{19}$N$_5$O$_4$ 0.5H$_2$O requires: C, 49.04; H, 6.34; N, 22.00%; M+ 309.1437.

Description 12 (Intermediate for Example 21)

2,6-Diamino-9-(2,2-dimethyl-1,3-dioxan-5-ylmethoxy)purine.

A mixture of 6-Chloro-9-(2,2-dimethyl-1,3-dioxan-5-ylmethoxy)-2-formamidopurine (630 mg, 1.84 mmol), ammonia (10 ml) and methanol (15 ml) was heated at 110° C. for 7.5 hours in an autoclave and then allowed to cool over 16 hours. The mixture was evaporated to dryness and the residue chromatographed on silica (eluted with chloroform-ethanol, 20:1), affording the title compound (340 mg, 63%). IR: $\nu_{max}$ (KBr) 3409, 3321, 3158, 1669, 1640, 1589, 1488, 1457, 1409 cm$^{-1}$. H NMR: $\delta_H$[(CD$_3$)$_2$SO] 1.32(3H,s,CH$_3$), 1.35(3H,s,CH$_3$), 2.00(1H,m,CH$_3$), 3.77(2H,dd, J=11.8, 6.1 Hz, 2×H(ax)), 3.98(2H,dd, J=11.8, 4.1 Hz, 2×H(eq)), 4.32(2H,d, J=7.1 Hz, CH$_2$ON), 5.91(2H,br.s, D$_2$O exchangeable, 6-NH$_2$), 6.78(2H.br,s,D$_2$O exchangeable, 2-NH$_2$), 7.96(1H,s,H-8). Found: C, 48.34; H, 6.18; N, 28.21%; M+ 294.1437. C$_{12}$H$_{18}$N$_6$O$_3$0.2H$_2$O requires: C, 48.37; H, 6.24; N, 28.21%; M+ 294.1440.

Description 13 (Intermediates for Examples 10,22–24)

(a) 3-Bromo-1-t-butyldimethylsilyloxypropane.

A mixture of 3-Bromo-1-propanol (10 g, 6.51 ml, 71.9 mmol), t-butyldimethylsilylchloride (13.0 g, 86.2 mmol), imidazole (12.24 g, 180 mmol) and N,N-dimethylformamide (60 ml) was stirred at 20° C. for 24 hours. The reaction was then poured into water (300 ml) and extracted with ether (2×200 ml). The combined ether extracts were washed with dilute hydrochloric acid (50 ml) brine (50 ml), dried (magnesium sulphate) and evaporated to dryness. IR: $\nu_{max}$ (film) 2956, 2930, 2858, 1473, 1257, 1106, cm$^{-1}$. $^1$H NMR: $\delta_H$[(CDCl$_3$) 0.00(6H,g,s, 2×CH$_3$Si), 0.80(9H,s, 3×CH$_3$C), 1.90(2H,m, CH$_2$CH$_2$CH$_2$), 3.70(4H,m,CH$_2$O, CH$_2$Br).

(b) N-(3-t-Butyldimethylsilyloxy-1-propoxy)phthalimide.

N-Hydroxyphthalimide (9.81 g, 60.2 mmol) was added portionwise to a stirred suspension of sodium hydride (60%, 2.41 g, 60.2 mmol) in N,N-dimethylformamide (100 ml) at 20° C. After 20 minutes 3-bromo-1-t-butyldimethylsilyloxypropane (15.22 g, 60.2 mmol) was added and the mixture heated at 50° C. for 24 hours.

The mixture was cooled, poured into water (300 ml) and extracted with ether (2×200 ml). The combined ether extracts were washed with brine (100 ml), dried and evaporated under reduced pressure. Chromatography on silica gel (eluted with hexane: acetone, 5:1) gave the title compound (10.80 g, 53%). IR: $\nu_{max}$ (film) 2955, 2930, 2857, 1791, 1737, 1468 cm$^{-1}$. $^1$H NMR: $\delta_H$ (CDCl$_3$) 0.05(6H g,s, 2×CH$_3$Si), 0.90(9H,s, 3×CH$_3$C), 1.90(2H, quintet, J=6 Hz, CH$_2$CH$_2$CH$_2$), 3.80(2H,t, J=6 Hz, CH$_2$OSi), 4.25(2H,t, J=6 Hz, CH$_2$ON), 7.75(4H,s,aromatic). Found: m/z 320.1324. C$_{16}$H$_{22}$NO$_4$Si-CH$_3$ requires m/z 320.1318.

(c) 3-t-Butyldimethylsilyloxy-1-propoxyamine.

Methylhydrazine (2.5 ml, 40.0 mmol) was added to N-(3-t-butyldimethylsilyloxyprop-1-oxy)phthalimide (10.5 g, 31.3 mmol) in dichloromethane (70 ml) at 0° C. The suspension was then allowed to warm to 20° C. and stirred for 1 hour. The suspension was filtered, the filtrate evaporated to dryness and the residue triturated with ether (20 ml). The suspension was filtered and the residue obtained on evaporation of the filtrate was chromatographed on silica (eluted with chloroform-hexane, 10:1), affording the title compound (5.13 g, 80%). IR: $\upsilon_{max}$ (film) 2956, 2930, 2858, 1588, 1473, 1464 cm$^{-1}$. $^1$H NMR: $\delta_H$ (CDCl$_3$) 0.0(6H,g,s, 2×CH$_3$Si), 0.85(9H,s, 3×CH$_3$C), 1.70(2H, quintet, J=6 Hz, CH$_2$CH$_2$CH$_2$), 3.60(2H, t, J=6 Hz, CH$_2$O), 3.70 (2H, t, J=6 Hz, CH$_2$O), 5.20(2H,br.s, D$_2$O exchangeable, NH$_2$).

(d) 6-(3-t-Butyldimethylsilyloxy-1-propoxyamino)-4-chloro-2,5-diformamidopyrimidine.

A mixture of 4,6-dichloro-2,5-diformamidopyrimidine (3 g, 12.8 mmol), 3-t-butyldimethylsilyloxyprop-1-oxyamine (2.62 g, 12.8 mmol), triethylamine (5 ml) and dioxan (50 ml) was heated under reflux for 3 hours. The suspension was cooled, filtered and the filtrate evaporated under reduced pressure. The residue was chromatographed on silica (eluted with chloroform-methanol, 50:1), yielding the title compound (2.15 g, 41%). $^1$H NMR: $\delta_H$ (CDCl$_3$) 0.0(6H,s, 2×CH$_3$Si), 0.89(9H,s, 3×CH$_3$C), 1.90(2H, quintet, J=6.3, 6.1 Hz, CH$_2$CH$_2$CH$_2$), 3.77(2H, t, J=6 Hz, CH$_2$OSi), 4.07 (2H, t, J=6 Hz, CH$_2$ON), 7.85(1H,br.d, J=10 Hz, NHCHO), 8.34(1H,s,NNCHO), 8.75, 8.76(1H, 2×s, NH), 9.40(1H,d, J=10 Hz, NHCHO).

(e) 9-(3-t-Butyldimethylsilyloxyprop-1-oxy)-6-chloro-2-formamidopurine.

6-(3-t-Butyldimethylsilyloxyprop-1-oxyamino)-4-chloro-2,5-diformamidopyrimidine (2.15 g, 5.33 mmol) in diethoxymethyl acetate (20 ml) was heated at 120° C. for 1.5 hours. The mixture was then cooled and evaporated to a syrup. The residue was dissolved in methanol (20 ml) and concentrated aqueous ammonia (0.5 ml). The solution was then stirred for 30 minutes at 20° C., evaporated under reduced pressure and the residue co-evaporated with methanol. Column chromatography on silica gel (eluted with chloroform-ethanol, 50:1) afforded the title compound (1.66 g, 81%). IR: $\upsilon_{max}$ (KBr) 3125, 2956, 2930, 1718, 1700, 1613, 1583, 1508, 1439 cm$^{-1}$. $^1$H NMR: $\delta_H$ [(CD$_3$)$_2$SO] 0.04(6H,g,s, 2×CH$_3$Si), 0.85(9H,s, 3×CH$_3$C), 1 90(2H, quintet, J=6.2 Hz, CH$_2$CH$_2$CH$_2$), 3.79(2H, t, J=6.2 Hz, CH$_2$OSi), 4.50 (2H, t, J=6.2 Hz, CH$_2$ON), 8.81(1H,s,H-8), 9.36(1H,s,CHO), 11.31 (1H,br.s, D$_2$O exchangeable, NHCHO). Found C, 46.94; H, 6.26; N, 17.96%. C$_{15}$H$_{24}$ClN$_5$O$_3$Si requires: C, 46.67; H, 6.28; N, 18.15%.

(f) 9-(3-t-Butyldimethylsilyloxyprop-1-oxy)-2-formamidopurine.

A mixture of 9-(3-t-Butyldimethylsilyloxyprop-1-oxy)-6H-chloro-2-formamidopurine (1.60 g, 4.15 mmol), 10% palladium on charcoal (80 mg), ammonium formate (1.8 g, 4.9 mmol) and methanol (50 ml) was heated under reflux for 3 hours. Additional ammonium formate (0.8 g) was added after 1 and 2 hours. The mixture was then cooled, evaporated to dryness and the residue partitioned between ethyl acetate (50 ml) and water (50 ml). The phases were separated and the aqueous phase extracted with ethyl acetate (25 ml). The combined organic phases were washed with water (25 ml), dried (magnesium sulphate) and evaporated under reduced pressure. Column chromatography on silica (eluted with chloroform-ethanol, 30:1) afforded the title compound (0.81 g, 56%).
IR: $\upsilon_{max}$ (KBr) 3120, 2950, 2925, 1695, 1615, 1410 cm$^{-1}$.

$^1$H NMR: $\delta_H$[(CD$_3$)$_2$SO] 0.04(6H,s,2×CH$_3$Si), 0.85(9H,s,3×CH$_3$C), 1.90(2H, quintet, J=6.3 Hz,CH$_2$CH$_2$CH$_2$), 3.79(2H,t,J=6.3 Hz, CH$_2$OSi), 4.49(2H,t, J=6.3 Hz, CH$_2$ON), 8.72(1H,s,H-8), 8.98(1H,s,H-6), 9.43(1H,d,J=9.1 Hz, NHCHO), 11.10 (1H,d, J=9.3 Hz, D$_2$O exchangeable, NHCHO).

Description 14 (Intermediates for Example 27).

(a) (R)-N-(2,2-Dimethyl-1,3-dioxolan-4-yl methoxy)phthalimide.

To a solution of (S)-2,2-dimethyl-1,3-dioxolane-4-methanol (27 g, 0.2 mol), triphenylphosphine (53.5 g, 0.2 mol) and N-hydroxyphthalimide (33.3 g, 0.2 mol) in dry tetrahydrofuran (500 ml) cooled to 0° C. was added diethylazodicarboxylate (38.5 g, 0.22 mol). After stirring for 18 hours at 20° C. the originally dark red solution turned pale yellow and was then evaporated to dryness under reduced pressure. The residue was loaded onto a silica column in chloroform and eluted with hexane-acetone (3:1), yielding (R)-N-(2,2-dimethyl-1,3-dioxolan-4-ylmethoxy)phthalimide as white plates (31.2 g, 55%), m.p. 100°-2° C. $[\alpha]_D^{20}$= +15.6° (C 0.98 in methanol); IR: $\upsilon_{max}$ (nujol) 1790, 1770, 1720, 1600 cm$^{-1}$; $^1$H NMR: $\delta_H$ (CDCl$_3$), 1.35 (3H, s, CH$_3$), 1.41 (3H, s, CH$_3$), 3.97 (1H, q, J=5.5, 8.8 Hz, CH$_2$ON/CH$_2$OC), 4.17 (2H, m, 1H of CH$_2$ON+1H of CH$_2$OC), 4.32 (1H, q, J=5.5, 10.0 Hz, CH$_2$ON/CH$_2$OC), 4.50 (1H, m, CH), 7.74-7.87 (4H, m, aromatic); m/z 262 (M+-CH$_3$, 50%).

Found: C, 60.75; H, 5.45; N, 5.05%. C$_{14}$H$_{15}$NO$_5$ requires C, 60.64; H, 5.45; N, 5.05%.

(b) (R)-(2,2-Dimethyl-1,3-dioxolan-4-yl-methoxy)amine

A solution of (R)-N-(2,2-dimethyl-1,3-dioxolan-4-ylmethoxy) phthalimide (10 g, 36 mmol) in dichloromethane (150 ml) was cooled to 0° C. and treated with N-methylhydrazine (2.66 g, 58 mmol). The reaction was stirred for 1 hour at 25° C., filtered and evaporated. Ether was added, the suspension filtered and the filtrate evaporated to dryness under reduced pressure. The residue was chromatographed on silica eluting with ethyl acetate, affording (R)-2,2-dimethyl-1,3-dioxolan-4-ylmethoxy)amine (4.7 g, 89%) as a pale yellow liquid. IR: $\upsilon_{max}$ (film) 3550, 3300, 1600 cm$^{-1}$; $^1$H NMR $\delta_H$ (CDCl$_3$) 1.38 (3H, s, CH$_3$), 1.44 (3H, s, CH$_3$), 3.73 (3H, m, CH$_2$ON+1H of CH$_2$OC), 4.07 (1H, q, J=6.4, 8.2 Hz, 1H of CH$_2$OC), 5.56 (2H, br. s, D$_2$O exchangeable, NH$_2$); m/z 132 (M+-CH$_3$, 29%).

Found: C, 48.58; H, 8.90; N, 9.02%. C$_6$H$_{13}$NO$_3$ requires C, 48.97; H, 8.90; N, 9.52%.

(c) (R)-4-Chloro-2,5-diformamido-6-(2,2-dimethyl-1,3-dioxolan-4-ylmethoxyamino)pyrimidine.

A mixture of 4,6-dichloro-2,5-diformamidopyrimidine (3.5 g, 15 mmol), (R)-(2,2-dimethyl-1,3-dioxolan-4-ylmethoxy)amine (2.65 g, 18 mmol) and triethylamine (20 ml, 150 mmol) in dioxan (80 ml) was stirred at 100° C. for 4 hours. The reaction was cooled, filtered and evaporated under reduced pressure. The residue was chromatographed on silica, eluting with chloroform-methanol (10:1), affording slightly impure (R)-4-chloro-2,5-diformamido-6-(2,2-dimethyl-1, 3-dioxolan-4-ylmethoxyamino)pyrimidine (1.05 g, 20%) as pale orange solid. IR: $\upsilon_{max}$ (nujol) 3400, 3300, 3180, 1690, 1650 cm$^{-1}$;

$^1$H NMR: $\delta_H$ (CDCl$_3$) 1.39 (3H, s, CH$_3$), 1.47(3H,s,CH$_3$), 3.81 (1H, q, J=6.3, 8.2 Hz, CH$_2$OC), 4.03 (2H, d, J=5.5 Hz, CH$_2$ON), 4.11 (1H, q, J=6.6, 8.2 Hz, CH$_2$OC), 4.41 (1H, m, CHOC), 7.29 (1H, s, D$_2$O exchangeable, NH), 7.97 (1H, br. d, J=10.5 Hz, D$_2$O exchangeable, NH), 8.34 (1H, s, CHO), 8.94 (1H, br. s, D$_2$O exchangeable, NH), 9.43 (1H, d, J=10.5 Hz, CHO). m/z FAB (+ve ion thioglycerol) 346 (MH$^+$, 100%).

(d) (R)-6-Chloro-9-(2,2 dimethyl-1,3-dioxolan-4-yl methoxy)-2-formamidopurine

A solution of (R)-4-chloro-2,5-diformamido-6-(2,2-dimethyl-1,3-dioxolan-4-ylmethoxyamino)pyrimidine 11 (900 mg, 2.6 mmol) in diethoxymethyl acetate (20 ml) was stirred at 120° C. for 3 hours. The solvent was removed under reduced pressure, the residue dissolved in methanol (20 ml) containing 0.88 ammonia solution (0.5 ml) and the mixture stirred for 1 hour at 25° C. The solvents were evaporated under reduced pressure and the residue chromatographed on silica, eluting with ethyl acetate-hexane (2:1), affording (R)-6-chloro-9-(2,2-dimethyl-1,3-dioxolan-4-ylmethoxy)-2-formamidopurine (530 mg, 62%), m.p. 145°-8° C. UV: $\lambda_{max}$ (MeOH) 232 ($\epsilon$ 26,800), 291 ($\epsilon$ 9,600)nm; 1R: $\upsilon_{max}$ (nujol) 1700, 1600, 1580 cm$^{-1}$; $^1$H NMR: $\delta_H$ (CDCl$_3$) 1.37 (3H,s, CH$_3$), 1.42 (3H s, CH$_3$), 3.87 (1H, m, CH$_2$OC), 4.12 (1H, m, CH$_2$OC), 4.46 (3H, m, CH+CH$_2$ON), 8.20 (1H, s, H-8), 8.44 (1H, br. d, J=11.5 Hz, D$_2$O exchangeable, NH), 9.55 (1H, J=11.5 Hz, HCONH).

Found: C, 43.94; H, 4.34; % N, 21.59%. C$_{12}$H$_{14}$ClN$_5$O$_4$ requires C, 43.98; H, 4.31 N, 21.37%.

Description 15 (Intermediates for Examples 28, 29).

(a) O-(4-Butenyl)benzohydroxamate

To a suspension of 60% sodium hydride (8 g =4.8 g NaH, 0.2 mol) in anhydrous N,N-dimethylformamide (200 ml) was added benzohydroxamic acid (27.5 g, 0.2 mol) over 20 minutes and the reaction stirred for 1 hour at 25° C. This solution was treated with 4-bromo-1-butane (27 g, 0.2 mol) and the reaction stirred at 100° C. for 6 hours. After cooling, water (400 ml) was added and the solution was extracted with hexane (3×200 ml). The aqueous layer was evaporated under reduced pressure, the residue suspended in ethyl acetate (600 ml), washed with water (2×200 ml) and dried (MgSO$_4$). Evaporation of the solvent gave a residual oil which was distilled 11 under high vacuum affording O-(4-butenyl) benzohydroxamate (19.4 g, 51%). b.p. 0.2 140°-5° C. 1R: $\upsilon_{max}$ (film) 3200, 1640, 1600, 1580, 1510 cm$^{-1}$; $^1$HNMR: $\delta_H$(CDCl$_3$) 2.44 (2H, q, J=7 Hz, CH$_2$CH$_2$), 4.07 (2H, t, J=7.8 Hz, CH$_2$ON), 5.12 (2H m, CH$_2$=CH), 5.80 (1H, m, CH=CH$_2$), 7.26-7.90(5H, m, aromatic), 9.44 (1H, br.s, D$_2$O exchangeable, NH).

(b) O-(4-Butenyl)hydroxylamine hydrochloride

O-(4-Butenyl)benzohydroxamate (10 g, 52.4 mmol) was dissolved in ethanol (30 ml), treated with concentrated hydrochloric acid (15 ml) and boiled under reflux for 3 hours. The reaction was cooled, diluted with water (60 ml) and extracted with chloroform (3×100 ml). The aqueous layer was evaporated to dryness and the residue recrystallised from ethanol-ether, affording O-(4-butenyl)hydroxylamine hydrochloride (4.6 g, 71%) as white plates, m.p. 136°-40° C.; 1R: $\upsilon_{max}$ (KBr) 3400, 3100, 2900, 1650,1590, 1550, 1515, cm$^{-1}$; $^1$H NMR: $\delta_H$[CD$_3$)$_2$SO] 2.32 (2H, m, CH$_2$CH$_2$ON), 4.06 (2H, t, J=7 Hz, CH$_2$ON), 5.07 (2H, m, CH$_2$=CH), 5.72 (1H, m, CH=CH$_2$), 11.12 (3H, br.s, D$_2$O exchangeable, N$^+$H$_3$). Found: C, 38.23; H, 8.13; N, 11.05%. C$_4$H$_{10}$ClNO requires C, 38.87; H, 8.16; N, 11.33%.

(c) 6-(4-Butenyloxyamino)-4-chloro-2,5-diformamidopyrimidine

A solution of O-(4-butenyl)hydroxylamine hydrochloride (1.94 g, 15.7 mmol) and triethylamine (3.96 g, 5.5 ml, 39.3 mmol) in dioxan (80 ml) was stirred for 1 hour at 50° C. The suspension was cooled and filtered and then 4,6-dichloro-2,5-diformamidopyrimidine (3.35 g, 14.3 mmol) added to the filtrate. The solution was stirred at 100° C. for 4 hours, cooled, filtered and evaporated to dryness. The residue was chromatographed on silica eluting with ethyl acetate&hexane (5:1), affording 6-(4-butenyloxyamino)-4-chloro-2,5-diformamidopyrimidine (1.31 g, 32%), m.p. 151°-20° C. 1R: $\upsilon_{max}$ (nujol) 3250, 3180, 1710, 1650, 1590, 1560, 1500 cm$^1$; $^1$H NMR: $\delta_H$[(CD$_3$)$_2$SO] 2.37 (2H, ABq, J$_{AB}$=6.6 Hz, CH$_2$CH$_2$ON), 3.92 (2H, t, J=6.6 Hz, CH$_2$ON), 5.11(2H, m, CH$_2$=CH), 5.87 (1H, m, CH=CH$_2$), 8.15 (1H, s, CHO), 9.26 (1H, s, CHO), 9.41 (1H, br.s, D$_2$O exchangeable, NH), 10.85 (2H, br.s, D$_2$O exchangeable, 2×NH). Found: C, 41.93; H, 4.19; N, 25.01%. C$_{10}$H$_{12}$ClN$_5$O$_3$ requires C, 42.19; H, 3.90; N, 24.60%.

(d) 9-(4-Butenyloxy)-6-chloro-2-formamidopurine

A solution of 6-(4-butenyloxyamino)-4-chloro-2,5-diformamidopyrimidine (1.2 g, 4.2 mmol) in diethoxymethyl acetate (20 ml) was stirred at 120° C. for 4 hours. The solution was cooled, evaporated to dryness and the residue dissolved in methanol (20 ml) containing 0.88 ammonia (0.5 ml) and stirred for 1 hour at 25° C. The solvents were removed under reduced pressure and the residue chromatographed on silica, eluting with chloroform, yielding the title compound (600 mg, 55%) as a pale yellow solid, m.p. 149°-51° C. UV: $\lambda_{max}$ (MeOH) 233 ($\epsilon$ 26,400) nm; 1R: $\upsilon_{max}$ (KBr) 3420, 1720, 1610, 1580, 1540, 1510 cm$^{-1}$; $^1$H NMR $\delta_H$(CDCl$_3$) 2.53 (2H, m, CH$_2$CH$_2$ON), 4.47 (2H, t, J=7 Hz, CH$_2$ON), 5.20 (2H, m, CH$_2$=CH), 5.84 (1H, m, CH=CH$_2$), 8.14 (1H, s, H-8), 8.33 (1H, br. d, J=11 Hz, D$_2$O exchangeable, NH), 9.56 (1H, d, J=11 Hz, CHO). Found: C, 43.94; H, 3.77; N, 25.46% C$_{10}$H$_{10}$ClN$_5$O$_2$.0.3H$_2$O requires C, 43.98; H, 3.91; N, 25.65%.

(e) 2-Amino-9-(4-butenyloxy)-6-chloropurine

A solution of 9-(4-butenyloxy)-6-chloro-2-formamidopurine (600 mg, 2.24 mmol) in methanol (5 ml) was treated with 0.88 ammonia (10 ml) and stirred at 80° C. for 1 hour. The reaction was cooled and evaporated to dryness. The residue was absorbed on silica and chromatographed, elution with chloroform affording 2-amino-9-(4-butenyloxy)-6-chloropurine (420 mg, 78%), m.p. 114°-9° C. UV: $\lambda_{max}$ (MeOH) 224 ($\epsilon$ 26,300) nm; 1R: $\upsilon_{max}$ (KBr) 3470, 3310, 1630, 1620, 1570, 1500 cm$^1$; $^1$H NMR: $\delta_H$ (CDCl$_3$) 2.52 (2H, m, CH$_2$CH$_2$ON), 4.42 (2H, t, J=7 Hz, CH$_2$ON), 5.22 (2H, m, CH$_2$=CH), 5.40 (2H, br.s, D$_2$O exchangeable, NH$_2$), 5.82 (1H, m, CH=CH$_2$), 7.90 (1H, s, H-8). Found: C, 44.96; H, 4.24; N, 28.88%. C$_9$H$_{10}$Cl N$_5$O requires C, 45.10; H, 4.21; N, 29.22%.

(f) 2-Amino-6-chloro-9-(3,4-dihydroxybut-1-oxy) purine

2-Amino-9-(4-butenyloxy)-6-chloropurine (395 mg, 1.65 mmol) was dissolved in acetone (10 ml) and water (10 ml) containing a catalytic amount of osmium tetroxide. The reaction was treated with 4-methylmorpholine-N-oxide (293 mg, 2.51 mmol) and stirred for 16 hours under nitrogen at 25° C. The solvents were evaporated under reduced pressure, the residue absorbed on silica and chromatographed, elution with acetone-hexane (3:1) furnishing the title compound (320 mg, 70%), m.p. 59°-164° C. UV: $\lambda_{max}$ (MeOH) 224 ($\epsilon$ 27,400), 247 ($\epsilon$ 5,400), 310 ($\epsilon$ 7,700), nm; 1R: $\upsilon_{max}$ (KBr) 3430, 3320 3210, 1650, 1620, 1570, 1520 cm$^{-1}$; $^1$H NMR: $\delta_H$

[(CD$_3$)$_2$SO] 1.74 (2H, m, CH$_2$CH$_2$ON), 3.27 (2H, m,CH$_2$OH), 3.62 (1H, m, CHOH), 4.42 (2H, t, J=7 Hz, CH$_2$ON), 4.60 (2H, m, D$_2$O exchangeable, 2×OH), 7.10 (2H, br. s, D$_2$O exchangeable, NH$_2$), 8.41 (1H, s, H-8).

Description 16 (Intermediates for Example 30).

(a) (R)-2-Amino-6-chloro-9-(2,3-dihydroxyprop-1-oxy)purine.

A solution of (R)-2-amino-6-chloro-9-(2,2-dimethyl-1, 3-dioxolan-4-ylmethoxy)purine (120 mg, 0.4 mmol) in 80% acetic acid was stirred at 25° C. for 2 hours and then at 70° C. for 1 hour. The reaction was evaporated to dryness, the residue absorbed on silica and chromatographed, eluting with acetone-hexane (3:1), affording the title compound (65 mg, 63%) as a white solid, m.p. 155°–8° C. IR: $\upsilon_{max}$(KBr) 3340, 3220, 1660, 1630, 1570, 1520 cm$^{-1}$; m/z 259 (M$^+$, 20%).

Found: M$^+$ 259.0478. C$_8$H$_{10}$ClN$_5$O$_3$ requires M$^+$ 259.0472.

(b) (R)-2-Amino-6-chloro-9-(2,2-dimethyl-1,3-dioxolan-4-ylmethoxy)purine.

A solution of (R)-6-chloro-9-(2,2-dimethyl-1,3-dioxolan-4-ylmethoxy)-2-formamidopurine (170 mg, 0.52 mmol) in methanol (5 ml) and 0.88 ammonia (5 ml) was stirred at 25° C. for 4 hours. The solvents were evaporated under reduced pressure, the residue absorbed on silica and chromatographed, eluting with ethyl acetate-hexane (3:1), affording the title compound (120 mg, 77%) as a white solid, m.p. 118°–9° C. IR: $\upsilon_{max}$ (KBr) 3800, 3450, 3320, 1650, 1630, 1620, 1560, 1510 cm$^{-1}$; $^1$H NMR: $\delta_H$ [(CD$_3$)$_2$SO)] 1.28 (3H, s, CH$_3$), 1.31 (3H, s, CH$_3$), 3.77 (1H, q, J=5.7, 8.5 Hz, CH$_2$OC), 4.08 (1H, q, J=6.2, 8.5 Hz, CH$_2$OC), 4.41 (3H, m, CHOC+CH$_2$ON), 7.11 (2H, br. s, D$_2$O exchangeable, NH$_2$), 8.38 (1H, s, H-8); m/z 299 (M$^+$, 10%).

Found: M$^+$299.0786. C$_{11}$H$_{14}$Cl N$_5$O$_3$ requires M$^+$299.0785.

Description 17 (Intermediates for Examples 31 and 32)

(a) (S)-N-(2,2-Dimethyl-1,3-dioxolan-4-ylmethoxy)phthalimide

A mixture of (R)-2,2-dimethyl-1,3-dioxolane-4-methanol (7.3 g, 0.05 mol), N-hydroxyphthalimide (8.15 g, 0.05 mol) and triphenylphosphine (13.11 g, 0.05 mol) in tetrahydrofuran (200 ml) was cooled to 0° C. and stirred during the addition of diethyl azodicarboxylate (9.57 g, 0.066 mol). The dark red solution was stirred at 25° C. for 18 h when the colour had turned to pale yellow, and the solution was evaporated to dryness. The residue was extracted once with ether (200 ml) and the ether removed under reduced pressure. The residue was chromatographed in chloroform-hexane 10:1 affording (S)-N-(2,2-dimethyl-1,3-dioxolan-4-ylmethoxy)phthalimide (10.5 g, 69%) as a white solid; m.p. 99°–100° C., [α]D$^{25}$−14.6° (0.4 in MeOH); $\upsilon_{max}$ (KBr) [α]$_D^{25}$ 1790, 1730 and 1610 cm$^{-1}$; $\delta_H$ (CDCl$_3$) 1.35(3H,S,CH$_3$), 1.4 (3H,S,CH$_3$), 3.99(1H,q,J5.5,8.8 Hz,CH$_2$ON/CH$_2$OCMe$_2$), 4.17(2H,m,1H of CH$_2$ON+1H of CH$_2$OCMe$_2$), 4.32(1H,q,J5.7,10.1 Hz,CH$_2$ON/CH$_2$OCMe$_2$), 4.50(1H,m,CH) and 7.75–7.87(4H,m,aromatic). Found: C, 60.53; H, 5.46; N, 5.03%. C$_{14}$H$_{15}$NO$_5$ requires C, 60.64; H, 5.45; N, 5.05%.

(b) (S)-2,2-Dimethyl-1,3-dioxolan-4-ylmethoxyamino

A mixture of (S)-N-(2,2-Dimethyl-1,3-dioxolan-4-ylmethoxy)phthalimide (10 g, 36 mmol), and N-methylhydrazine (3.32 g, 72 mmol) in dichloromethane (150 ml) was stirred at 25° C. for 2 h. The reaction was filtered, evaporated to dryness and the residue suspended in ether. The suspension was filtered and evaporated and the residue chromatographed in ethyl acetate affording (S)-2,2-Dimethyl-1,3-dioxolan-4-ylmethoxyamine (4.8 g, 91%) as a clear liquid [α]$_D^{25}$ −2.4° (0.49 in MeOH); $\upsilon_{max}$ (film) 3550, 3300 and 1600 cm$^{-1}$; $\delta_H$ (CDCl$_3$)1.38(3H,S,CH$_3$), 1.44(3H,S,CH$_3$), 3.71 (3H,m,CH$_2$ON+1H of CH$_2$OCMe$_2$), 4.05(1H,q,J6.3,8.2 Hz,1H of CH$_2$OCMe$_2$), 4.35(1H,m,CH) and 5.57(2H,br.s, D$_2$O exchangeable, NH$_2$); m/z 132(M$^+$-CH$_3$, 24%). Found: C, 48.76; H, 9.00; N, 9.56% C$_6$H$_{13}$NO$_3$ requires C, 48.96; H, 8.90; N, 9.52%

(c) (S)-4-Chloro-2,5-diformamido-6-(2,2-dimethyl-1,3-dioxolan-4-ylmethoxyamino)pyrimidine A mixture of 4,6-dichloro-2,5-diformamidopyrimidine (7.3 g, 31.1 mmol), (S)-2,2-dimethyl-1,3-dioxolan-4-ylmethoxyamine (4.6 g, 31.1 mmol) and diisopropylethylamine (8.03 g, 62.1 mmol) in diglyme (125 ml) was stirred at 100° C. for 4 h. The reaction was filtered, evaporated and the residue chromatographed twice in chloroform-methanol 15:1 affording (S)-4-chloro-2,5-diformamido-6-(2,2-dimethyl-1,3-dioxolan-4-ylmethoxyamino)pyrimidine(2.6 g, 24%). $\upsilon_{max}$ (CHCl$_3$) 3400, 1700, 1580, 1560 and 1470 cm$^{-1}$; $\delta_H$ (CDCl$_3$) 1.39(3H,S,CH$_3$), 1.48(3H,S,CH$_3$) , 3.60–4.65(5H,m,CH$_2$ONH+CH$_2$OCMe$_2$+CHOCMe$_2$), 7.96(1H,br.m, D$_2$O exchangeable, NH), 8.34(1H,S,CHO), 9.25(2H,br.m,D$_2$O exchangeable, 2XNH) and 9.50(1H,S,CHO); m/z 344(M$^+$-H,<1%), 330(M$^+$-CH$_3$, <1%).

(d) (S)-6-Chloro-9-(2,2-dimethyl-1,3-dioxolan-4-ylmethoxy-2-formamidopurine

A solution of (S)-4-chloro-2,5-diformamido-6-(2,2-dimethyl-1,3-dioxolan-4-ylmethoxyamino)pyrimidine (2.1 g, 6.08 mmol) in diethoxymethyl acetate (30 ml) was stirred at 120° C. for 3 h. The reaction was evaporated to dryness, the residue dissolved in methanol (40 ml) and 0.88 ammonia (1 ml) and stirred for 1.5 h. at 25° C. Evaporation and chromatography of the residue on silica eluting with ethyl acetate-hexane 1:1 gave (S)-6-chloro-9-(2,2-dimethyl-1,3-dioxolan-4-ylmethoxy)-2-formamidopurine (1.3 g, 65%) as a white solid; m.p. 147°–8° C.; $\upsilon_{max}$ (KBr) 3420, 3200, 1700, 1610, 1580, 1510, and 1440 cm$^{-1}$; $\delta_H$(CDCl$_3$) 1.40(3H,S,CH$_3$), 1.44(3H,S,CH$_3$), 3.89(1H,m,CH$_2$OCMe$_2$), 4.16(1H,m,CH$_2$OCMe$_2$), 4.50(3H,m,CH+CH$_2$ON), 8.23(1H,S,H-8), 8.45(1H,br.d,J11.5 Hz,D$_2$O exchangeable, NH) and 9.59(1H,d,J11.5 Hz,HCONH). Found C, 43.75; H, 4.29; N, 21.23%; M$^+$ 327.0734; C$_{12}$H$_{14}$ClN$_5$O$_4$ requires C, 43.98; H, 4.31; N, 21.37%; M$^+$ 327.0734.

(e) (S)-2-Amino-6-chloro-9-(2,2-dimethyl-1,3-dioxolan-4-ylmethoxy)purine

A solution of (S)-6-chloro-9-(2,2-dimethyl-1,3-dioxolan-4-ylmethoxy)-2-formamidopurine (400 mg, 1.22 mmol) in methanol (10 ml) and 0.88 ammonia (10 ml) was stirred at 25° C. for 4 h. The solution was evaporated under reduced pressure and the residue chromatographed on silica, eluting with ethyl (2,2-dimethyl-1,3-dioxolan-4-ylmethoxy)purine (270 mg, 74%) as a white Solid; m.p. 118°–120° C. $\upsilon_{max}$ (KBr) 3450, 3320, 3210, 1650, 1630, 1620, 1560, 1510 and 1470 cm$^{-1}$; $\delta_H$(CDCl$_3$) 1.36(3H,S,CH$_3$), 1.42(3H,S,CH$_3$), 3.85(1H,m,CH$_2$OCMe$_2$), 4.14(1H,m,CH$_2$OCMe$_2$), 4.43(3H,m,CH+CH$_2$ON), 5.51 (2H,br.s,D$_2$O exchangeable, NH$_2$), 8.00(1H,S,H-8). Found: C, 44.45; H, 4.69; N, 23.31%; M+ 299.0795; C₁₁H₁₄ClN₅O₃ requires C, 44.08; H, 4.71; N, 23.37%; M+ 299.0785.

(f) (S)-2-Amino-6-chloro-9-(2,3-dihydroxyprop-1-oxy)purine

A solution of (S)-2-amino-6-chloro-9-(2,2-dimethyl-1,3-dioxolan-4-ylmethoxy)purine (250 mg, 0.83 mmol) in 80% acetic acid (20 ml) was stirred at 25° C. for 2 h. and then at 70° C. for 1 h. The solution was evaporated to dryness under reduced pressure, the residue absorbed on silica and chromatographed eluting with acetone-hexane 3:1 affording (S)-2-amino-6-chloro-9-(2,3-dihydroxyprop-1-oxy)purine (170 mg, 78%) as a white solid; m.p. 155°-8° C. $\nu_{max}$ (KBr) 3340, 3200, 1660, 1620, 1560, 1520 1470 cm⁻¹; δH[(CD₃)²SO] 3.41(2H,m,CH₂OH) 3.78(1H,m,CH), 4.19(1H,q,J7.4,10.4 Hz,CH₂ON), 4.40(1H,q,J3.3,10.4 Hz,CH₂ON), 4.73(1H,t,J5.0 Hz,D₂O exchangeable, OH), 5.14(1H,d,J5.0 Hz.D₂O exchangeable, OH), 7.12(2H,S,D₂O exchangeable, NH₂) 8.35(1H,S,H-8). Found M+ 259.0475; C₈H₁₀ClN₅O₃ requires M+ 259.0472.

Description 18 (alternative intermediates for Examples 16-19)

(a) 2,4-Dichloro-5-formamidopyrimidine

Acetic anhydride (12 ml) was added to a mixture of 5-amino-2,4-dichloropyrimidine (2.34 g, 14.4 mmol) and formic acid (30 ml) at 0° C. The mixture was stirred at 20° C. for 4 hours, evaporated to dryness and co-evaporated with toluene. The crystalline product was homogeneous on t.l.c. (chloroform-methanol, 15.1) and used without further purification. (2.74 g, 100%). IR: $\nu_{max}$ (KBr) 3445, 3350, 3240, 1635, 1570, 1515, 1415 cm⁻¹. ¹H NMR $\delta_H$ [(CD₃)₂SO] 8.45 (1H,s,H.2), 9.40 (1H,s,CH), 10.40 (1H,br.s, NH).

(b) 2-Chloro-4-(2,2-dimethyl-1,3-dioxan-5-ylmethoxyamino)-5-formamidopyrimidine

A mixture of 2,4-dichloro-5-formamidopyrimidine (2.5 g, 13.0 mmol), 2,2-dimethyl-1,3-dioxan-5-ylmethoxyamine (13.6 mmol), diisopropylethylamine (4.5 ml, 25.8 mmol) and 2-methoxyethyl ether (50 ml) was heated at 100° C. for 4.5 hours. The suspension was cooled and evaporated under reduced pressure. The residue was chromatographed on silica gel (eluted with chloroform-methanol, 20:1), yielding the title compound (3.45 g, 84%).

¹H NMR $\delta_H$ (CDCl₃) 1.45 (6H,s,2×CH₃), 2.05(1H,m,CH), 3.80 (6H,m,3×CH₂), 8.3(1H,br,s,NH), 8.45 (1H,s,H-6).

(c) 2-Chloro-9(2,2-dimethyl-1,3-dioxan-5ylmethoxy)-purine

2-Chloro-4-(2,2-dimethyl-1,3-dioxan-5-ylmethoxyamino)-5-formamidopyrimidine (3.45 g, 10.9 mmol) in diethoxymethylacetate (100 ml) was heated at 120° C. for 2 hours. The mixture was then cooled and evaporated to a syrup. The residue was dissolved in methanol (50 ml) and concentrated aqueous ammonia (2.5 ml). The solution was then stirred at 20° C. for 1 hour, evaporated under reduced pressure and the residue co-evaporated with toluene. Column chromatography on silica gel (eluted with chloroform-methanol, 60:1) gave the title compound (2.27 g, 70%). IR: $\nu_{max}$ (KBr) 3117, 2993, 1599, 1571, 1339 cm⁻¹. ¹H NMR $\delta_H$[(CD₃)₂SO] 1.33 (3H,s,CH₃), 1.37 (3H,s,CH₃), 2.08 (1H,m,CH), 3.81 (2H,d.d, J=5.8, 2.1 Hz, 2×H(ax)). 4.04 (2H, d.d, J=4.0, 12.0 Hz. 2×H (eq)), 4.52 (2H, d, J=3.3 Hz, CH₂ON), 9.00 (1H,s,H-8), 9.14(1H,s,H-6). Found: C, 48.34; H, 5.13; N, 18.66%: C₁₂H₁₅ClN₄O₃ requires: C, 48.24; H, 5.07; N, 18.76%.

(d) 2-Amino-9-(2,2-dimethyl-1,3-dioxan-5-ylmethoxy)purine

Method 1

A mixture of 2-chloro-9-(2,2-dimethyl-1,3-dioxan-5-ylmethoxy)purine (100 mg, 0.335 mmol) and liquid ammonia (20 ml) was left in an autoclave at 20° C. for 48 hours. The solution was evaporated using a stream of nitrogen and the residue chromatographed on silica gel (eluted with chloroform-methanol, 15:1) affording the title compound (57.5 mg, 62%). IR: $\nu_{max}$ (KBr) 3336, 3203, 1647, 1618, 1578, 1430 cm⁻¹. ¹H NMR: $\delta_H$ [(CD₃)₂SO] 1.97 (1H,m,CH), 3.55 (4H,m, 2×CH₂OH), 4.33 (2H,d, J=6.3 Hz CH₂ON), 4.59 (2H,t, J=5.3 Hz, D₂O exchangeable, 2×OH), 6.70 (2H, br.s, D₂O exchangeable, NH₂), 8.30 (1H,s,H-8), 8.59 (1H,s,H-6).

A subsequent reaction indicated that this reaction time is not needed; about 7 hours should be sufficient.

Method 2

A stream of ammonia was bubbled through a solution of 2-chloro-9-(2,2-dimethyl-1,3-dioxan-5-ylmethoxy)purine (100 mg) in dimethylsulphoxide at 100° C. After 3 hours the solution was cooled, evaporated to dryness and the residue purified by column chromatography on silica gel eluting with chloroform-methanol (15:1) to afford 2-amino-9-(2,2-dimethyl-1,3-dioxan-5-ylmethoxy) purine (55 mg; 59%): IR: $\nu_{max}$ (KBr) 3327, 3193, 1655, 1622, 1580, 1515 and 1434 cm⁻¹. ¹H NMR: $\delta_H$ [(CD₃)₂SO] 1.33 (3H,s,CH₃), 1.35 (3H,s,CH₃), 2.02 (1H.m,CH), 3.79 (2H,dd, J=12.1 Hz, and 5.8 Hz, 2×H(ax)), 4.05 (2H, dd, J=12.1 Hz and 4.1 Hz, 2×H (e.g.)), 4.39 (2H,d, J=7.1 Hz, CH₂ON), 6.70 (2H,s,D₂O exchangeable, NH₂), 8.34 (1H,s,H-8), 8.59 (1H,s,H-6).

EXAMPLE 1

9-(3-Hydroxyprop-1-oxy)guanine

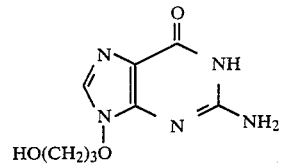

Method A

A mixture of 9-(3-benzyloxyprop-1-oxy)guanine (140 mg; 0.44 mmol), 10% palladium on charcoal 200 mg), water (20 ml), 5N hydrochloric acid (10 ml) and ethanol (10 ml) was stirred at 20° C. under an atmosphere of hydrogen for 45 minutes. The catalyst was filtered off, the solution adjusted to pH 7 and evaporated to dryness under reduced pressure. The residue was crystallised from water to yield 42 mg of a white solid, which was recrystallised once more from water to give the title compound (23 mg, 23%).

¹H NMR: $\delta_H$ [(CD₃)₂SO] 1.80 (2H, quintet, J=6.3, 6.6 Hz, CH₂CH₂CH₂), 3.55 (2H, quartet, J=5.50, 5.77 Hz, CH₂OH), 4.32 (2H, t, J=6.6 Hz, CH₂ON), 4.57 (1H, t, J=5.0, 5.5 Hz, D₂O exchangeable, OH), 6.57 (2H, br.s, D₂O exchangeable, NH₂), 7.91 (1H, s, H-8), 10.63 (1H, br s, D₂O exchangeable, H-1). Found: C, 41.33; H, 5.20; N, 30.24%. C₈H₁₁N₅O₃.0.4 H₂O requires C, 41.33; H, 5.13; N, 30.14%.

Method B 9-(3-Benzyloxyprop-1-oxy)-6-chloro-2-formamidopurine (3.40 g, 9.41 mmol) in 80% formic acid (100 ml) was heated at 100° C. for 1 hour. The reaction mixture was then cooled and stirred with 10% palladium on charcoal (2.0 g) under an atmosphere of hydrogen at 20° C. for 45 minutes. After removal of the catalyst, the solution was evaporated and the residue was treated with water (50 ml) and concentrated aqueous ammonia (4 ml) at 100° C. for 15 minutes. The solution was then cooled and evaporated under reduced pressure. Recrystallisation of the residue from water afforded 9-(3-hydroxyprop-1-oxy)guanine (800 mg, 33%). $^1$H NMR: δH [(CD$_3$)$_2$SO] 1.80 (2H, quintet, J=6.3, 6.6 Hz, CH$_2$CH$_2$CH$_2$), 3.55 (2H, quartet, J=5.50, 5.8 Hz, CH$_2$OH), 4.32 (2H, t, J=6.6 Hz, CH$_2$ON), 4.57 (1H, t, J=5.5 Hz, D$_2$O exchangeable, OH), 6.57 (2H, br.s, D$_2$O exchangeable, NH$_2$), 7.91 (1H, s, H-8), 10.63 (1H, br.s, D$_2$O exchangeable, H-1).

EXAMPLE 2

9-(3-Acetoxyprop-1-oxy)guanine

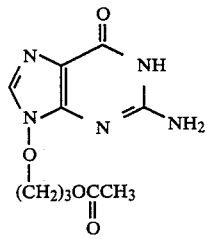

A mixture of 9-(3-hydroxyprop-1-oxy)guanine (150 mg, 0.67 mmol), 4-dimethylaminopyridine (15.6 mg, 0.13 mmol), acetic anhydride (0.25 ml, 2.65 mmol) and N,N-dimethylformamide (5 ml) was stirred at 20° C. for 3 hours and then ethanol was added. After a further 15 minutes the solvent was evaporated under reduced pressure and the residue was chromatographed on silica gel (eluted with chloroform-ethanol, 4:1), yielding the title compound (120 mg, 67%). Recrystallisation from methanol-water gave 9-(3-acetoxy-prop-1-oxy)guanine (82 mg, 46%). IR: υ$_{max}$ (KBr) 3330, 3168, 1736, 1696, 1648, 1602, 1589, 1391 cm$^{-1}$. $^1$H NMR: δH [(CD$_3$)$_2$SO] 1.98 (2H, quintet, J=6.3, 6.6 Hz, CH$_2$CH$_2$CH$_2$), 2.02 (3H, s,

4.17 (2H, t, J=6.6 Hz, CH$_2$ON), 4.32 (2H, t, J=6.3 Hz,

6.60 (2H, br.s, D$_2$O exchangeable NH$_2$), 7.94 (1H, s, H-8), 10.69 (1H, br.s, D$_2$O exchangeable, H-1). Found: C, 44.99; H, 4.93; N, 26.20% M+ 267.0964 C$_{10}$H$_{13}$N$_5$O$_4$ requires C, 44.93; H, 4.91; N, 26.21% M+ 267.0968.

EXAMPLE 3

9-(3-Benzoyloxyprop-1-oxy)guanine

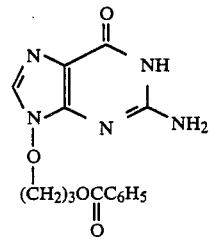

A mixture of 9-(3-hydroxyprop-1-oxy)guanine (150 mg, 0.67 mmol), 4-dimethylaminopyridine (15.6 mg, 0.13 mmol) benzoic anhydride (150 mg, 2.65 mmol) and N,N-dimethylformamide (5 ml) was stirred at 20° C. for 24 hours. The mixture was then evaporated to dryness and the residue was chromatographed on silica gel (eluted with chloroform-ethanol, 10:1). Recrystallisation from water-methanol afforded 9-(3-benzoyloxy-prop-1-oxy)guanine (75 mg, 36%). IR: υ$_{max}$ (KBr) 3393, 3200, 1714, 1700, 1639, 1595, 1582, 1391 cm$^{-1}$. $^1$H NMR: δH [(CD$_3$)$_2$SO] 2.13 (2H, quintet, J=6.3 Hz, CH$_2$CH$_2$CH$_2$), 4.43 (2H, t, J=6.6 Hz, CH$_2$), 4 46 (2H, t, J=6.3 Hz, CH$_2$), 6.60 (2H, br.s, D$_2$O exchangeable, NH$_2$), 7.53 (2H, m, 2 protons of PhCO$_2$), 7.67 (1H, m, 1 proton of PhCO$_2$), 7.97 (1H, s, H-8), 7.97 (2H, m, 2 protons of PhCO$_2$), 10.72 (1H, br.s, D$_2$O exchangeable, H-1). Found; C, 54.52; H, 4.72; N, 20.98%, M+ 329.1126 C$_{15}$H$_{15}$N$_5$O$_4$ requires C, 54.70; H, 4.60; N, 21.27% M+ 329.1124.

EXAMPLE 4

2-Amino-6-ethoxy-9-(3-hydroxyprop-1-oxy)purine

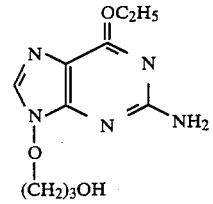

A mixture of 2-amino-9-(3-benzyloxyprop-1-oxy)-6-ethoxypurine (350 mg, 1.02 mmol), 10% palladium on charcoal (350 mg) and 80% formic acid (10 ml) was stirred at 20° C. under an atmosphere of hydrogen for 45 minutes. The catalyst was removed and the solution was evaporated under reduced pressure. The residue was dissolved in water (10 ml) and heated to boiling. Concentrated aqueous ammonia (1 ml) was then added and the solution heated for 15 minutes and then cooled and evaporated under reduced pressure. Recrystallisation of the residue from water afforded the title compound (145 mg, 56%). IR: υ$_{max}$ (KBr) 3376, 3326, 3205, 1649, 1611, 1581, 1509, 1454, 1402 cm$^{-1}$. $^1$H NMR: δH [(CD$_3$)$_2$SO] 1.35 (3H, dd, J=6.9, 7.1 Hz, CH$_2$CH$_2$O), 2.50 (2H, quintet, J=6.3, 6.6 Hz, CH$_2$), 3.56 (2H, dt, J=5.2, 6.3 Hz, CH$_2$OH), 4.35 (2H, t, J=6.6 Hz, CH$_2$ON), 4.45 (2H, quartet, J=6.9, 7.1 Hz, OCH$_2$CH$_3$), 4.61 (1H, t, J=5.2 Hz, D$_2$O exchangeable, OH), 6.56 (2H, br.s, D$_2$O exchangeable, NH$_2$), 8.09 (1H, s, H-8). Found: C, 47.16; H, 5.92; N, 27.60%. C$_{10}$H$_{15}$N$_5$O$_3$ requires: C, 47.41; H, 5.98; N, 27.65%.

EXAMPLE 5

9-(3-Hydroxy-2-hydroxymethylprop-1-oxy)guanine

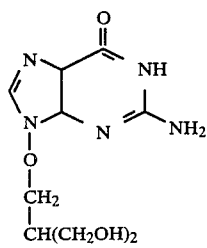

A mixture of 9-(3-benzyloxy-2-benzyloxymethyl-prop-1-oxy)-2-formamido-6-chloropurine (2.5 g, 5.2 mmol) and 80% formic acid (100 ml) was stirred at 100° C. for 1 hour, cooled and 10% palladium on charcoal (2.0 g) added. The mixture was then stirred under an atmosphere of hydrogen for 45 minutes. The catalyst was removed and the solution evaporated under reduced pressure. The residue obtained was heated in water (100 ml) until boiling commenced. Concentrated aqueous ammonia (4 ml) was added and the solution was then heated for a further 15 minutes, cooled and evaporated under reduced pressure. Recrystallisation from water (charcoal) afforded 9-(3-hydroxy-2-hydroxymethylprop-1-oxy)guanine (430 mg, 32%). IR: $\nu_{max}$ (KBr) 3380, 3183, 1679, 1637, 1605, 1541, 1479, 1395 cm$^{-1}$. $^1$H NMR: $\delta$H [(CD$_3$)$_2$SO] 1.94 (1H, m, CH), 3.53 (4H, m, 2×CH$_2$OH), 4.26 (2H, d, J=6.3 Hz), 4.57 (2H, t, J=5.2 Hz, D$_2$O exchangeable, 2×OH), 6.58 (2H, br.s, NH$_2$), 7.92 (1H, s, H-8), 10.64 (1H, br.s, D$_2$O exchangeable, H-1). Found: C, 42.08; H, 5.15; N, 27.41%. C$_9$H$_{13}$N$_5$O$_4$ requires: C, 42.34; H, 5.14; N, 27.44%.

EXAMPLE 6

9-(2,3-Dihydroxyprop-1-oxy)guanine

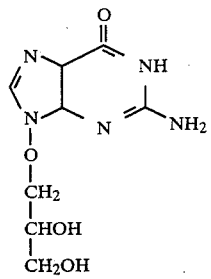

2-Amino-6-chloro-9-(2,3-dihydroxyprop-1-oxy)purine (100 mg, 0.39 mmol) was dissolved in 80% formic acid solution and stirred at 100° C. for 2.5 hours. The reaction was evaporated to dryness under reduced pressure and the residue treated with methanol (5 ml) and 0.88 ammonia solution (3 ml). After stirring the reaction at 60° C. for 2 hours, the solvents were evaporated under reduced pressure and the residue recrystallised from water yielding the title compound (35 mg, 38%), m.p. 252°–3° C. Uv: $\lambda_{max}$ (H$_2$O) 252 ($\epsilon$12,600) nm; IR: $\nu_{max}$(KBr) 3330, 1690, 1640, 1605, 1540, 1475 cm$^{-1}$; $^1$H NMR: $\delta$H [(CD$_3$)$_2$SO] 3.39 (2H, m, CH$_2$OH), 3.72 (1H, m, CHOH), 4.10 (1H, dd, J=10.7, 7.6 Hz, 7.6 Hz, CH$_2$ON), 4.33 (1H, dd, J=10.5, 3.3 Hz, CH$_2$ON), 4.70 (1H, t, J=5.7 Hz, OH), 5.15 (1H, d, J=5.2 Hz, OH), 6.62 (2H, br.s, NH$_2$), 7.90 (1H, s, H-8), 10.58 (1H, br.s, NH); m/z 241 (M+, 3%), 210 (2), 167 (27), 151 (100), 109 (20), 61 (47). Found: C, 38.85; H, 4.66; N, 29.14%, M+ 241.0813. C$_8$H$_{11}$N$_5$O$_4$ requires C, 39.84; H, 4.60; N, 29.03%, M+ 241.0811.

EXAMPLE 7

2-Amino-9-(2,3-dihydroxyprop-1-oxy)purine

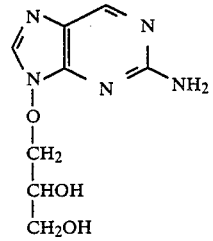

A mixture of 2-amino-6-chloro-9-(2,3-dihydroxyprop-1-oxy)purine (150 mg, 0.58 mmol), ammonium formate (146 mg, 2.32 mmol) and 10% palladium-on-charcoal (15 mg) in methanol (5 ml) was stirred under reflux for 4 hours. The reaction was evaporated under reduced pressure and the residue was dissolved in water and passed through a SEP-PAK C$_{18}$ cartridge for decolourisation. After elution with water, the water was evaporated under reduced pressure and the residue recrystallised from ethanol affording the title compound (58 mg, 45%), m.p. 183°–185° C. UV: $\lambda_{max}$(H$_2$O) 221 ($\epsilon$25,600), 305 ($\epsilon$7,000) nm; IR: $\nu_{max}$ (KBr) 3670, 3420, 3310, 3200, 1650, 1620, 1570, 1520, 1480, 1425 cm$^{-1}$; $^1$H NMR: $\delta$H (CD$_3$)$_2$SO] 3.41 (2H, m, CH$_2$OH), 3.76 (1H, m, CHOH), 4.18 (1H, dd, J=7.6, 10.7 Hz, CH$_2$ON), 4.39 (1H, dd, J=3.2, 10.7 Hz, CH$_2$ON), 4.72 (1H, t, J=5.6 Hz, OH), 5.15 (1H, d, J=5.2 Hz, OH), 6.72 (2H, br.s, NH$_2$), 8.27 (1H, s, H-8), 8.59 (1H, s, H-6). Found: C, 42.17; H, 4.91; N, 31.07%, M+ 225.0865. C$_8$H$_{11}$N$_5$O$_3$ requires C, 42.67; H, 4.92; N, 31.10%, M+ 225.0862.

EXAMPLE 8

9-(1,4-Dihydroxybut-2-oxy)guanine

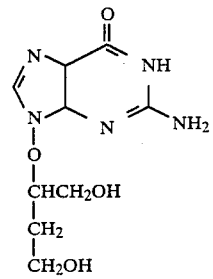

To a solution of 9-[1,4-bis(4-methoxybenzloxy)but-2-oxy]-6-chloro-2-formamidopurine (0.27 g, 0.5 mmol) in dichloromethane (2.7 ml) and water (0.15 ml) was added 2,3-dichloro-5,6-dicyanobenzoquinone (0.25 g, 1.1 mmol) and the solution was stirred at room temperature for 1 hour. The solution was diluted with dichloromethane (3 ml) and extracted with water (2×5 ml). The aqueous layers were combined, filtered and the solvent removed. The residue was purified by column chromatography on silica gel eluting with chloroform-methanol (10:1). The product was dissolved in 50% formic acid and the solution was heated at 100° C. for 1 hour. The solvent was removed and the residue co-evaporated with water. The residue was dissolved in concentrated aqueous ammonia and the solution stirred at 80° C. for 20 minutes. The solvent was removed and the residue was purified by reverse-phase column chromatography on Spherisorb C18 300 silica eluting with water followed by 5% and 10% methanol to afford 9-(1,4-dihydroxybut-2-oxy)guanine (28 mg, 23%), m.p. decomposition >215° C.; UV: $\lambda_{max}$ (H$_2$O) 252 ($\epsilon$12,400) and 265 (inflexion, $\epsilon$9,740)nm; IR: $\upsilon_{max}$ (KBr) 3360, 3200, 1735, 1690, 1640, 1600, 1540, 1475 and 1400 cm$^{-1}$; $^1$H NMR: δH [(CD$_3$)$_2$SO] 1.82 (2H, dq, J$_q$=6.5 Hz and J$_d$=1.8 Hz, 3'-H), 3.56 (4H, m, 1'-H and 4'-H), 4.34 (1H, m, 2'-H), 4.63 (1H, t, J=5.4 Hz, D$_2$O exchangeable, OH), 4.97 (1H, t, J=6.1 Hz, D$_2$O exchangeable, OH), 6.59 (2H, s, D$_2$O exchangeable, 2-NH$_2$), 7 87 (1H, s, 8-H) and 10.67 (1H, s, D$_2$O exchangeable, 1-H). Found: C, 40.33; H, 5.32; N. 26.03%. C$_9$H$_{13}$N$_5$O$_4$.0.7H$_2$O requires C, 40.36; H, 5.42; N. 26.15%.

EXAMPLE 9

2-Amino-9-(1,4-dihydroxybut-2-oxy)purine

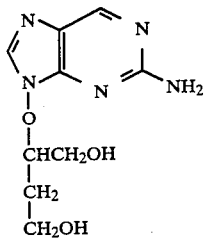

To a solution of 2-amino-9-[1,4-bis(4-methoxybenzyloxy)but-2-oxy]-6-chloropurine (0.94 g, 1.8 mmol) in dichloromethane (7.2 ml) and methanol (0.8 ml) was added 2,3-dichloro-5,6-dicyanobenzoquinone (0.91 g, 4.0 mmol) and the solution was stirred at room temperature for 80 minutes. The solution was diluted with dichloromethane (8 ml) and extracted with water (3×8 ml). The aqueous layers were combined, filtered and the solvent removed. The residue was purified by reverse-phase column chromatography on Spherisorb C$_{18}$ 300 silica eluting with 10% methanol in water followed by column chromatography on silica gel eluting with chloroform-methanol (12:1). The product was suspended in a solution of ammonium formate (208 mg, 3.3 mmol) in methanol (8 ml), 10% palladium-on-charcoal was added (25 mg) and the mixture was heated under reflux. After 30 minutes further 10% palladium-on-charcoal (10 mg) was added and the mixture was heated under reflux for a further 1 hour. The mixture was allowed to cool and water (2 ml) was added. The solution was filtered and the solvent was removed. The residue was purified by reverse-phase column chromatography on Spherisorb C$_{18}$ 300 silica eluting with water and 10% methanol to afford 2-amino-9-(1,4-dihydroxybut-2-oxy)purine (155 mg, 36%), m.p. 178°–179° C.; UV: $\lambda_{max}$ (H$_2$O) 222 ($\epsilon$24,100) and 304 ($\epsilon$7,020)nm; IR: $\upsilon_{max}$ (KBr) 3330, 3210, 3070, 1655, 1640, 1580, 1510, 1480 and 1435 cm$^{-1}$; $^1$H NMR: δH [(CD$_3$)$_2$SO] 1.84 (2H, q, J=6.4 Hz, 3'-H), 3.58 (4H, m, 1'-H and 4'-H), 4.42 (1H, m, 2'-H), 4.63 (1H, t, J=5.2 Hz, D$_2$O exchangeable, OH), 4.98 (1H, t, J=5.9 Hz, D$_2$O exchangeable, OH), 6.70 (2H, s, D$_2$O exchangeable, 2-NH$_2$), 8.23 (1H, s, 8-H) and 8.59 (1H, s, 6-H). Found: C, 45.13; H, 5.47; N, 29.30%. C$_9$H$_{13}$N$_5$O$_3$ requires C, 45.18; H, 5.48; N, 29.27%.

EXAMPLE 10

2-Amino-9-(3-hydroxyprop-1-oxy)purine

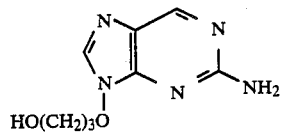

9-(3-t-Butyl]dimethylsilyloxyprop-1-oxy)-2-formamidopurine (800 mg, 2.28 mmol) in 80% acetic acid (20 ml) was heated at 90° C. for 20 minutes. The mixture was then cooled, evaporated under reduced pressure and the residue co-evaporated with water. The residue was dissolved in ethanol (20 ml) and hydrazine hydrate (1 ml). The solution was heated under reflux for 1 hour, cooled and evaporated to dryness. Column chromatography on silica gel (eluted with chloroform-ethanol, 8:1) gave the title compound (262 mg, 55%).

IR:$\upsilon_{max}$ (KBr) 3340, 3210, 1655, 1615, 1570, 1510, 1430 cm$^{-1}$.

$^1$H NMR:δ$_H$[(CD$_3$)$_2$SO] 1.84(2H, quintet, J=6.5 Hz, CH$_2$CH$_2$CH$_2$), 3.58(2H,q, J=6.5, 5.2 Hz, CH$_2$OH), 4.39(2H,t, J=6.5 Hz,CH$_2$ON), 4.62(1H, t, J=5.2 Hz, OH), 6.71(2H, br.s, D$_2$O exchangeable, NH$_2$) 8.31(1H,s,H-8), 8.59(1H,s,H-6).

Found: C,45.89; H,5.38; N,33.85%. C$_8$H$_{11}$N$_5$O$_2$ requires: C,45.92; H,5.31; N,33.49%.

EXAMPLE 11

9-(3-Hexanoyloxyprop-1-oxy)guanine

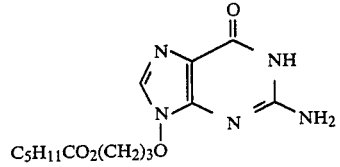

A mixture of 9-(3-hydroxyprop-1-oxy)guanine (150 mg, 0.67 mmol), 4-dimethylaminopyridine (15.6 mg, 0.13 mol), hexanoic anhydride (0.31 ml, 1.34 mmol) and N,N-dimethylformamide was stirred at 20° C. for 2 hours. The mixture was then evaporated to dryness and the residue was chromatographed on silica gel (eluted with chloroform-ethanol, 4:1). Recrystallisation from water-methanol afforded 9-(3-hexanoyloxyprop-1-oxy)-guanine (80 mg; 39%). IR: $\upsilon_{max}$(KBr) 3337, 3172, 2957, 2933, 1696, 1646, 1599, 1587, 1390 cm$^{-1}$; $^1$H NMR: δH [(CD$_3$)$_2$SO] 0.84 (3H, t, J=6.9 Hz, CH$_3$), 1.24 (4H, m, CH$_2$CH$_2$CH$_3$), 1.51 (2H, quintet,

1.98 (2H, quintet, J=6.6, 6.3 Hz, OCH$_2$CH$_2$CH$_2$O) 2.29 (2H, t, J=7.4 Hz,

4.19 (2H, d-d, J=6.6, 6.3 Hz, CH$_2$ON), 4.32 (2H, d-d, J=6.6, 6.3 Hz,

6.58 (2H, br.s, D$_2$O exchangeable, NH$_2$) 7.93 (1H, s, H-8), 10.66 (1H, br.s, D$_2$O exchangeable, H-1).

Found: C, 51.74; H, 6.61; N, 21.49%. C$_{14}$H$_{21}$N$_5$O$_4$ requires C, 51.99; H, 6.56; N, 21.66%.

EXAMPLE 12

2-Amino-9-(1,4-diacetoxybut-2-oxy)purine

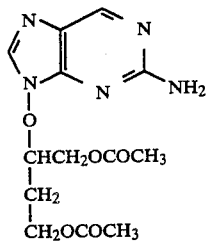

A solution of 2-amino-9-(1,4-dihydroxybut-2-oxy)purine (100 mg, 0.42 mmol), 4-dimethylaminopyridine (4 mg) and acetic anhydride (0.14 ml, 1.5 mmol) in N,N-dimethylformamide (3 ml) was stirred at room temperature for 15 minutes and methanol (0.5 ml) was then added. The solvent was removed and the residue was partitioned between chloroform (5 ml) and aqueous sodium bicarbonate (3 ml). The aqueous layer was extracted with chloroform again (5 ml) and the combined organic extracts were dried (magnesium sulphate) and the solvent removed. The residue was purified by column chromatography on silica gel eluting with chloroform-methanol (30:1). Trituration with hexane-ethyl acetate afforded 2-amino-9-(1,4-diacetoxybut-2-oxy)purine as white crystals (112 mg, 83%), m p. 123°–125° C.; IR: $\upsilon_{max}$(KBr) 3400, 3310, 3190, 1735, 1640, 1615, 1585, 1505, 1470 and 1430 cm$^{-1}$; $^1$H NMR: $\delta$H [(CD$_3$)$_2$SO] 2.0–2.5 (8H, m, 3'-H and 2×CH$_3$), 4.21 (1H, dd, J=12.7 Hz and 5.8 Hz, 1'-H), 4.32 (1H, dt, J$_d$=10.9 Hz and J$_t$=5.4 Hz, 4'-H), 4.54 (1H, dd, J=12.9 Hz and 2.8 Hz, 1'-H), 4.63 (1H, m, 2'-H), 4.81 (1H, ddd, J=11.3·Hz, 9.4 Hz and 4.4 Hz, 4'-H), 5.16 (2h, s, D$_2$O exchangeable, 2-NH$_2$), 7.96 (1H, 8-H) and 8.67 (1H, s, 6-H). Found: C, 48.15; H, 5.23; N, 21.51%. C$_{13}$H$_{17}$N$_5$O$_5$Requires C, 48.29; H, 5.30; N, 21.66%.

EXAMPLE 13

2-Amino-9-(1,4-dibutyryloxybut-2-oxy)purine

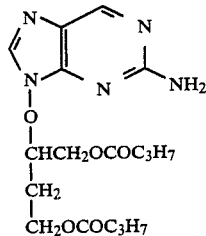

A solution of 2-amino-9-(1,4-dihydroxybut-2-oxy)purine (75 mg, 0.31 mmol), 4-dimethylaminopyridine (3 mg) and butyric anhydride (0.17 ml, 1.0 mmol) in N,N-dimethylformamide (3 ml) was stirred at room temperature for 20 minutes and methanol (0.5 ml) was then added. The solvent was removed and the residue was partitioned between chloroform (5 ml) and aqueous sodium bicarbonate (3 ml). The organic layer was dried (magnesium sulphate) and the solvent was removed. The residue was purified by column chromatography on silica gel eluting with chloroform-methanol (40:1). Crystallisation from ether-hexane afforded 2-amino-9-(1,4-dibutyryloxybut-2-oxy)purine as a white solid (79 mg, 67%), m.p. 99°–101° C.; IR: $\upsilon_{max}$(KBr) 3400, 3310, 3190, 2970, 1735, 1640, 1615, 1580, 1505, 1470 and 1430 cm$^{-1}$; $^1$H NMR: $\delta$H [(CD$_3$)$_2$SO] 0.94 (6H, t, J=7.4 Hz, 2×CH$_3$), 1.64 (4H, m, 2×CH$_2$CH$_3$), 2.09 (1H, m, 3'-H), 2.17 (1H, m, 3'-H), 2.30 (4H, q, J=7.1 Hz, 2×CH$_2$CO), 4.21 (1H, dd, J=12.6 Hz and 5.5 Hz, 1'-H), 4.33 (1H, dt, J$_d$=11.0 Hz and J$_t$=5.4 Hz, 4'-H), 4.55 (1H, dd, J=12.8 Hz and 2.9 Hz, 1'-H), 4.62 (1H, m, 2'-H), 4.79 (1H, ddd, J=11.3 Hz, 9.1 Hz and 4.7 Hz, 4'-H), 5.14 (2H, s, D$_2$O exchangeable, 2-NH$_2$), 7.95 (1H, s, 8-H) and 8.66 (1H, s, 6-H).

Found: C, 53.45; H, 6.66; N, 18.34%. C$_{17}$H$_{25}$N$_5$O$_5$ requires C, 53.82; H, 6.64; N, 18.46%.

EXAMPLE 14

(R)-9-(1,4-Dihydroxybut-2-oxy)guanine

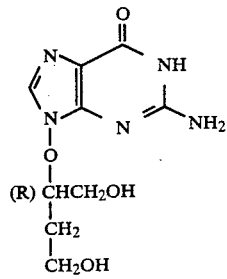

A solution of (R)-9-(1,4-dibenzyloxybut-2-oxy)guanine (80 mg, 0.18 mmol) in tetrahydrofuran (4 ml) and water (1 ml) was treated with 5M hydrochloric acid (3 drops) and 10% palladium-on-charcoal (40 mg). The mixture was hydrogenated under atmospheric pressure for 2 hours, then filtered and fresh catalyst (100 mg) added. Hydrogenation was continued for 16 hours and the mixture filtered, washing the catalyst with boiling water (3×5 ml). The solution was neutralised with IR 45 (OH) ion exchange resin, filtered and evaporated to dryness. The residue was chromatographed on silica, eluting with chloroform-methanol 5:2 to give (R)-9-(1,4-dihydroxybut-2-oxy)guanine (22 mg, 48%); UV: $\lambda_{max}$(EtOH) 252, 270 nm (s); $^1$H NMR: $\delta$H [(CD$_3$)$_2$SO] 1.80 (2H, m, CH$_2$), 3.55 (4H, m, 2×CH$_2$), 4.35 (1H, m, CH), 4.64 (1H, t, J=5 Hz, D$_2$O exchangeable OH), 5.00 (1H, t, J=6 Hz, D$_2$O exchangeable OH), 6.67 (2H, s, D$_2$O exchangeable NH$_2$), 7.87 (1H, s, CH), 10.76 (1H, br.s., D$_2$O exchangeable NH); m/z 255 (M+, 2%), 221 (10), 178 (15), 167 (20), 165 (10), 152 (10), 151 (35), 150 (5), 135 (5), 108 (10), 91 (10), 75 (55), 58 (60), 57 (100), 45 (50), 43 (60). M+ observed 255.0968. C$_9$H$_{13}$N$_5$O$_4$ requires M+ 255.0967.

EXAMPLE 15

(S)-9-(1,4-Dihydroxybut-2-oxy)guanine

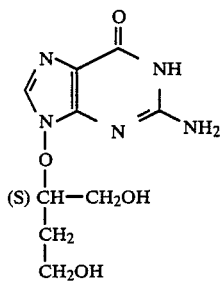

A solution of (S)-6-chloro-9-(1,4-dibenzyloxybut-2-oxy)-2-formamidopurine (0.4 g, 0.8 mmol) in 80% formic acid (20 ml) was heated at 100° C. for 1 hour and cooled to room temperature. To the solution was added 10% palladium-on-charcoal catalyst (200 mg) and the mixture was hydrogenated under atmospheric pressure for 1 hour, then filtered. The filtrate was evaporated to dryness under reduced pressure and the residue dissolved in methanol (2 ml) and 0.88 ammonia (2 ml) and stirred at room temperature for 30 minutes. The solvent was removed under vacuum and the residue chromatographed on reverse phase silica, eluting with water, 5% methanol-water and 10% methanol-water. The product eluted in the 5% and 10% methanol fractions and crystallised from these fractions giving
(S)-9-(1,4-dihydroxybut-2-oxy)guanine (0 12 g, 56%) m.p. 248° C. (dec), $[\alpha]_D^{25} -32.3°$ (c 0.16 in water); UV: $\lambda_{max}$ 252 ($\epsilon$13040), 270 (s); IR: $\upsilon_{max}$ (KBr) 3364, 3298, 3243, 3199, 3133, 2959, 1710, 1690, 1644, 1610, 1600, 1578, 1529, 1474, 1410, 1385, 1368, 1323, 1257, 1226, 1206, 1167, 1124, 1068, 1055, 1025, 1015, 968, 948, 867, 849, 781, 696 cm$^{-1}$; $^1$H NMR: $\delta$H [(CD$_3$)$_2$SO] 1.80 (2H, m, CH$_2$), 3.55 (4H, m, 2×CH$_2$), 4.30 (1H, m, CH), 4.63 (1H, t, J=5 Hz, D$_2$O exchangeable, OH), 4.98 (1H, t, J=6 Hz, D$_2$O exchangeable, OH), 6.60 (2H, s, D$_2$O exchangeable NH$_2$), 7.86 (1H, s, CH), 10.70 (1H, s, D$_2$O, exchangeable NH).

Found: C, 40.90, H, 5.16; N, 26.72%. C$_9$H$_{13}$N$_5$O$_4$.0.5 H$_2$O requires C, 40.90; H, 5.34; N, 26.50%).

EXAMPLE 16

2-Amino-9-(3-hydroxy-2-hydroxymethylprop-1-oxy)-purine

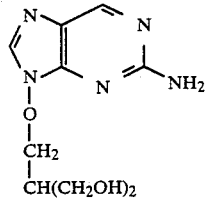

2-Amino-9-(2,2-dimethyl-1,3-dioxan-5-ylmethoxy)-purine (500 mg, 1.79 mmol) in 80% acetic acid was stirred at 20° C. for 3 hours. The mixture was then evaporated to a syrup and co-evaporated with toluene. Column chromatography on silica gel (eluted with chloroform-ethanol, 5:1 and then 5:2) afforded the title compound (371 mg, 87%). IR: $\upsilon_{max}$ (KBr) 3336, 3203, 1647, 1618, 1578, 1430 cm$^{-1}$. $^1$H NMR: $\delta_H$[(CD$_3$)$_2$SO] 1.97 (1H,m,CH), 3.55(4H,m, 2×CH$_2$OH), 4.33(2H,d, J=6.3 Hz, CH$_2$ON), 4.59(2H, t, J=5.3 Hz, D$_2$O exchangeable, 2×OH), 6.70(2H, br.s, D$_2$O exchangeable, NH$_2$), 8.30(1H,s,H-8), 8.59(1H,s,H-6).

Found: C,45.05; H,5.63; N,29.44%; M$^+$ 239.1022. C$_9$H$_{13}$N$_5$O$_3$ requires: C, 45.17; H, 5.49; N, 29.28%; M$^+$ 239.1018.

EXAMPLE 17

9-(3-Acetoxy-2-acetoxymethylprop-1-oxy)-2-aminopurine

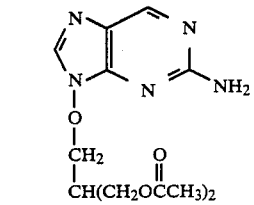

A mixture of 2-Amino-9-(3-hydroxy-2-hydroxymethyl-prop-1-oxy)purine (90 mg, 0.376 mmol), acetic anhydride (0.1 ml, 1.06 mmol), 4-dimethylaminopyridine (10 mg, 0.0836 mmol) and N,N-dimethylformamide (2 ml) was stirred at 20° C. for 1.5 hours. Ethanol (0.2 ml) was added, the mixture stirred for a further 15 minutes and then evaporated under reduced pressure. Column chromatography on silica gel (eluted with chloroform-ethanol, 19:1) yielded a syrup that solidified on trituration with ether. (110.3 mg, 91%). IR: $\upsilon_{max}$ (KBr) 3328, 3191, 1740, 1652, 1618, 1581, 1513, 1431 cm$^{-1}$. $^1$H NMR: $\delta_H$[(CD$_3$)$_2$SO] 2.03 (6H,s, 2×CH$_3$), 2.50(m,CH,(CH$_3$)$_2$SO), 4.20(4H,m, 2×CH$_2$OC=O), 4.39(2H,d, J=6.3 Hz,CH$_2$ON), 6.68(2H,br.s, D$_2$O exchangeable. NH$_2$). 8.32(1H,s,H-8). 8.60(1H,s,H-6).

Found: C,48.34; H,5.30; N,21.57%; M$^+$ 323.1225. C$_{13}$H$_{17}$N$_5$O$_5$ requires: C,48.29, H,5.31; N,21 66%; M$^+$ 323.1230.

EXAMPLE 18

2-Amino-9-(3-propionyloxy-2-propionyloxymethyl-prop-1-oxy)purine

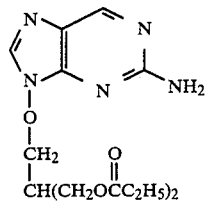

A mixture of 2-Amino-9-(3-hydroxy-2-hydroxymethyl-prop-1-oxy)purine (90 mg, 0.376 mmol), propionic anhydride (0.12 ml, 0.920 mmol), 4-dimethylaminopyridine (9 mg, 0.0752 mmol) and N,N-dimethylformamide (2 ml) was stirred at 20° C. for 1.5 hours. Ethanol (0.2 ml) was added, the mixture stirred for a further 15 minutes and then evaporated under reduced pressure. Column chromatography on silica gel (eluted with chloroform-ethanol, 19:1) gave a syrup that solidified on trituration with ether (122 mg, 83%). IR: $\upsilon_{max}$ (KBr) 3382, 3313, 1740, 1641, 1619, 1575, 1429 cm$^{-1}$.H NMR: $\delta_H$ [(CD$_3$)$_s$SO] 1.02(6H, t, J=7.4 Hz, 2×CH$_3$), 2.33(4H, quartet, J=7.4 Hz, 2×CH$_2$ C=O), 4.22(4H,m,2×CH$_2$OC=O) 4.39(2H,d, J=6.3 Hz, CH2ON), 6.68(2H, br.s, D2O exchangeable, NH2), 8.32(1H,s,H-8), 8 60(1H,s,H-6).

Found: C,51.20; H,6.04; N,19.94%; M+ 351.1525. C15H21N5O5 requires: C,51.26; H.6.04; N.19.93%: M+ 351.1543.

EXAMPLE 19

2-Amino-9-(3-benzoyloxy-2-benzoyloxymethylprop-1-oxy)purine

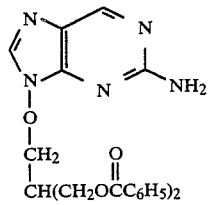

A mixture of 2-Amino-9-(3-hydroxy-2-hydroxymethylprop-1-oxy)purine (80 mg, 0.335 mmol), benzoic anhydride (189 mg, 0.835 mmol), 4-N,N-dimethylaminopyridine (8 mg, 0.668 mmol) and N,N-dimethylformamide (2 ml) was stirred at 20° C. for 2 hours. Ethanol (0.2 ml) was added, the mixture stirred for a further 15 minutes and then evaporated under reduced pressure. Column chromatography on silica gel (eluted with chloroform-ethanol, 19:1) gave a syrup that was recrystallised from ether, affording the title compound (92.2 mg, 65%). IR: $v_{max}$(KBr) 3327, 1721, 1617, 1576, 1426 cm$^{-1}$. H NMR: $\delta_H$ [(CD3)2SO] 2.82(1H,m,CH,), 4.60(6H,m 3×CH2), 6.64(2H,br.s, D2O exchangeable, NH2), 7.51 (4H, t, aromatic), 7.65(2H, t, aromatic), 7.97(4H,d, aromatic), 8.39(1H,s,H-8),8.60 (1H,s,H-6).

Found: C,61.56; H,4 79; N,15.56%. C23H21N5O5 requires: C,61.73; H,4.74; N,15.65%.

EXAMPLE 20

9-Amino-9-(3-hydroxy-2-hydroxymethylprop-1-oxy)-6-methoxyourine

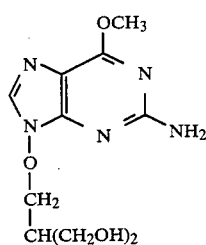

2-Amino-9-(2,2-dimethyl-1,3-dioxan-5-ylmethoxy)-6-methoxypurine (290 mg, 0.938 mmol) in 80% acetic acid (10 ml) was stirred at 20° C. for 3 hours and then evaporated under reduced pressure. The residue was co-evaporated with toluene and then chromatographed on silica gel (eluted with chloroform-ethanol, 10:1) affording the title compound (224 mg, 89%). IR: $v_{max}$ (KBr) 3332, 3213, 1617, 1584. 1509. 1491. cm$^{-1}$. $^1$H NMR: $\delta_H$ [(CD3)2SO] 1.95(1H,m,CH), 3.53(4H,m, 2×CH2OH),3.96(3H,s,OCH3), 4.29(2H,d,J=6.3 Hz, CH2ON), 4.59(2H, t, J=5.2 Hz, D2O exchangeable, 2×OH), 6.60(2H,br.s, D2O exchangeable, NH2), 8.09(1H,s,H-8).

Found: C,44.51; H,5.68; N,26.14%; M+ 269.1127. C10H15N5O4. requires: C,44.60; H,5.63; N,26.01%; M+ 269.1124.

EXAMPLE 21

2,6-Diamino-9-(3-hydroxy-2-hydroxymethylprop-1-oxy)purine

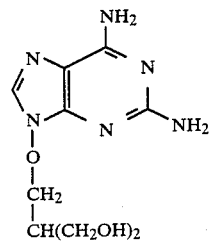

2,6-Diamino-9-(2,2-dimethyl-1,3-dioxan-5-ylmethoxy)-purine (310 mg, 1.05 mmol) in 80% acetic acid was stirred at 20° C. for 4 hours and then evaporated under reduced pressure. The residue was co-evaporated with toluene and then chromatographed on reverse phase silica (Spherisorb V.L.S. C18 300 pore), eluting with water, 5% methanol and 10% methanol. Recrystallisation from water afforded the title compound (208 mg, 78%). IR: $v_{max}$ (KBr) 3356, 3208, 1663, 1628, 1600, 1482, 1445, 1409, cm$^{-1}$. $^1$H NMR: $\delta_H$ [(CD3)2SO] 1.95(1H,m,CH), 3.54(4H,m, 2×CH2OH),4.27(2H,d, J=6.3 Hz, CH2ON), 4.62(2H, t, J=5.3 Hz, D2O exchangeable, 2×OH), 5.92(2H,br.s, D2O exchangeable, 6-NH2), 6.80(2H,br.s, D2O exchangeable, 2-NH2), 7.92(1H,s,H-8).

Found: C,39.76; H,5.90; N,31.32%; M+ 254.1124. C9H14N6O3.0.9H2O requires: C,39.96; H,5.90; N,31 07%; M+ 254.1127.

EXAMPLE 22

9-(3-Acetoxyprop-1-oxy)-2-aminopurine

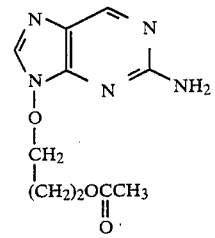

A mixture of 2-amino-9-(3-hydroxyprop-1-oxy)purine (60 mg, 0.287 mmol), acetic anhydride (0.033ml, 0.35 mmol), 4 4-N,N-dimethylaminopyridine (6 mg, 0.05 mmol) and N,N-dimethylformamide (1 ml) was stirred at 20° C. for 3 hours. Ethanol (0.5 ml) was added and the mixture evaporated to dryness. Column chromatography on silica gel (eluted with chloroform-ethanol, 10:1) afforded the title compound (68.8 mg, 95%). 1R: $v_{max}$ (KBr) 3311, 3154, 1721, 1665, 1614. 1572, 1430 cm$^{-1}$ .$^1$H NMR:$\delta_H$[(CD3)2SO]2.02(4H,m,CH3, CH), 4.20(2H, t, J=6.5 Hz, CH2OC=O), 4.39(2H, t, J6.3 Hz, CH2ON), 6.70(2H,br.s, D2O exchangeable, NH2), 8.32(1H,s,H-8), 8.59(1H,s,H-6).

Found: M+251, 1013 C10H13N5O3. requires: M+251.1018.

EXAMPLE 23

2-Amino-9-(3-hexanoyloxyprop-1-oxy)purine

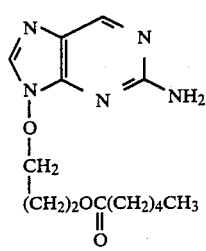

A mixture of 2-amino-9-(3-hydroxyprop-1-oxy)purine (60 mg, 0.287 mmol), hexanoic anhydride (0.1 ml, 0.432 mmol), 4-dimethylaminopyridine (6 mg, 0.05 mmol) and N,N-dimethylformamide (1 ml) was stirred at 20° C. for 3 hours. Ethanol (0.5 ml) was added and the solvent removed under reduced pressure. Column chromatography on silica gel (eluted with chloroform-ethanol, 10:1) yielded the title compound (65 mg, 74%). 1R: $\nu_{max}$ (KBr) 3337, 3187, 1724, 1656, 1616, 1578, 1511, 1429 cm$^{-1}$ $^1$H NMR:$\delta_H$[(CD$_3$)$_2$SO]0.84(3H, t, J=6.8 Hz, CH$_3$), 1.24(4H,m,CH$_2$CH$_2$CH$_3$), 1.52(2H,m,CH$_2$CH$_2$C=O), 2.01(2H,quintet, J=6.6, 6.3 Hz OCH$_2$CH$_2$CH$_2$O), 2.30(2H, t, J=7.3 Hz, CH$_2$C=O), 4.21(2H, t, J=6.6 Hz,CH$_2$OC=O), 4.39(2H, t, J=6.3 Hz, CH$_2$ON), 6.70(2H,br.s,D$_2$O exchangeable, NH$_2$), 8.32(1H,s,H-8), 8.59(1H,s,H-6).

Found: C,54.78; H,6.96; N,22.99%; M$^+$307.1656. C$_{14}$H$_{21}$N$_5$O$_3$ requires: C,54.70; H,6 90; N,22.79%; M$^+$307.1644.

EXAMPLE 24

2-Amino-9-(3-benzoyloxyprop-1-oxy)purine

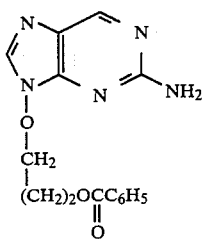

A mixture of 2-amino-9-(3-hydroxyprop-1-oxy)purine (60 mg, 0.287 mmol), benzoic anhydride (97.4 mg, 0.431 mmol), 4-dimethylaminopyridine (6 mg, 0.05 mmol) and N,N-dimethylformamide (1 ml) was stirred at 20° C. for 3 hours. Ethanol (0.5 ml) was added and the solvent removed under reduced pressure. Column chromatography on silica gel (eluted with chloroform-ethanol, 10:1) yielded a white solid Extraction of the solid with boiling ether gave the title compound (65.0 mg, 69%). 1R: $\nu_{max}$(KBr) 3351, 3324, 3195, 1713, 1646, 1620, 1573, 1511, 1430 cm$^{-1}$. $^1$H NMR:$\delta_H$[(CD$_3$)$_2$SO]2.17(2H, quintet, J=6.3 Hz, CH$_2$CH$_2$CH$_2$), 4.50(4H,m,CH$_2$ON,CH$_2$OC=O), 6.68(2H,br.s, D$_2$O exchangeable, NH$_2$), 7.53 (2H,m, aromatic), 7.67(1H,m, aromatic), 7.99(2H,m, aromatic), 8.35(1H,s,H-8), 8.60(1H,s,H-6).

Found: C,56.51; H,4.74; N,21.86%; M$^+$313.1176. C$_{15}$H$_{15}$N$_5$O$_3$. 0.3H$_2$O requires: C,56.52; H, 4.94; N,21,98%; M$^+$313.1175.

EXAMPLE 25

(S)-9-(1,4-Diacetoxybut-2-oxy)quanine

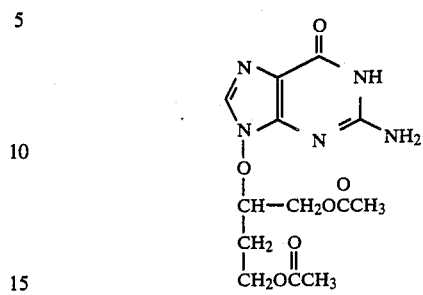

A solution of (S)-9-(1,4-dihydroxybut-2-oxy)guanine (50 mg, 0.2 mmol), in dry N,N-dimethylformamide (3 ml) was treated with acetic anhydride (0.15 ml, 1.6 mmol) and 4-dimethylaminopyridine (4 mg) The solution was stirred at room temperature for 1 hour, the solvent removed and the residue dissolved in chloroform (30 ml) and shaken with saturated sodium bicarbonate solution (20 ml). The chloroform layer, containing some precipitated product, was evaporated to dryness and the residue chromatographed on silica, eluting with chloroform-methanol (30:1), to give (S)-9-(1,4-diacetoxybut-2-oxy)guanine (40 mg, 60%). IR: (KBr) $\nu_{max}$ 3430, 3310, 3200, 3120, 3015, 2930, 2900, 2850, 2790 2740, 1740, 1720, 1700, 1630, 1600, 1535, 1475, 1430, 1380, 1375, 1320, 1240, 1225, 1160, 1115, 1065, 1055, 1010, 960, 945, 900, 890, 860, 825, 780 cm$^{-1}$ $^1$H NMR:$\delta$H[(CD$_3$)$_2$SO]$\delta$2.02(8H,m,2×CH$_3$ plus CH$_2$), 4.17(4H,m,2×CH$_2$), 4.61(1H,m, CH), 6.47(2H,s, D$_2$O exchangeable, NH$_2$), 7.90 (1H,s, CH), 10.69 (1H,s,D$_2$O exchangeable NH).

Found: C,44.50; H,5.04; N,19.95%. C$_{13}$H$_{17}$N$_5$O$_6$. 0.5H$_2$O requires: C,44.82; H,5.21; N,20.11%.

EXAMPLE 26

2-Amino-9-(2,3-dihydroxyprop-1-oxy)-6-methoxypurine.

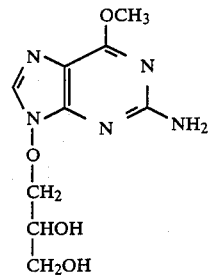

2-Amino-6-chloro-9-(2,3-dihydroxyprop-1-oxy)purine (60 mg, 0.23 mmol) was dissolved in a 1.3M sodium methoxide solution in methanol (0.55 ml, 0.68 mmol) and stirred at 100° C. for 1.5 hours. The reaction was evaporated to dryness under reduced pressure, the residue absorbed on silica and chromatographed using chloroform-methanol (20:1), affording the title compound (30 mg, 51%) as a hygroscopic foam. IR: $\nu_{max}$ (KBr) 3400, 3220, 1620, 1590, 1500, 1480, 1400 cm$^{-1}$; $^1$H NMR: $\delta_H$[(CD$_3$)$_2$SO]3.40(2H,m, CH$_2$OH), 3.75($^1$H,m, CHOH), 3.96 (3H,s, CH$_3$). 4.13(1H,q, J=7.7, 10.5 Hz, CH$_2$ON), 4.36(1H,q, J=3.3, 10.5 Hz, CH20N),4.71(1H, t, J=5.8 Hz, D$_2$O exchangeable, OH), 5.18(1H,d, J=5.2 Hz, D$_2$O exchangeable, OH), 6.64(2H,br.s, NH$_2$), 8.07(1H,s,H-8). m/z 255 (M+, 31%).

Found: C, 40.95; H, 5.40; N, 26.62%; M+255.0965. C$_9$H$_{13}$N$_5$O$_4$.0.5H$_2$O. requires: C, 40.91; H, 5.34; N, 26.51%; M+255.0967.

EXAMPLE 27

(R)-9-(2,3-Dihydroxyprop-1-oxy)guanine

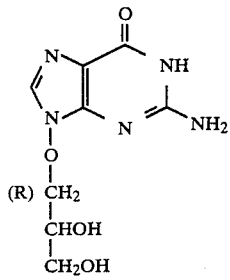

(R)-6-chloro-9-(2,2-dimethyl-1,3-dioxolan-4-ylmethoxy)-2-formamidopurine (150 mg, 0.46 mmol) was dissolved in 80% formic acid (6 ml) and stirred for 2.5 hours at 100° C. The solvent was removed under reduced pressure, the residue dissolved in methanol (1 ml) containing 0.88 ammonia (1 ml) and the solution stirred at 25° C. for 1 hour. The reaction was evaporated to dryness, the residue dissolved in a minimum amount of water and the solution filtered hot through a glass fibre paper. 22 Slow cooling of the filtrate afforded (R)-9-(2,3-dihydroxyprop-1-oxy)guanine (50 mg, 45%), m.p. 255° d., [α]$_D^{25}$ −14.9° (C 0.1 in Water). UV: λ$_{max}$(H$_2$O) 252 (ε12,200)nm, IR: ν$_{max}$(KBr) 3340, 3190, 1690, 1640, 1600, 1540 cm$^{-1}$, $^1$H NMR: δ$_H$[(CD$_3$)$_2$SO]3.39 (2H,m, CH$_2$OH), 3.73 (1H,m,CH), 4.10 (1H ,q,J=7.7, 10.5 Hz, CH$_2$ON), 4.32 (1H, q, J=3.3, 10.5 Hz, CH$_2$ON), 4.70 (1H, t, J=5 6 Hz, D$_2$O exchangeable, OH), 5.15. (1H, d, J=5.0 Hz, D$_2$O exchangeable, OH), 6.62 (2H, br, s, D$_2$O exchangeable, NH$_2$), 7.90 (1H, s, H-8), 10.55 (1H, br.s, D$_2$O exchangeable, NH). m/z 241 (M+, 2%).

Found: C, 37.91; H, 4.80; N, 28.11%; M+241.0797. C$_8$H$_{11}$N$_5$O$_4$.0.5H$_2$. requires C, 38.39; H, 4.82; N, 28.00%; M+241.0807

EXAMPLE 28

9-(3,4-Dihydroxybut-1-oxy)guanine

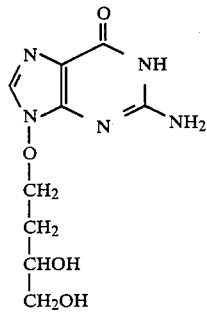

A solution, of 2-amino-6-chloro-9-(3,4-dihydroxybut-1-oxy)purine (100 mg, 0.37 mmol) in 80% formic acid (7 ml) was stirred at 100° C. for 1.5 hours. The reaction was evaporated to dryness, the residue dissolved in methanol (5 ml) and 0.88 ammonia (5ml) and stirred for 0.5 hour at 25° C. The solvents were removed under reduced pressure, the residue dissolved in hot water and filtered. The filtrate was slowly cooled affording 9-(3,4-dihydroxybut-1-yl)guanine (65 mg, 70%) as a pale brown solid, m.p. 254°–8° C. UV: λ$_{max}$ (H$_2$O) 252 (ε12,900)nm. 1R: ν$_{max}$ (KBr) 3330, 3170. 1690, 1640, 1600, 1540, 1475 cm$^{-1}$; $^1$H NMR: δ$_H$ [(CD$_3$)$_2$SO]1 64 (1H, m, CH$_2$CH$_2$ON), 1.88 (1H, m, CH$_2$CH$_2$ON), 3.31 (2H, m, CH$_2$OH), 3.61 (1H, m, CHOH), 4.34 (2H, m, CH$_2$ON), 4.58 (1H, t, J=5.5 Hz, D$_2$O exchangeable, OH), 4.64 (1H, d, J=4.9 Hz, D$_2$O exchangeable, OH). 6.59 (2H, br.s, D$_2$O exchangeable, NH$_2$), 7.91 (1H, s, H-8), 10.38 (1H, br.s, D$_2$O exchangeable, NH). m/z 255 (M+, 10%). Found: C, 40.78; H, 5.31; N, 26.66%; M+255.0968. C$_9$H$_{13}$N$_5$O$_4$.0.5H$_2$O requires C, 40.91; H, 5.34; N, 26.51%; M+255.0967.

EXAMPLE 29

2-Amino-9-(3,4-dihydroxybut-1-oxy)purine

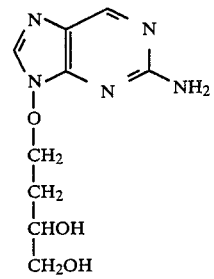

A mixture of 2-amino-6-chloro-9-(3,4-dihyroxybut-1-oxy)purine (150 mg, 0.55 mmol), ammonium formate (140 mg, 2.2 mmol), 10% palladium on charcoal (20 mg) and methanol (5 ml) was heated under reflux for 3 hours. The solution was filtered and the filtrate was evaporated to dryness under reduced pressure. The residues was recrystallised from hot ethanol affording 2-amino-9-(3,4-dihydroxybut-1-oxy)purine (100 mg, 76%), m.p. 157°–8° C. UV: λ$_{max}$ (H$_2$O) 221 (ε24,700), 305 (ε7100)nm. 1R: ν$_{max}$ (KBr) 3420, 3310, 3200, 1640, 1620, 1580, 1520, 1480, 1450 cm$^{-1}$; $^1$H NMR: δ$_H$ [(CD$_3$)$_2$SO]1.65 (1H, m, CH$_2$CH$_2$ON), 1.91 (1H, CH$_2$CH$_2$ON), 3.32 (2H, m, CH$_2$OH), 3.63 (1H, m, CHOH), 4.41 (2H, m, CH$_2$ON), 4.59 (1H, t, J=5.7 Hz, D$_2$O exchangeable, OH), 4.71 (1H, d, J=5.2 Hz, D$_2$O exchangeable, OH) 6.71 (2H, br.s, D$_2$O exchangeable, NH$_2$), 8.30 (1H, s, H-8), 8.59 (1H, s, H-6).

Found: C, 44.94; H, 5.56; N, 29.01%; M+239.1022. C$_9$H$_{13}$N$_5$O$_3$ requires C, 45.18; H, 5.48; N, 29.28%; M+239.1018.

EXAMPLE 30

(R)-2-Amino-9-(2,3-dihydroxyprop-1-oxy)purine

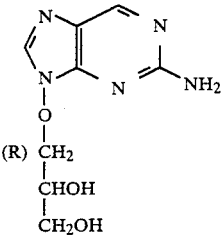

A mixture of (R)-2-amino-6-chloro-9-(2,3-dihydroxyprop-1-oxy)purine (54 mg, 0.21 mmol), 10% palladium on charcoal (10 mg), ammonium formate (53 mg, 0.83 mmol) and methanol (2 ml) was heated under reflux for 3 hours. The reaction was cooled, filtered and evaporated to dryness under reduced pressure. The residue was recrystallised from ethanol affording (R)-2-amino-9-(2,3-dihydroxyprop-1-oxy)purine (26 mg, 55%) as a pale brown solid, m.p. 145°-7° C. 1R: $\nu_{max}$ (KBr) 3380, 3320, 3200, 1650, 1620, 1580, 1520 cm$^{-1}$; $^1$H NMR: $\delta_H$ [(CD$_3$)$_2$SO]3.40 (2H, m, CH$_2$OH), 3.77 (1H, m, CHOH), 4.18 (1H, q, J=7.6, 10.5 Hz, CH$_2$ON), 4.39 (1H, q, J=3.3, 10.5 Hz, CH$_2$ON), 4.73 (1H, m, D$_2$O exchangeable, OH), 5.16 (1H, m, D$_2$O exchangeable, OH), 6.72 (2H, br.s, D$_2$O exchangeable, NH$_2$), 8.27 (1H, s, H-8), 8.59 (1H, s, H-6).

EXAMPLE 31

(S)-9-(2,3-Dihydroxyprop-1-oxy)guanine

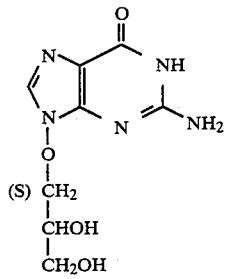

A solution of (S)-6-chloro-9-(2,2-dimethyl-1,3-dioxolan-4-ylmethoxy)-2-formamidopurine (300 mg, 0.92 mmol) in 80% aqueous formic acid (12 ml) was stirred at 100° C. for 2.5h.. The solvents were removed under reduced pressure, the residue dissolved in methanol (2 ml) and 0.88 ammonia (2ml) and the solution stirred at 25° C. for 2h. The reaction was evaporated to dryness, the residue dissolved in a minimum amount of hot water and filtered through a glass fibre paper. Crystallisation of the filtrate and recrystallisation 24 of the deposited solid from water gave (S)-9-(2,3-dihydroxyprop-1- oxy)guanine (100 mg, 45%) as a pale yellow solid; m.p. 252°-5° C. dec. $[\alpha]_D^{25}+13.5°$ (0.16 in H$_2$O); $\lambda$max (H$_2$O)252($\epsilon$12,900)nm; $\nu$max (KBr) 3330, 3180, 1690, 1640, 1600 and 1540cm$^{-1}$; $\delta$H[(CD$_3$)$_2$SO]3.39(2H,m,CH$_2$OH), 3.73(1H,m,CHOH), 4.10(1H,q,J7.7,10.5 Hz,CH$_2$ON), 4.32(1H,q,J3.3,10.5 Hz,CH$_2$ON). 4.70(1H.t,J5.6 Hz,D$_2$O exchangeable, OH), 5.15(1H,d,J5.0 Hz,D$_2$O exchangeable, OH), 6.62(2H,br.s,D$_2$O exchangeable, NH$_2$), 7.90(IH,S,H-8), 10.64(1H,br.s,D$_2$O exchangeable, NH); m/z 241(M+,13%). Found: C,38.89; H,4.81; N,28.09%; M+241.0820; C$_8$H$_{11}$N$_5$O$_4$.0.4H$_2$O requires C,38.68; H,4.79; N,28.19%; M+241.0811.

EXAMPLE 32

(S)-2-Amino-9-(2,3-dihvdroxvproo-1-oxy)purine

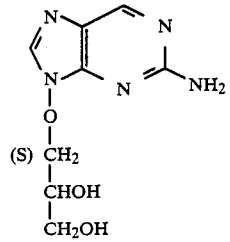

A mixture of (S]-2-amino-6-chloro-9-(2,3-dihydroxyprop-1-oxy)purine(160 mg, 0.62 mmol), ammonium formate (156 mg, 2.5 mmol)and 10% palladium on charcoal (20 mg) in methanol (5 ml) was heated under reflux for 3h. After this time, more ammonium formate (150 mg, 2.5 mmol) and 10% palladium on charcoal (20 mg) were added and the reaction again heated under reflux for 1h. The mixture was filtered hot through a glass fibre paper and the filtrate evaporated under reduced pressure. The residue was recrystallised from hot ethanol affording (S)-2-amino-9-(2,3-dihydroxyprop-1-oxy)-purine (100 mg, 72%) as a white solid; m.p. 153°-5° C. $[\alpha]D^{25}+16.5°$ (0.2 in H$_2$O); $\lambda_{max}$ (H$_2$O) 221 ($\epsilon$25,000), 305($\epsilon$7250)nm; $\nu_{max}$(KBr) 3370, 3310, 3190, 1650, 1620, 1580, 1520, 1480 and 1440cm$^{-1}$; $\delta$H[(CD$_3$)$_2$SO] 3.43(2H,m,CH$_2$OH), 3.77(1H,m,CH), 4.18(1H,q,J7.8,9.7 Hz,CH$_2$ON), 4.40(1H,q,J2.5,10.7 Hz,CH$_2$ON), 4.72(1H,t,J5.4Hz,D$_2$O exchangeable, OH), 5.16(1H,d,J4.9Hz,D$_2$O exchangeable, OH), 6.72(2H,S,D$_2$O exchangeable, NH$_2$), 8.27(1H,S,H-8), 8.59(1H,S,H-6) Found: C,41.26; H,4.93; N,29.50%; C$_8$H$_{11}$N$_5$O$_3$.0.5H$_2$O requires C,41.02; H.5.16; N,29.89%.

Antiviral Activity

Plaque Reduction Test for Heroes Simplex viruses 1 and 2. Cells (vero or MRC-5) were grown to confluence in 24 well multi-dishes (well diameter 1.5 cm). The drained cell monolayers were each infected with approximately 50 infectious particles of herpes simplex virus 1 (HSV-1; strain HFEM) or herpes simplex virus 2 (HSV-2; strain MS) in 100 $\mu$of phosphate-buffered saline. The virus was adsorbed for 1 hour at room temperature. After adsorption, residual inoculum was removed from each well and replaced with 0.5ml of Eagle's MEM containing 5% newborn calf serum and 0.9% agarose (A37). Once the agarose had set, dilutions of the test compound, which had been prepared in Eagle's MEM (containing 5% newborn calf serum), were added, each well receiving 0.5ml of liquid overlay. The test compound was diluted to give the following series of 22 concentrations: 200, 60, 20, 6 . . . 0.06 $\mu$g/ml; final concentrations in the assay ranged, therefore, between 100 $\mu$g/ml and 0.03 $\mu$g/ml. The infected cultures were incubated at 37° C. in a humidified atmosphere of 5% CO$_2$ until plaques were clearly visible (2 or 3 days for Vero cells, usually 1 day for MRC-5 cells).

2. Plaque Reduction Test for Varicella Zoster-Virus MRC-5 cells were grown to confluence in 24 well multi-dishes (well diameter=1.5 cm). The drained cell monolayers were each infected with approximately 50 infectious particles of varicella zoster virus (VZv; Ellen strain) in 100 $\mu$l of phosphate-buffered saline. The virus was adsorbed for 1 hour at room temperature. After adsorption, residual inoculum was removed from each well and replaced with 0.5 ml of Eagle's MEM containing 5% heat-inactivated foetal calf serum and 0.9% agarose (A37). Once the agarose had set, dilutions of the test compound, which had been prepared in Eagle's MEM (containing 5% heat-inactivated foetal calf serum), were added, each well receiving 0.5 ml of liquid overlay. The test compound was diluted to give the following series of concentrations: 200, 60, 20, 6 ... 0.06 μg/ml; final concentrations in the assay ranged, therefore, between 100 μg/ml and 0.03 μg/ml. The infected cultures were incubated at 37° C. in a humidified atmosphere of 5% $CO_2$ until plaques were clearly visible (5 or 6 days).

Cultures from 1 and 2 were fixed in formal saline, the agarose overlays were carefully washed off, and then the cell monolayers were stained with carbol fuchsin. A stereo microscope was used to count plaques. The $IC_{50}$ (concentration of drug which inhibits plaque number by 50% relative to the number of plaques observed in virus control monolayers) of the test compound was calculated. In addition, the monolayers were examined for evidence of drug-induced cytotoxicity; the minimum concentration at which cytotoxicity occurs was recorded.

3. CPE Inhibition Test (Replicating Cells) for Herpes the minimum concentration of test compound which caused cytotoxicity.

4. CPE Inhibition Test (Established Monolayer) for Lentiviruses $3 \times 10^4$ sheep choroid plexus (SCP) cells were plated into individual wells of a 96 well microtitre plate in 100 μl of Eagle's MEM with Hanks salts containing 10% heat inactivated foetal calf serum (FCS). When monolayers had become established (after 1 or 2 days growth) they were washed with 200 μl of maintenance medium (Eagle's MEM with Hanks salts containing 0.5% FCS) and infected with 100μl of visna virus (strain K184) in maintenance medium (30 $TCID_{50}$/ml). Test samples were diluted with maintenance medium in further 96 well microtitre plates over the range 200-0.09 μg/ml by 3-fold dilution steps. 100 μl of the diluted samples was then transferred directly onto virus-infected monolayers (final concentration range therefore 100-0.045 μg/ml) and incubated at 37° C. in a humidified, 5% $CO_2$ incubation until virus-induced CPE was maximal in the untreated virus-infected controls (usually 12-14 days). The plates were fixed with formal saline and stained with crystal violet.

Virus-induced CPE was then scored microscopically and the minimum concentration of sample giving complete protection of the cell monolayers (MIC) determined.

| Results | $IC_{50}$ (μg/ml)[a] | | | | | MIC (μg/ml) |
|---|---|---|---|---|---|---|
| | Herpes Simplex Type 1 virus | | Herpes Simplex Type 2 virus | | Varicella Zoster virus | Visna Virus |
| Example No. | HFEM strain in Vero cells | SC16 strain in MRC-5 cells | MS strain in Vero cells | MS strain in MRC-5 cells | Ellen strain in MRC-5 cells | K184 strain in SCP cells |
| 1 | 0.4,0.2 | 1.0,0.3,0.2 | 0.3,0.2 | 0.1 | 0.8,0.3 | 3.0 |
| 2 | 4.3 | 0.4,0.6 | | 1.1 | | |
| 3 | 2.8 | 1.2 | | 2.1 | | |
| 4 | | 100 | | 67 | 21 | |
| 5 | 1.5 | 1.8,1.8 | 1.5,1.5 | 1.5 | 2.9 | 0.1 |
| 6 | 8.6 | 1.9 | 1.6 | 0.7 | 2.3 | 10 |
| 7 | | 100 | | | 57 | |
| 8 | | 11 | | | | 30 |
| 11 | 0.7 | 0.1 | | | 0.1 | |
| 14 | | 100 | | | | |
| 15 | | 7.4 | | | | |
| 31 | | 0.7 | | 0.06 | | 10 |

[a]Each figure is the value obtained in a single test.

Simplex Virus 1

MRC-5 cells (in Eagles MEM containing 5% newborn calf serum) were infected in suspension with herpes simplex virus 1, strain SC16 (approximately one infectious particle per 10 cells). One hundred microliters of the infected cell suspension (containing approximately $2 \times 10^4$ cells) were dispensed into each well of a 96 well microtitre plate containing an equal volume of the test drug in medium (Eagles MEM containing 5% newborn calf serum) at concentrations ranging from 200 to 0.09 μg/ml (3-fold dilution steps); final concentrations therefore ranged between 100 to 0.045 μg/ml. The plates were then incubated at 37° C. in a humidified atmosphere of 5% $CO_2$ for 3 days when the virus-induced cytopathic effect (CPE) in the control wells reached 100%. The plates were fixed in formal saline and stained with carbol fuchsin. The plates were then examined to find what concentration of test compound reduced the virus-induced CPE by 50% ($IC_{50}$). Plates of uninfected cells were set up in parallel to determine Toxicity At concentrations up to 30 μg/ml, none of the compounds was cytotoxic for uninfected cells used in any of the tests.

What we claim is:

1. A compound of formula (I), or a pharmaceutically acceptable salt thereof:

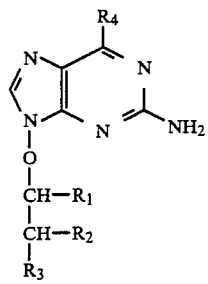

(I)

wherein
 $R_1$ is hydrogen or $CH_2OH$;
 $R_2$ is hydrogen or, when $R_1$ is hydrogen, hydroxy or $CH_2OH$;
 $R_3$ is $CH_2OH$ or, when $R_1$ and $R_2$ are both hydrogen, $CH(OH)CH_2OH$;
 $R_4$ is hydrogen, hydroxy, amino or $OR_5$ wherein
 $R_5$ is $C_{1-6}$ alkyl, phenyl or phenyl $C_{1-2}$ alkyl either of which phenyl moieties may be substituted by one or two halo, $C_{1-4}$ alkyl or $C_{1-4}$ alkoxy groups; and in which any OH groups in $R_1$, $R_2$ and $R_3$ may be in the form of O-acyl, phosphate, cyclic acetal or cyclic carbonate derivatives thereof.

2. A compound of formula (I) according to claim 1, wherein $R_1$ and $R_2$ are both hydrogen and $R_3$ is $CH_2OH$, and derivatives thereof as defined in claim 1.

3. A compound of formula (I) according to claim 1, wherein $R_1$ is hydrogen and $R_2$ and $R_3$ are both $CH_2OH$, and derivatives thereof as defined in claim 1.

4. A compound of formula (I) according to claim 1, wherein $R_1$ is hydrogen, $R_2$ is hydroxy and $R_3$ is $CH_2OH$, and derivatives thereof as defined in claim 1.

5. A compound of formula (I) according to claim 1, wherein $R_1$ is $CH_2OH$, $R_2$ is hydrogen and $R_3$ is $CH_2OH$, and derivatives thereof as defined in claim 1.

6. A compound of formula (I) according to claim 1, wherein $R_1$ and $R_2$ are both hydrogen and $R_3$ is $CH(OH)CH_2OH$, and derivatives thereof as defined in claim 1.

7. A compound according to claim 1 wherein $R_4$ is hydroxy.

8. A compound according to claim 1 wherein $R_4$ is hydrogen.

9. A compound according to claim 1 wherein one or more of the OH groups in $R_1$, $R_2$, and $R_3$ are in the form of an acyl derivative thereof wherein the acyl derivative is an acetate, hexanoate or benzoate.

10. A compound selected from the group consisting of:
 9-(3-hydroxyprop-1-oxy)guanine,
 9-(3-acetoxyprop-1-oxy)guanine,
 9-(3-benzoyloxyprop-1-oxy)guanine,
 2-amino-6-ethoxy-9-(3-hydroxyprop-1-oxy)purine,
 9-(3-hydroxy-2-hydroxymethylprop-1-oxy)guanine,
 9-(2,3-dihydroxyprop-1-oxy)guanine,
 2-amino-9-(2,3-dihydroxyprop-1-oxy)purine,
 9-(1,4-dihydroxybut-2-oxy)guanine,
 2-amino-9-(1,4-dihydroxybut-2-oxy)purine,
 2-amino-9-(3-hydroxyprop-1-oxy)purine,
 9-(3-hexanoyloxyprop-1-oxy)guanine,
 2-amino-9-(1,4-diacetoxybut-2-oxy)purine,
 2-amino-9-(1,4-dibutyryloxybut-2-oxy)purine,
 (R)-9-(1,4-dihydroxybut-2-oxy)guanine,
 (S)-9-(1,4-dihydroxybut-2-oxy)guanine,
 2-amino-9-(3-hydroxy-2-hydroxymethylprop-1-oxy)purine,
 9-(3-acetoxy-2-acetoxymethylprop-1-oxy)-2-aminopurine,
 2-amino-9-(3-propionyloxy-2-propionyloxymethylprop-1-oxy)purine,
 2-amino-9-(3-benzoyloxy-2-benzoyloxymethylprop-1oxy)purine,
 2-amino-9-(3-hydroxy-2-hydroxymethylprop-1-oxy)-6methoxypurine,
 2,6-diamino-9-(3-hydroxy-2-hydroxymethylprop-1-oxy)purine,
 9-(3-acetoxyprop-1-oxy)-2-aminopurine,
 2-amino-9-(3-hexanoyloxyprop-1-oxy)purine,
 2-amino-9-(3-benzoyloxyprop-1-oxy)purine,
 (S)-9-(1,4-diacetoxybut-2-oxy)guanine,
 2-amino-9-(2,3-dihydroxyprop-1-oxy)-6-methoxypurine,
 (R)-9-(2,3-dihydroxyprop-1-oxy)guanine,
 9-(3,4-dihydroxybut-1-oxy)guanine,
 2-amino-9-(3,4-dihydroxybut-1-oxy)purine,
 (R)-2-amino-9-(-2,3-dihydroxyprop-1-oxy)purine,
 (S)-9-(2,3-dihydroxyprop-1-oxy)guanine and
 (S)-2-amino-9-(2,3-dihydroxyprop-1-oxy)purine.

11. An antiviral pharmaceutical composition comprising an effective amount of a compound according to claim 1, or a pharmaceutically acceptable slat thereof, and a pharmaceutically acceptable carrier.

12. A method of treatment of viral infections in human and non-human animals which method comprises the administration to the animal of an effective amount of a compound of formula (I) as defined in claim 1, or a pharmaceutically acceptable salt thereof.

13. A compound selected from the group consisting of:
 9-(3-hydroxyprop-1-oxy)guanine,
 9-(3-acetoxyprop-1-oxy)guanine,
 9-(3-benzoyloxyprop-1-oxy)guanine,
 2-amino-6-ethoxy-9-(3-hydroxyprop-1-oxy)purine,
 2-amino-9-(3-hydroxyprop-1-oxy)purine,
 9-(3-hexanoyloxyprop-1-oxy)guanine,
 9-(3-acetoxyprop-1-oxy)-2-aminopurine,
 2-amino-9-(3-hexanoyloxyprop-1-oxy)purine.

* * * * *

UNITED STATES PATENT AND TRADEMARK OFFICE
CERTIFICATE OF CORRECTION

PATENT NO. : 4,965,270
DATED : October 23, 1990
INVENTOR(S) : Michael R. Harnden et al.

It is certified that error appears in the above-identified patent and that said Letters Patent is hereby corrected as shown below:

On the title page please insert the following:

FOREIGN APPLICATION PRIORITY DATA

May 30, 1987 [GB] United Kingdom. . . . . . . . . 8712744

June 11, 1987 [GB] United Kingdom . . . . . . . . 8713695

Signed and Sealed this

Twenty-eighth Day of July, 1992

Attest:

DOUGLAS B. COMER

Attesting Officer     Acting Commissioner of Patents and Trademarks